United States Patent
Glidden et al.

(10) Patent No.: US 9,040,483 B2
(45) Date of Patent: May 26, 2015

(54) CONTROLLED RELEASE COMPOSITIONS OF AGENTS THAT REDUCE CIRCULATING LEVELS OF PLATELETS AND METHODS THEREFOR

(75) Inventors: Paul F. Glidden, San Diego, CA (US); Alison J. Pilgrim, Castillon-du-Gard (FR); Stephen R. Hanson, Edmonds, WA (US)

(73) Assignee: BIOVASCULAR, INC., La Jolla, CA (US)

( * ) Notice: Subject to any disclaimer, the term of this patent is extended or adjusted under 35 U.S.C. 154(b) by 0 days.

(21) Appl. No.: 13/551,526

(22) Filed: Jul. 17, 2012

(65) Prior Publication Data

US 2013/0022671 A1    Jan. 24, 2013

Related U.S. Application Data

(63) Continuation of application No. 12/456,443, filed on Jun. 16, 2009, now abandoned.

(60) Provisional application No. 61/132,429, filed on Jun. 16, 2008, provisional application No. 61/209,056, filed on Mar. 2, 2009.

(51) Int. Cl.
| | |
|---|---|
| A61P 7/02 | (2006.01) |
| C07D 239/72 | (2006.01) |
| A61K 9/48 | (2006.01) |
| A61K 9/50 | (2006.01) |
| A61K 31/00 | (2006.01) |
| A61K 31/519 | (2006.01) |
| A61L 27/02 | (2006.01) |
| A61L 27/20 | (2006.01) |
| A61L 27/22 | (2006.01) |
| A61L 27/34 | (2006.01) |
| A61L 27/54 | (2006.01) |
| A61L 27/56 | (2006.01) |
| C07D 487/04 | (2006.01) |

(52) U.S. Cl.
CPC ............ *C07D 239/72* (2013.01); *A61K 9/4808* (2013.01); *A61K 9/5078* (2013.01); *A61K 31/00* (2013.01); *A61K 31/519* (2013.01); *A61L 27/025* (2013.01); *A61L 27/20* (2013.01); *A61L 27/227* (2013.01); *A61L 27/34* (2013.01); *A61L 27/54* (2013.01); *A61L 27/56* (2013.01); *C07D 487/04* (2013.01); *A61L 2300/42* (2013.01); *A61L 2300/602* (2013.01); *A61L 2300/608* (2013.01); *A61L 2300/622* (2013.01); *A61L 2300/63* (2013.01); *A61L 2420/08* (2013.01)

(58) Field of Classification Search
USPC ...................................................... 514/13.7
See application file for complete search history.

(56) References Cited

U.S. PATENT DOCUMENTS

| | | | |
|---|---|---|---|
| 3,065,143 A | 11/1962 | Christenson et al. | 424/468 |
| 3,427,378 A | 2/1969 | Henderson et al. | 424/457 |
| 3,444,290 A | 5/1969 | Wai | 424/9.411 |
| 3,458,622 A | 7/1969 | Hill | 424/468 |
| 3,555,151 A | 1/1971 | Kaplan et al. | 424/686 |
| 3,574,820 A | 4/1971 | Johnson et al. | 424/423 |
| 3,932,407 A | 1/1976 | Beverung, Jr. et al. | 544/250 |
| 3,976,764 A | 8/1976 | Watanabe et al. | 424/451 |
| 4,105,776 A | 8/1978 | Ondetti et al. | 514/423 |
| 4,123,403 A | 10/1978 | Warner et al. | 523/313 |
| 4,140,755 A | 2/1979 | Sheth et al. | 424/472 |
| 4,146,718 A | 3/1979 | Jenks et al. | 544/292 |
| 4,173,626 A | 11/1979 | Dempski et al. | 424/462 |
| 4,208,521 A | 6/1980 | Crenshaw et al. | 544/250 |
| 4,248,857 A | 2/1981 | DeNeale et al. | 424/493 |
| 4,252,786 A | 2/1981 | Weiss et al. | 424/495 |
| 4,258,030 A | 3/1981 | Sasaki et al. | 424/94.63 |
| 4,259,314 A | 3/1981 | Lowey | 424/469 |
| 4,302,386 A | 11/1981 | Stevens | 530/322 |
| 4,309,404 A | 1/1982 | DeNeale et al. | 424/489 |
| 4,309,405 A | 1/1982 | Guley et al. | 424/493 |
| 4,316,906 A | 2/1982 | Ondetti et al. | 514/422 |
| 4,337,201 A | 6/1982 | Petrillo, Jr. | 548/413 |
| 4,344,949 A | 8/1982 | Hoefle et al. | 514/307 |
| 4,357,330 A | 11/1982 | Fleming, Jr. et al. | 514/161 |

(Continued)

FOREIGN PATENT DOCUMENTS

| | | |
|---|---|---|
| EP | 0 253 310 | 10/1994 |
| EP | 0792647 | 9/1997 |

(Continued)

OTHER PUBLICATIONS

Ho, H-O.; Su, H-L.; Tsai, T.; Sheu, M-T. "The preparation and characterization of solid dispersions on pellets using a fluidized-bed system" International Journal of Pharmaceutics 1996, 139, 223-229.*

Hecq, J.; Deleers, M.; Fanara, D.; Vranckz, H.; Amighi, K. "Preparation and characterization of nanocrystals for solubility and dissolution rate enhancement of nifedipine" Int J Pharm 2005, 299, 167-177.*

Letter/Written Disclosure of the Supplemental Information Disclosure Statement for the above-referenced application, mailed on Jul. 2, 2013, 2 pages.

International Preliminary Report on Patentability, issued Nov. 17, 2010, in connection with corresponding International Patent Application No. PCT/US2009/003632, 12 pages.

(Continued)

*Primary Examiner* — Sean Basquill
*Assistant Examiner* — Andrew S Rosenthal
(74) *Attorney, Agent, or Firm* — Nelson Mullins Riley & Scarborough LLP; Jane E. Remillard, Esq.; Cynthia L. Kanik

(57) ABSTRACT

Provided are prophylactic and therapeutic methods of treatment of subjects for the purpose of inhibiting vaso-occlusive events, including embolism, by administering agents, including anagrelide and anagrelide derivatives, which reduce the number of circulating platelets to low normal or to below normal levels. Methods and pharmaceutical preparations comprising such agents are provided.

43 Claims, 5 Drawing Sheets

(56) References Cited

U.S. PATENT DOCUMENTS

| | | | |
|---|---|---|---|
| 4,374,829 A | 2/1983 | Harris et al. | 514/21 |
| 4,410,520 A | 10/1983 | Watthey | 514/212.07 |
| 4,444,777 A | 4/1984 | Fleming, Jr. et al. | 514/267 |
| RE31,617 E | 6/1984 | Beverung, Jr. et al. | 544/250 |
| 4,452,775 A | 6/1984 | Kent | 424/425 |
| 4,502,888 A | 3/1985 | Leng et al. | 106/189.1 |
| 4,508,729 A | 4/1985 | Vincent et al. | 514/419 |
| 4,512,924 A | 4/1985 | Attwood et al. | 540/500 |
| 4,568,676 A | 2/1986 | Smith | 514/262.1 |
| 4,578,079 A | 3/1986 | Roslahti et al. | 623/23.76 |
| 4,587,258 A | 5/1986 | Gold et al. | 514/412 |
| 4,595,418 A | 6/1986 | Yoshino | 127/30 |
| 4,614,517 A | 9/1986 | Ruoslahti et al. | 530/330 |
| 4,661,471 A | 4/1987 | Hawiger et al. | 514/13 |
| 4,756,911 A | 7/1988 | Drost et al. | 424/468 |
| 4,772,684 A | 9/1988 | Brunck et al. | 530/316 |
| 4,780,401 A | 10/1988 | Heusser et al. | 424/146.1 |
| 4,792,525 A | 12/1988 | Roslahti et al. | 435/402 |
| 4,847,276 A | 7/1989 | Yarrington | 514/384 |
| 4,851,345 A | 7/1989 | Hayashi et al. | 435/215 |
| 5,004,609 A | 4/1991 | Hayashi et al. | 424/94.3 |
| 5,033,252 A | 7/1991 | Carter | 53/425 |
| 5,047,248 A | 9/1991 | Calanchi et al. | 424/485 |
| 5,047,428 A | 9/1991 | Itoh et al. | 514/562 |
| 5,052,558 A | 10/1991 | Carter | 206/439 |
| 5,064,825 A | 11/1991 | Chakravarty et al. | 514/221 |
| 5,073,566 A | 12/1991 | Lifer et al. | 514/381 |
| 5,081,127 A | 1/1992 | Carini et al. | 514/359 |
| 5,085,992 A | 2/1992 | Chen et al. | 435/119 |
| 5,087,634 A | 2/1992 | Reitz et al. | 514/381 |
| 5,091,187 A | 2/1992 | Haynes | 424/450 |
| 5,091,188 A | 2/1992 | Haynes | 424/450 |
| 5,098,840 A | 3/1992 | Kasai et al. | 435/215 |
| 5,145,683 A | 9/1992 | Rhodes | 424/451 |
| 5,145,684 A | 9/1992 | Liversidge et al. | 424/489 |
| 5,185,323 A | 2/1993 | Gewirtz | 514/12 |
| 5,302,401 A | 4/1994 | Liversidge et al. | 424/501 |
| 5,306,709 A | 4/1994 | Gewirtz | 514/12 |
| 5,318,899 A | 6/1994 | Scarborough et al. | 435/69.6 |
| 5,323,907 A | 6/1994 | Kalvelage | 206/531 |
| 5,342,626 A | 8/1994 | Winston et al. | 424/461 |
| 5,446,070 A | 8/1995 | Mantelle | 514/772.6 |
| 5,470,583 A | 11/1995 | Na et al. | 424/489 |
| 5,472,944 A | 12/1995 | Gewirtz et al. | 514/12 |
| 5,474,995 A | 12/1995 | Ducharme et al. | 514/241 |
| 5,521,213 A | 5/1996 | Prasit et al. | 514/443 |
| 5,536,752 A | 7/1996 | Ducharme et al. | 514/602 |
| 5,552,422 A | 9/1996 | Gauthier et al. | 514/368 |
| 5,604,253 A | 2/1997 | Lau et al. | 514/415 |
| 5,604,260 A | 2/1997 | Guay et al. | 514/605 |
| 5,612,053 A | 3/1997 | Baichwal et al. | 424/440 |
| 5,614,218 A | 3/1997 | Olsson et al. | 424/456 |
| 5,639,780 A | 6/1997 | Lau et al. | 514/419 |
| 5,643,933 A | 7/1997 | Talley et al. | 514/372 |
| 5,677,318 A | 10/1997 | Lau | 514/361 |
| 5,686,571 A | 11/1997 | Scarborough et al. | 530/330 |
| 5,691,374 A | 11/1997 | Black et al. | 514/473 |
| 5,698,584 A | 12/1997 | Black et al. | 514/462 |
| 5,710,140 A | 1/1998 | Ducharme et al. | 514/91 |
| 5,733,909 A | 3/1998 | Black et al. | 514/238.8 |
| 5,753,702 A | 5/1998 | Bednar et al. | 514/552 |
| 5,789,413 A | 8/1998 | Black et al. | 514/252.01 |
| 5,798,246 A | 8/1998 | Au-Young et al. | 435/196 |
| 5,801,245 A | 9/1998 | Lang | 544/250 |
| 5,817,700 A | 10/1998 | Dube et al. | 514/768 |
| 5,849,943 A | 12/1998 | Atkinson et al. | 560/8 |
| 5,861,419 A | 1/1999 | Dube et al. | 514/334 |
| 5,871,776 A | 2/1999 | Mehta | 424/462 |
| 5,877,224 A | 3/1999 | Brocchini et al. | 514/772.2 |
| 5,922,742 A | 7/1999 | Black et al. | 514/345 |
| 5,925,631 A | 7/1999 | Black et al. | 514/183 |
| 5,972,366 A | 10/1999 | Haynes et al. | 424/422 |
| 6,083,518 A | 7/2000 | Lindahl | 424/405 |
| 6,083,534 A | 7/2000 | Wallach et al. | 424/484 |
| 6,200,989 B1 | 3/2001 | De Cillis et al. | 514/320 |
| 6,214,376 B1 | 4/2001 | Gennadios | 424/451 |
| 6,287,599 B1 | 9/2001 | Burnside et al. | 424/468 |
| 6,376,242 B1 | 4/2002 | Hanson | 435/334 |
| 6,388,073 B1 | 5/2002 | Lang et al. | 544/250 |
| 6,451,609 B1 | 9/2002 | Xu et al. | 436/64 |
| 6,506,410 B1 | 1/2003 | Park et al. | 424/489 |
| 6,585,995 B1 * | 7/2003 | Hanson | 424/424 |
| 6,596,298 B2 | 7/2003 | Leung et al. | 424/435 |
| 6,656,493 B2 | 12/2003 | Dzija et al. | 424/439 |
| 6,682,761 B2 | 1/2004 | Pace et al. | 424/489 |
| 6,923,981 B2 | 8/2005 | Leung et al. | 424/439 |
| 6,994,283 B1 | 2/2006 | Yuki et al. | 241/5 |
| 7,005,454 B2 | 2/2006 | Brocchini et al. | 514/772.1 |
| 7,022,521 B2 | 4/2006 | Hanson | 435/334 |
| 7,048,945 B2 * | 5/2006 | Percel et al. | 424/471 |
| 7,070,972 B1 | 7/2006 | O'Shea et al. | 435/194 |
| 7,090,986 B2 | 8/2006 | Strittmatter et al. | 435/7.1 |
| 7,101,840 B2 | 9/2006 | Brocchini et al. | 514/2 |
| 7,241,411 B2 | 7/2007 | Berry et al. | 264/160 |
| 2001/0019446 A1 | 9/2001 | Hartung | 359/326 |
| 2002/0119144 A1 | 8/2002 | Hanson | 424/94.63 |
| 2003/0068384 A1 | 4/2003 | Brocchini et al. | 424/501 |
| 2003/0158261 A1 | 8/2003 | Burnside et al. | 514/617 |
| 2003/0232389 A1 | 12/2003 | Wilhelm et al. | 435/7.1 |
| 2004/0062800 A1 | 4/2004 | Burnside et al. | 424/468 |
| 2004/0087035 A1 | 5/2004 | Hanson | 436/514 |
| 2004/0087486 A1 | 5/2004 | Hanson | 514/2 |
| 2005/0118268 A1 | 6/2005 | Percel et al. | 424/471 |
| 2005/0214371 A1 | 9/2005 | Di Capua et al. | 424/472 |
| 2005/0228001 A1 | 10/2005 | Hanson | 424/457 |
| 2006/0052601 A1 | 3/2006 | Franklin | 544/250 |
| 2007/0148211 A1 | 6/2007 | Altreuter et al. | 424/441 |
| 2007/0202108 A1 | 8/2007 | Tandon et al. | 424/146.1 |
| 2008/0113024 A1 | 5/2008 | Hanson | 424/486 |
| 2009/0220611 A1 | 9/2009 | Dargelas et al. | 424/495 |
| 2009/0324710 A1 | 12/2009 | Glidden et al. | 424/451 |
| 2010/0008913 A1 | 1/2010 | Hanson | 424/133.1 |

FOREIGN PATENT DOCUMENTS

| | | |
|---|---|---|
| EP | 1 004 674 | 5/2000 |
| GB | 2460915 | 5/2011 |
| GB | 2462022 | 5/2011 |
| WO | WO 95/00501 | 1/1995 |
| WO | WO 95/18799 | 7/1995 |
| WO | WO 97/04744 | 2/1997 |
| WO | WO 98/11896 | 3/1998 |
| WO | WO 01/21163 | 3/2001 |
| WO | WO 01/21259 | 3/2001 |
| WO | WO 01/37808 | 5/2001 |
| WO | WO 02/06538 | 1/2002 |
| WO | WO 02/08228 | 1/2002 |
| WO | WO 03/020243 | 3/2003 |
| WO | WO 03/090723 | 11/2003 |
| WO | WO 2004/000280 | 12/2003 |
| WO | WO 2004/049095 | 6/2004 |
| WO | WO 2007/018943 | 2/2007 |
| WO | WO 2007/036671 | 4/2007 |
| WO | WO 2007/089768 | 8/2007 |
| WO | WO 2008/065444 | 6/2008 |
| WO | WO 2008/069546 | 6/2008 |
| WO | WO 2008/090569 | 7/2008 |
| WO | WO 2009/035562 | 3/2009 |
| WO | WO 2010/005480 | 1/2010 |

OTHER PUBLICATIONS

Examination Report, issued Oct. 24, 2012, in connection with corresponding corresponding European Patent Application No. 09788803.6, 4 pages.

Translation of Official Action, issued Oct. 30, 2012, in connection with corresponding Israeli Patent Application No. 209977, 3 pages.

Letter/Written Disclosure of the Information Disclosure Statement for the above-referenced application, mailed on Oct. 18, 2012, 2 pages.

"Alendronate Sodium," Pharmacopeial Forum 24(1):5438-5441 (1998).

"Anagrelide," The Merck Index, 13th Edition, Whitehouse Station, New Jersey: Merck Research Laboratories, entry 629, p. 105 (2001).

(56) References Cited

OTHER PUBLICATIONS

A.D.A.M. Medical Encyclopedia, U.S. National Library of Medicine, "Thrombocytopenia," Published on Mar. 14, 2012 [online][retrieved on Jan. 14, 2012] Retrieved from:<URL: ncbi.nlm.nih.gov/pubmedhealth/PMH0001612 [2 pages].
Andersson et al., "Leukemic transformation of essential thrombocythemia without previous cytoreductive treatment," Ann Hematol 79:40-42 (2000).
Andreasen et al., "The urokinase-type plasminogen activator system in cancer metastasis: a review," International Journal of Cancer 72:1-22 (1997).
Antithrombotic Trialists' Collaboration, "Collaborative meta-analysis of randomised trials of antiplatelet therapy for prevention of death, myocardial infarction, and stroke in high risk patients," BMJ 324:71-86 (2002).
Balan, K. and M. Critchley, "Outcome of 259 patients with primary proliferative polycythaemia (PPP) and idiopathic thrombocythaemia (IT) treated in a regional nuclear medicine department with phosphorus-32—a 15 year review," Br J Radiol 70:1169-1173 (1997).
Barbui et al., "Practice guidelines for the therapy of essential thrombocythemia. A statement from the Italian Society of Hematology, the Italian Society of Experimental Hematology and the Italian Group for Bone Marrow Transplantation," Haematologica 89(2):215-232 (2004).
Barbui, T. and G. Finazzi, "When and how to treat essential thrombocythemia," N Engl J Med 353(1):85-86 (2005).
Beavo, J., "Cyclic nucleotide phosphodiesterases: functional implications of multiple isoforms," Physiological Reviews 75: 725-748 (1995).
Bio Vascular Inc. Cardiovascular Risk Reduction, BVI007 Product Profile found at: www.biovascularinc.com/cardio.html [3 pages] [accessed on Aug. 18, 2009].
Birgegard, "Long-term management of thrombocytosis in essential thrombocythaemia," Ann. Hematol. 88:1-10 (2009).
Campbell et al., "Definition of subtypes of essential thrombocythaemia and relation to polycythaemia vera based on JAK2 V617F mutation status: a prospective study," Lancet 366:1945-1953 (2005).
CAPRIE Steering Committee, No authors listed, "A randomised, blinded, trial of clopidogrel versus aspirin in patients at risk of ischaemic events (CAPRIE). CAPRIE Steering Committee," Lancet 348: 1329-1339 (1996).
Chen et al., "Thrombospondin, a negative modulator of megakaryocytopoiesis," J Lab Clin Med 129:231-238 (1997).
Christoforidou et al., "Hydroxyurea and anagrelide combination therapy in patients with chronic myeloproliferative diseases resistant or intolerant to monotherapy," Acta Haematologica 120:195-198 (2008).
Cortelazzo et al., "Hydroxyurea for patients with essential thrombocythemia and a high risk of thrombosis," New Eng J Med 332(17):1132-1136 (1995).
Cortelazzo et al., Incidence and risk factors for thrombotic complications in a historical cohort of 100 patients with essential thrombocythemia, J Clin Oncol 8:556-562 (1990).
D'Adda et al., "The combined use of hydroxyurea and anagrelide allows satisfactory hematologic control in patients with chronic myeloproliferative disorders and thrombocytoses: a report on 13 patients with poor tolerance to hydroxyurea monotherapy," Leuk. Lymph. 49(11):2216-2218 (2008).
Dailymed, "AGRYLIN® (anagrelide hydrochloride) Capsules," Revised May 2006 [online][retrieved on Jan. 17, 2012] Retrieved from:<URL:dailymed.nlm.hih.gov/dailymed/archives/fdaDruginfo.cfm?archiveid=3127 [15 pages].
De Stefano et al., "Recurrent thrombosis in patients with polycythemia vera and essential thrombocythemia: incidence, risk factors, and effect of treatments," Haematologica 93(3):372-380 (2008).
Fenaux et al., "Clinical course of essential thrombocythemia in 147 cases," Cancer 66:549-556 (1990).
Finazzi et al., "Risk of thrombosis in patients with essential thrombocythemia and polycythemia vera according to JAK2 V617F mutation status," Haematologica 92:135-136 (2007).
Finazzi et al., "Second malignancies in patients with essential thrombocythaemia treated with busulphan and hydroxyurea: long-term follow-up of a randomized clinical trial ," Br J Haematol 110:577-583 (2000).
Finazzi, G. and C. Harrison, "Essential thrombocythemia," Seminars in Hematology 42(4):230-238 (2005).
Finazzi, G. and T. Barbui, "How I treat patients with polycythemia vera," Blood 109(12):5104-5111 (2007).
Finazzi, G. and T. Barbui, "Risk-adapted therapy in essential thrombocythemia and polycythemia vera," Blood Reviews 19(5):243-252 (2005).
Fruchtman et al., "Anagrelide: analysis of long-term efficacy, safety and leukemogenic potential in myeloproliferative disorders," Leuk Res. 29:481-491 (2005).
Gan et al., "Echistatin. A potent platelet aggregation inhibitor from the venom of the viper, *Echis carinatus*," J Biol Chem 263:19827-19832 (1988).
George, "Platelets on the web: Drug-induced thrombocytopenia, database from single case report, literature review," The University of Oklahoma Health Sciences Center, [online][retrieved on Jan. 30, 2012] Retrieved from:<URL:ouhsc.edu/platelets/InternetPostingLitSingleFrames2_18_11.htm [35 pages].
Gerschutz, G. and D. Bhatt, "The CURE trial: using clopidogrel in acute coronary syndromes without ST-segment elevation," Cleveland Clinic J Med 69:377-385 (2002).
Gisslinger, H., "Update on diagnosis and management of essential thrombocythemia," Semin Thromb Hemost 32: 430-436 (2006).
Golan et al., Principles of Pharmacology: The Pathophysiologic Basis of Drug Therapy, 2nd ed., (paperback, p. 377) (2008).
Grant, S., "Putting tubby on the MAP," Nat. Genet. 30(4):347-348 (2002).
Harrison et al., "Hydroxyurea compared with anagrelide in high-risk essential thrombocythemia," New Engl. J. Med. 353:33-45 (2005).
Hecq et al., "Preparation and characterization of nanocrystals for solubility and dissolution rate enhancement of nifedipine," Int. J. Pharmaceutics 299:167-177 (2005).
Ho et al., "The preparation and characterization of solid dispersions on pellets using a fluidized-bed system," Int. J. Pharmaceutics 139:223-229 (1996).
Huang et al., "Trigramin. A low molecular weight peptide inhibiting fibrinogen interaction with platelet receptors expressed on glycoprotein IIb-IIIa complex." J Biol Chem 262:16157-16163 (1987).
Huang et al., "Trigramin: primary structure and its inhibition of von Willebrand factor binding to glycoprotein IIb/IIIa complex on human platelets," Biochemistry 28:661-666 (1989).
Idiopathic Myelofibrosis, published by The Leukemic & Lymphoma Society, 14:1-9 (2007).
IUPAC-IUB Commission on Biochemical Nomenclature—Abbreviated nomenclature of synthetic polypeptides(Polymerized Amino Acids)—Revised Recommendations(1971), Biochem. 11(5):942-944 (1972).
Jneid et al., "Aspirin and clopidogrel in acute coronary syndromes: therapeutic insights from the CURE study," Arch Intern Med. 163:1145-1153 (2003).
Jones et al., "Inhibitors of cyclic AMP phosphodiesterase. 1. Analogues of cilostamide and anagrelide," J Med Chem 30:295-303 (1987).
Kannel, W. and D. McGee, "Diabetes and cardiovascular risk fctors: the Framingham study," Circulation 59:8-13 (1979).
Kiroglu et al., "Nasal obstruction as a common side-effect of sildenafil citrate," Tohoku Journal of Experimental Medicine 208(3):251-254 (2006).
Kumar et al., "Phosphodiesterase III inhibitors: latest addition to anaesthesiologist's armamentarium," J Anaesth Clin Pharmacol 20(3):227-237 (2004).
Lengfelder et al., Diagnosis and therapy of polycythemia vera, Seminars in Thrombosis and Hemostatis 32(3): 267-275 (2006).

(56) References Cited

OTHER PUBLICATIONS

Lincoln, T., "Cyclic GMP and phosphodiesterase 5 inhibitor therapies: what's on the horizon?" Molecular Pharmacology 66(1):11-13 (2004).
Lopez et al., "The global burden of disease, 1990-2020," Nat Med 4:1241-1243 (1998).
Ludwig et al., "Interferon-alfa corrects thrombocytosis in patients with myeloproliferative disorders," Cancer Immunol Immunother 25:266-73 (1987).
Mazzucconi et al., "Pipobroman therapy of essential thrombocythemia," Scand J Haematol 37:306-9 (1986).
McMullin et al., "Guidelines for the diagnosis, investigation and management of polycythaemia/erythrocytosis," Br J Haem 130(2):174-175 (2005).
Meanwell et al., "Inhibitors of blood platelet cAMP phosphodiesterase. 2. Structure-activity relationships associated with 1,3-dihydro-2H-imidazo[4,5-b]quinolin-2-ones substituted with functionalized side chains," J. Med. Chem 35: 2672-87 (1992).
Morita et al., "Identification and characterization of a collagen-induced platelet aggregation inhibitor, triplatin, from salivary glands of the assassin bug, *Triatoma infestans*," FEBS Journal 273:2955-2962 (2006).
Najean, Y. and J. Rain, "Treatment of polycythemia vera: the use of hydroxyurea and pipobroman in 292 patients under the age of 65 years," Blood 90(9): 3370-3377 (1997).
Nikolsky et al., "Impact of baseline platelet count in patients undergoing primary percutaneous coronary intervention in acute myocardial infarction (from the CADILLAC trial)," Am J Cardiol 99(8):1055-1061 (2007).
Nolan et al., "Acute effects of intravenous phosphodiesterase inhibition in chronic heart failure: simultaneous pre- and afterload reduction with a single agent," Int J Cardiol. 35:343-349 (1992).
Nordic MPD Study Group, "Guidelines for the diagnosis and treatment of patients with polycythemia vera, essential thrombocythemia and idiopathic myelofibrosis," 60 pages (2007).
Pescatore, S. and C. Lindley, "Anagrelide: a novel agent for the treatment of myeloproliferative disorders," Expert Opin Pharmacother 1(3):537-546 (2000).
Petrides et al., "Pharmacokinetics, bioequivalence, tolerability, and effects on platelet counts of two formulations of anagrelide in healthy volunteers and patients with thrombocythemia associated with chronic myeloproliferation," Clin. Ther. 31:386-398 (2009).
Petrides, P., "Anagrelide: a decade of clinical experience with its use for the treatment of primary thrombocythaemia," Expert Opin Pharmacother 5(8):1781-1798 (2004).
Petrides, P., "Anagrelide: what was new in 2004 and 2005?" Semin Thromb Hemost. 32(4):399-408 (2006).
Pletal (cilostazol) Product Monograph, Otsuka Pharmaceutical Europe Ltd., 36 pages (Jan. 2003).
Rasenack et al., "Preparation of microcrystals by in situ micronization," Powder Technology, vols. 143-144, pp. 291-296 (2004).
Samuelsson et al., "A phase II trial of pegylated interferon alpha-2b therapy for polycythemia vera and essential thrombocythemia: feasibility, clinical and biologic effects, and impact on quality of life," Cancer 106(11):2397-2405 (2006).
Shire data on file with the FDA, entitled Attachment G: Evidence for the primary role of anagrelide's major metabolite, 3-hydroxy anagrelide in the drug's clinical activity.
Sloan, A., "The normal platelet count in Man," J. Clin. Path. 4:37-46 (1951).
Stone et al. "Comparison of angioplasty with stenting, with or without abciximab, in acute myocardial infarction," N Eng J Med 346: 957-966 (2002).
Tefferi, A. and J. Vardiman, "Classification and diagnosis of myeloproliferative neoplasms: the 2008 World Health Organization criteria and point-of-care diagnostic algorithms," Leukemia 22:14-22 (2008).
Tefferi, A., "Myelofibrosis with Myeloid Metaplasia," N. Engl. J. Med. 342:1255-1265 (2000).
Thaulow et al., "Blood platelet count and function are related to total and cardiovascular death in apparently healthy men," Circulation 84(2): 613-617 (1991).
Thompson, W., "Cyclic nucleotide phosphodiesterases: pharmacology, biochemistry and function," Pharmacol Ther. 51(1):13-33 (1991).
Turgeon, M., Clinical Hematology: Theory and Procedures, 4th ed., Philidelphia: Lippincott Williams & Wilkins, p. 313. (2005).
Van de Pette et al., "Primary thrombocythaemia treated with busulphan," British Journal of Haematology, 62:229-37 (1986).
Vannucchi et al., "Prospective identification of high-risk polycythemia vera patients based on JAK2(V617F) allele burden," Leukemia 21(9):1952-1959 (2007).
Vehring et al., "Pharmaceutical particle engineering via spray drying," Pharm Res. 25(5):999-1022 (2008).
Visentin et al., "Drug induced thrombocytopenia," Hematol. Oncol. Clin. North Am. 21(4):685-vi, 11 pages (2007).
Vitezic, D., "A risk-benefit assessment of sildenafil in the treatment of erectile dysfunction," Drug Saf. 24(4):255-265 (2001).
Wagstaff, A. and G. Keating, "Anagrelide: a review of its use in the management of essential thrombocythaemia," Drugs 66(1):111-131 (2006).
Wong et at., "Nonpeptide angiotensin II receptor antagonists. I. Pharmacological characterization of 2-n-butyl-4-chloro-1-(2-chlorobenzyl)imidazole-5-acetic acid, sodium salt (S-8307)," J. Pharmacol. Exp. Ther. 247(1): 1-7 (1988).
Yasuda et al., "Monoclonal antibody against the platelet glycoprotein (GP) IIb/IIIa receptor prevents coronary artery reocclusion after reperfusion with recombinant tissue-type plasminogen activator in dogs," J Clin Invest 81(4):1284-1291 (1988).
Yeager et al., "Effects of cyclophosphamide on murine bone marrow and splenic megakaryocyte-CFC, granulocyte-macrophage-CFC, and peripheral blood cell levels," J. Cell. Physiol. 112(2): 222-8 (1982).
Yusuf et al., "Effects of clopidogrel in addition to aspirin in patients with acute coronary syndromes without ST-segment elevation," N Engl J Med. 345(7):494-502 (2001).
Office Action, issued Oct. 12, 2006, in connection with related U.S. Appl. No. 10/603,401, 9 pages.
Office Action, issued Oct. 29, 2007, in connection with related U.S. Appl. No. 11/127,544, 9 pages.
Office Action, issued Feb. 7, 2008, in connection with related U.S. Appl. No. 11/127,544, 8 pages.
Office Action, issued Jun. 23, 2008, in connection with related U.S. Appl. No. 11/127,544, 13 pages.
Office Action, issued Feb. 24, 2009, in connection with related U.S. Appl. No. 11/127,544, 11 pages.
Combined Search and Examination Report, issued Jul. 31, 2009, in connection with corresponding United Kingdom Application No. GB 0905567.4, 6 pages.
Office Action, issued Aug. 19, 2009, in connection with related U.S. Appl. No. 11/127,544, 9 pages.
Examination Report, issued Feb. 8, 2010, in connection with corresponding United Kingdom Application No. GB 0905567.4, 3 pages.
International Search Report and Written Opinion, issued Apr. 1, 2010, in connection with International Patent Application No. PCT/US2009/003632, 19 pages.
Examination Report, issued May 11, 2010, in connection with corresponding United Kingdom Application No. GB 0905567.4, 3 pages.
Translation of Official Action, issued Sep. 14, 2010, in connection with related Japanese Application No. 2001-524681, 3 pages.
Restriction Requirement, issued Feb. 15, 2011, in connection with related U.S. Appl. No. 12/008,204, 6 pages.
Examination Report, issued Feb. 15, 2011, in connection with corresponding European Patent Application No. 09788803.6, 2 pages.
Office Action, issued Apr. 15, 2011, in connection with related U.S. Appl. No. 12/460,712, 10 pages.
Restriction Requirement, issued Sep. 9, 2011, in connection with corresponding U.S. Appl. No. 12/456,443, 11 pages.
Response to Restriction Requirement, submitted Oct. 7, 2011, in connection with corresponding U.S. Appl. No. 12/456,443, 19 pages.
Office Action, issued Jan. 20, 2012, in connection with related U.S. Appl. No. 12/456,443, 31 pages.
Office Action and translation, issued Feb. 21, 2012, in connection with corresponding Chinese Application Serial No. 20098131941.6, 7 pages.
Notice of Allowance, issued Jun. 21, 2012, in connection with related U.S. Appl. No. 11/127,544, 8 pages.

\* cited by examiner

CONTROLLED RELEASE COMPOSITIONS OF AGENTS THAT REDUCE CIRCULATING LEVELS OF PLATELETS AND METHODS THEREFOR

RELATED APPLICATIONS

This application is a continuation of co-pending U.S. application Ser. No. 12/456,443, filed Jun. 16, 2009, entitled "CONTROLLED RELEASE COMPOSITIONS OF AGENTS THAT REDUCE CIRCULATING LEVELS OF PLATELETS AND METHODS THEREFOR," which claims benefit of priority is claimed under 35 U.S.C. §119(e) to U.S. Provisional Application Ser. No. 61/132,429, filed Jun. 16, 2008, entitled "CONTROLLED RELEASE COMPOSITIONS OF AGENTS THAT REDUCE CIRCULATING LEVELS OF PLATELETS AND METHODS THEREFOR" and U.S. Provisional Application Ser. No. 61/209,056, filed Mar. 2, 2009, entitled "CONTROLLED RELEASE COMPOSITIONS OF AGENTS THAT REDUCE CIRCULATING LEVELS OF PLATELETS AND METHODS THEREFOR," each to Paul F. Glidden, Alison J. Pilgrim and Stephen R. Hanson.; and to United Kingdom Patent Application Serial No 09 05567.4, filed Mar. 31, 2009, entitled "CONTROLLED RELEASE COMPOSITIONS OF AGENTS THAT REDUCE CIRCULATING LEVELS OF PLATELETS AND METHODS THEREFOR," filed Mar. 31, 2009.

This application is related International Application No. PCT/US2009/003632, filed Jun. 16, 2009, entitled "CONTROLLED RELEASE COMPOSITIONS OF AGENTS THAT REDUCE CIRCULATING LEVELS OF PLATELETS AND METHODS THEREFOR," which also claims priority to U.S. Provisional Application Ser. Nos. 61/132,429 and 61/209,056 and United Kingdom Patent Application Serial No 09 05567.4.

The subject matter of each of the above-referenced applications is incorporated by reference in its entirety.

FIELD OF THE INVENTION

Compositions and methods for reducing circulating platelet number in a subject and for the treatment and/or prevention of platelet-related conditions, diseases and/or disorders or other diseases and disorders are provided.

BACKGROUND

Conditions resulting from thrombotic or thromboembolic events are leading causes of illness and death in adults in western civilization. Platelets play a role in the etiology of several thrombotic and other vaso-occlusive disorders. A great deal of effort and monetary resources have been directed towards understanding the mechanisms involved in vascular occlusive diseases involving thrombotic or thromboembolic events. These efforts have yielded a number therapeutic agents. Notwithstanding the effort and financial resources that have been invested, these conditions still account for the vast majority of illness and death in the adult populations of developed nations. Thus, a need exists for compositions and methods for treatment and/or prevention of platelet related conditions or disorders, including hematological proliferative disorders, myeloproliferative disorders and thrombotic and other vaso-occlusive disorders. Accordingly, among the objects herein, it is an object to provide compositions and methods for treatment and/or prevention of platelet related conditions or disorders, including hematological proliferative disorders, myeloproliferative disorders and thrombotic and other vaso-occlusive disorders.

SUMMARY

Provided herein are compositions and prophylactic and therapeutic methods for reducing circulating platelet number in a subject and for the treatment and/or prevention of platelet-related conditions, diseases and/or disorders or other diseases and disorders.

Provided herein is a composition that includes a solid support core of a substantially water soluble, swellable or insoluble material; an optional preparatory coat, where the preparatory coat is from 0-5% by weight of the composition; a substrate layer that includes a binder and 50 µg to 10 mg of microparticles of a platelet number reducing agent, where the platelet-reducing agent is present in a form that has a shelf stability of at least three months, the binder is present at a weight of 0.1-5% by weight of the composition and at least 90% of the microparticles are 25 microns or less; a release control component effective for controlled release of the platelet number reducing agent, where the release control component is present at a weight of 0.25-10% by weight of the composition; and an optional finishing coat and/or enteric coating, where the finishing coat and/or enteric coating is present at a weight of 0-10% by weight of the composition.

In some embodiments, the composition further includes a seal coat layer including a substantially water-soluble polymer on the substrate layer, where the seal coat is disposed between the substrate layer and the release control component and the seal coat reduces chemical interaction between the platelet reducing agent and the release control component and/or the platelet reducing agent and the optional finishing coat. In some embodiments, the seal coat, when present, is present at a weight of 0.1-10% by weight of the composition, particularly at a weight of 1-5% by weight of the composition.

Also provided are compositions that include (i) a solid support core of a substantially water soluble, swellable or insoluble material; (ii) an optional preparatory coat, where the preparatory coat is from 0-5% by weight of the composition; (iii) a substrate layer including a binder and 10 ng to 10 mg of microparticles of a platelet number reducing agent, where (a) the binder is present at a weight of 0.1-5% by weight of the composition, (b) at least 90% of the microparticles are 25 microns or less and (c) the platelet-reducing agent is in form that has a shelf stability of at least 3 months; (iv) a release control component effective for controlled release of the platelet number reducing agent, where the release control component is present at a weight of 0.25-10% by weight of the composition; (v) a seal coat layer that includes a substantially water-soluble polymer, where the seal coat is present at a weight of 0-10% by weight of the composition; and (vi) an optional finishing coat and/or enteric coating, where the finishing coat and/or enteric coating is present at a weight of 0-10% by weight of the composition; where the seal coat is disposed between the substrate layer and the release control component and the seal coat reduces chemical interaction between the platelet reducing agent and the release control component and/or the platelet reducing agent and the optional finishing coat.

The substrate layer can include from 10 ng to 10,000 µg of microparticles of a platelet number reducing agent. The amount of microparticles in the substrate layer can vary depending on the platelet reducing agent and can be present in an amount of between 50 µg to 5000 µg of microparticles, or 150 µg to 500 µg of microparticles or 200 µg to 400 µg of microparticles of a platelet number reducing agent. In some embodiments, the amount of platelet number reducing agent is in a range selected from among at or about 10 ng to at or about 100 ng, at or about 10 ng to at or about 250 ng, at or about 10 ng to at or about 500 ng, at or about 10 ng to at or about 100 ng, at or about 10 ng to at or about 1000 ng, at or about 10 ng to at or about 250 ng, at or about 25 ng to at or about 250 ng, at or about 50 ng to at or about 500 ng, at or about 75 ng to at or about 750 ng, at or about 100 ng to at or about 1000 ng, at or about 250 ng to at or about 2500 ng, at or about 500 ng to at or about 5000 ng, at or about 750 ng to at or about 7500 ng, at or about 1000 ng to at or about 10000 ng, at or about 1 µg to at or about 10 µg, at or about 2 µg to at or about 20 µg, at or about 5 µg to at or about 25 µg, at or about 10 µg to at or about 100 µg, at or about 100 µg to at or about 500 µg, at or about 500 µg to at or about 750 µg, at or about 725 µg to at or about 1000 µg, at or about 750 µg to at or about 1125 µg, at or about 800 µg to at or about 1200 µg, at or about 1000 µg to at or about 1500 µg, at or about 1250 µg to at or about 2500 µg, 50 µg to 10 mg, 1000 µg to 1 mg, 5000 µg to 5 mg, 1 mg to 5 mg, 0.5 mg to 1.5 mg and 0.25 mg to 1.25 mg. In some embodiments, at least 50% of the microparticles are 12 microns or less.

In some embodiments, the platelet number reducing agent is in a hydrated crystal form. In some embodiments, the platelet number reducing agent is in a monohydrate crystal form. In some embodiments, the hydrated crystal form of the platelet reducing agent has a shelf stability of at least 3 months, or at least 6 months or at least 12 months.

The binder in the substrate layer of the compositions provided herein is selected from among polyvinyl pyrrolidone, hydroxypropyl methylcellulose, hydroxypropyl cellulose, carboxymethyl cellulose, hydroxymethyl cellulose, gelatin, gum arabic, gellan gum, xanthan gum, carrageenan, polyethylene oxide, a polymethacrylate, a dextrin, and starch or starch derivatives or combinations thereof. In some embodiments, the binder in the substrate layer is hydroxypropyl methylcellulose, particularly a low molecular weight hydroxypropyl methyl cellulose. In other embodiments, the binder in the substrate layer is povidone.

The compositions provided herein include a solid support core. The solid support core can be made of any appropriate material. Exemplary solid support cores include spherical or spheroid granules, pellets or beads made of a material selected from among sugar, starch or derivatives thereof, alginate, gellan gum, a polyol or combinations thereof. In some embodiments, the solid support core is a non-pareil sugar sphere.

The substantially water-soluble polymer of the seal coat can include any film forming polymer that is substantially soluble in water. Exemplary substantially water-soluble polymers include povidone, hydroxy-propyl cellulose (HPC), hydroxypropyl methylcellulose (HPMC), carboxy methyl cellulose (CMC), gelatin, polyethylene oxide, gum arabic, dextrin, magnesium aluminum silicate, starch, a polymethacrylate and combinations thereof. In some embodiments, the substantially water-soluble polymer is HPMC, in particular a low molecular weight HPMC.

The compositions provided herein also allow the incorporation of a plasticizer without significantly reducing the stability of a dosage form containing a platelet reducing agent, such as anagrelide hydrochloride monohydrate. For example, provided herein is a composition where the release control component and/or the optional finishing layer includes a plasticizer and the seal coat layer reduces deleterious interactions between the platelet reducing agent and the plasticizer.

In the compositions provided herein, the release control component is present at a weight of 1-5% by weight of the composition. The release control component can include a film forming polymer. Exemplary film forming polymers include ethyl cellulose, hydroxypropyl cellulose, hydroxypropyl methyl cellulose or a mixture of two or more of such cellulose derivatives, polyvinyl acetate, povidone, cross-linked starch, cross-linked chitosan, cross-linked gelatin, cross-linked hyaluronic acid, cross-linked polyvinyl alcohol, cross-linked sodium carboxymethyl cellulose, cross-linked polyvinyl pyrrolidone, carboxypolymethylene, zein or combinations thereof, particularly ethyl cellulose or polyvinyl acetate or a combination of polyvinyl acetate and povidone.

The release control component of the compositions provided herein also can include a pore former. When present, a pore former is present at a weight of 0.1 to 10% by weight of the composition, particularly at a weight of at or about 0.25% to at or about 10% by weight of the composition. In some embodiments, the ratio of pore former to film-forming polymer in the release control component is from at or about 1:1 to at or about 1:12. In some embodiments, the ratio of pore former to film-forming polymer in the release control component is from at or about 1:2 to at or about 1:10. In some embodiments, the ratio of pore former to film-forming polymer in the release control component is at or about 1:3. In some compositions, the pore former is hydroxypropyl methylcellulose. In some compositions, the release control component contains at or about 60% to at or about 95% by weight of ethyl cellulose and at or about 40% to at or about 5% by weight of hydroxypropyl methylcellulose.

In the compositions provided herein, the platelet reducing agent is in a form that has a shelf stability of at least 3 months. In some embodiments, the platelet reducing agent is in a hydrated crystal form. In some embodiments, the platelet reducing agent is in a monohydrate crystal form. In some embodiments, the platelet reducing agent is a hydrated crystal form of anagrelide, 3-hydroxy anagrelide, a derivative or analog of anagrelide or a combination thereof.

Advantageous compositions provided herein include a substrate layer formed by a process that substantially maintains the hydrated crystal form of the platelet reducing agent. For example, provided herein are compositions where the platelet reducing agent is spray dried onto the solid support.

In some embodiments, a composition is provided where the composition has an effective moisture level of at or about 1% to at or about 10% by weight. The effective moisture is the moisture provided to the platelet reducing agent in a finished dosage form. The effective moisture level is sufficient to maintain the crystal water molecules in place so that the platelet reducing agent has a hydration level sufficient to maintain crystallinity of the platelet reducing agent particles. In some embodiments, a composition having a moisture content of between at or about 1% to at or about 3% provides an effective moisture that maintains a hydrated crystalline form of a platelet reducing agent.

In some embodiments, the platelet reducing agent has a moisture content between 0.5% and at or about 10%. In some embodiments, the platelet reducing agent has a moisture content between at or about 1% and at or about 8%. In some embodiments, the platelet reducing agent has a moisture content between at or about 2% and at or about 7%. In some embodiments, the platelet reducing agent has a moisture content between at or about 3% and at or about 6%.

In some embodiments, the compositions provided herein have a moisture content of at or about 0.5% to at or about 5% by weight. In some embodiments, the composition has a moisture content between at or about 1% and at or about 3%. In some embodiments, the compositions have a moisture content of 2% or less.

In some embodiments, the platelet number reducing agent is anagrelide. For example, provided herein are compositions where the substrate layer includes 10 ng to 10000 μg, such as 50 μg to 10000 μg of microparticles of anagrelide (measured on the basis of anagrelide free base). The anagrelide can be present as a free base or as a salt thereof, such as anagrelide hydrochloride. In some embodiments, the platelet reducing agent is anagrelide hydrochloride monohydrate. In some embodiments, the composition includes a platelet reducing agent in combination with hydroxyurea. In some embodiments, the composition includes a platelet reducing agent in combination with an agent selected from among platelet adhesion inhibitors, platelet aggregation inhibitors, plasminogen activator receptor (PAR) inhibitors, anti-inflammatory agents, anti-thrombotic agents, ADP receptor antagonists, platelet adhesion inhibitors, glycoprotein IIb/IIIa receptor inhibitors, cyclooxygenase inhibitors, fibrinolytic agents, lipid reducing agents, renin-angiotensin system inhibitors, antihypertensive agents, compounds that irreversibly bind to $P2Y_{12}$ receptors, chemotherapeutic anti-cancer drugs and alkylating agents such as hydroxyurea, thromboxane synthetase inhibitors, compounds that inhibit thromboxane $A_2$ formation, cell signaling molecules and JAK-2 inhibitors.

Also provided herein is a unit dosage form that includes spheroid granules, pellets or beads that include an amount from at or about 10 ng to at or about 10000 μg of a platelet-reducing agent having a shelf stability of at least 3 months. The spheroid granules, pellets or beads include a solid support core of a substantially water soluble, swellable or insoluble material; an optional preparatory coat; a substrate layer that includes the platelet number reducing agent; a seal coat layer that includes a substantially water-soluble polymer on the substrate layer; a release control component effective for controlled release of the platelet reducing agent; and an optional finishing coat and/or enteric coating. The unit dosage form provides a peak plasma level of the platelet number reducing agent at least 50% lower than produced by an immediate release formulation of the platelet number reducing agent, and the seal coat is disposed between the substrate layer and the release control component and reduces chemical interaction between the platelet reducing agent and the release control component and/or the platelet reducing agent and the optional finishing coat.

In some embodiments, the platelet number reducing agent in the unit dosage form is in a form that has a shelf stability of at least 3 months, particularly a shelf stability of 6 months or 12 months or more. The platelet number reducing agent can be present in a hydrated crystal form, such as a monohydrate crystal form. In one embodiment, the platelet number reducing agent is provided in the form of free flowing microparticles. The platelet number reducing agent can include any agent that reduces circulating platelets, such as anagrelide, 3-hydroxy anagrelide, an analog or derivative of anagrelide, and a pharmaceutically acceptable salt thereof. In some embodiments, the unit dosage form includes anagrelide hydrochloride monohydrate. Combinations of platelet reducing agents also can be included in the compositions, such as the unit dosage forms. In particular, the unit dosage form can include hydroxyurea in combination with anagrelide, 3-hydroxy anagrelide, an analog or derivative of anagrelide, and a pharmaceutically acceptable salt thereof. The hydroxyurea can be present in an amount of from 1 μg to 500 mg. The unit dosage form has a shelf stability of at least 3 months, particularly a shelf stability of 6 months or 12 months or more.

In the compositions provided herein, the spheroid granules, pellets or beads of the unit dosage form can be formed into a capsule, a tablet, a pill, a troche, a pastille, a dragée, a wafer, a caplet or a lozenge or dispersed in an elixir, a suspension, a syrup, or a dissolvable film or filled into a capsule.

The unit dosage forms provided herein can include an immediate release form of the platelet number reducing agent. The immediate release form of a platelet number reducing agent in the unit dosage form can include granules, pellets or beads that include an amount from at or about 10 ng to at or about 1000 μg of a platelet number reducing agent. In addition to the platelet reducing agent, the immediate release form of the platelet reducing agent includes a solid support core of a substantially water soluble, swellable or insoluble material; an optional preparatory coat; a substrate layer including the platelet number reducing agent; and an optional seal coat layer including a substantially water-soluble polymer on the substrate layer. The immediate release form of the platelet number reducing agent can be in the form of microparticles.

In unit dosage forms that include an immediate release form of the platelet number reducing agent, the immediate release form makes up 50% or less of the dosage form. In some embodiments, the immediate release form of the platelet number reducing agent makes up 25% or less of the dosage form, particularly 10% or less of the dosage form, such as 3% or less of the dosage form.

Also provided are methods for reducing platelet count in a subject. The methods include administering to a subject a controlled release composition of a platelet number reducing agent in a form that has a shelf stability of at least 3 months and the composition delivers an amount of the platelet number reducing agent effective to reduce platelet count in the subject by at least 10% of pre-treatment levels, where the controlled release composition does not overtly cause clinical symptoms that prevent or limit therapeutic use of the platelet number reducing agent. In some embodiments, the agent is in a hydrated crystal form, such as a monohydrate crystal form. In some embodiments, the hydrated crystal form of the platelet-reducing agent is substantially maintained for a shelf period of at least 3 months. In some embodiments, the hydrated crystal form of the platelet-reducing agent is substantially maintained for a shelf period of at least 6 months. In some embodiments, the hydrated crystal form of the platelet-reducing agent is substantially maintained for a shelf period of at least 12 months. The platelet number reducing agent used in the methods can include any agent that reduces circulating platelets, such as anagrelide, 3-hydroxy anagrelide, an analog or derivative of anagrelide, and a pharmaceutically acceptable salt thereof. In some embodiments, the method includes administering anagrelide hydrochloride monohydrate. Combinations of platelet reducing agents also can be used in the methods. In some methods, a combination of one or more platelet reducing agents and another therapeutic are administered. In some embodiments, the composition includes a platelet reducing agent in combination with an agent selected from among platelet adhesion inhibitors, platelet aggregation inhibitors, plasminogen activator receptor (PAR) inhibitors, anti-inflammatory agents, anti-thrombotic agents, ADP receptor antagonists, platelet adhesion inhibitors, glycoprotein IIb/IIIa receptor inhibitors, cyclooxygenase inhibitors, fibrinolytic agents, lipid reducing agents, renin-angiotensin system inhibitors, antihypertensive agents, compounds that irreversibly bind to $P2Y_{12}$ receptors, chemotherapeutic anti-cancer drugs and alkylating agents such as hydroxyurea, thromboxane synthetase inhibitors, compounds that inhibit thromboxane formation, cell signaling molecules and JAK-2 inhibitors. In particular, a combination of hydroxyurea with anagrelide, 3-hydroxy anagrelide, an analog or derivative of anagrelide, and a pharmaceutically acceptable salt thereof can be used in the methods.

Another embodiment provides a method for reducing platelet count in a subject, the method including administering to a subject a controlled release composition as described herein, where the composition delivers an amount of the platelet number reducing agent effective to reduce platelet count in the subject by at least 10% of pre-treatment levels, and the delivery of the platelet number reducing agent by the controlled release composition does not overtly cause clinical symptoms that prevent or limit therapeutic use of the platelet number reducing agent.

Also provided are compositions and methods for treatment and/or prevention of platelet related conditions or disorders, including hematological proliferative disorders, myeloproliferative disorders and thrombotic and vaso-occlusive disorders. Treatment is effected by reducing the number of circulating platelets in a subject.

The compositions provided herein are formulated to reduce platelet number but do not exhibit adverse reactions heretofore associated with such platelet number reducing agents and compositions thereof. To achieve this, the compositions provided herein are formulated and administered to inhibit thrombopoietin (TPO)-induced platelet production without inhibiting phosphodiesterase (PDE) activity to a clinically significant extent so that undesirable or observed side-effects and/or adverse reactions or clinical symptoms associated with inhibition of PDE activity is/are eliminated or reduced.

Provided herein are pharmaceutical compositions having the effect of a platelet number reducing agent, such as anagrelide, 3-OH anagrelide or an analog or derivative thereof, but exhibiting known clinical side effects thereof to a decreased degree if at all.

The compositions provided herein include a platelet number reducing agent that is released in an amount and at a rate that reduces platelet number in a subject without overtly causing clinical symptoms that prevent/limit therapeutic use of the platelet number reducing agent.

Provided herein are compositions that produce an optimal pharmacokinetic profile of a platelet number reducing agent, such as anagrelide, 3-OH anagrelide or analog or derivative thereof, having a reduced $C_{max}$ with respect to an immediate release formulation while maintaining an exposure sufficient to reduce circulating platelet number. Exemplary compositions provided herein release the platelet number reducing agent at a rate and in an amount sufficient to produce a $C_{max}$ equal to or less than 50%, including 45%, 40%, 35%, 30%, 25%, 20% and 15%, of an immediate release formulation of the platelet number reducing agent, and to produce an AUC equal to or more than 55%, including 56%, 57%, 58%, 59%, 60%, 65%, 70%, 75%, 80%, 85%, 90%, 95%, 100%, 105%, 110%, 115%, 120% and 125% of an immediate release formulation of the platelet number reducing agent.

Also provided are compositions that produce a pharmacokinetic profile of a platelet number reducing agent, such as anagrelide, 3-OH anagrelide or analog or derivative thereof, where the compositions have a reduced $C_{max}$ with respect to an immediate release formulation, and release the platelet number reducing agent in an amount and at a rate sufficient to reduce platelet number by inhibition of thrombopoietin (TPO)-induced platelet production but not sufficient to meaningfully inhibit phosphodiesterase (PDE) activity (e.g., not overtly causing adverse reactions or clinical symptoms associated with inhibition of PDE activity). The compositions result in a noticeable reduction in side effects or adverse events including effects associated with inhibition of PDE, such as PDE III and PDE V. Such compositions minimize or eliminate adverse events, such as those mediated through an increase in cellular cAMP and/or cGMP levels. The adverse events associated with administration of some platelet number reducing agents, such as anagrelide hydrochloride monohydrate, often lead to discontinuation of the drug as a therapeutic. Because the compositions provided herein minimize or eliminate such adverse events, the compositions provided herein enable platelet number reducing agents, such as anagrelide hydrochloride monohydrate, to be used in a larger population as a therapeutic agent, and minimizes discontinuation of therapy due to adverse events.

Also provided are compositions designed through a combination of formulation and dose to provide a platelet number reducing agent, such as anagrelide, 3-OH anagrelide or analog or derivative thereof, at a circulating concentration sufficient to inhibit megakaryocyte production of platelets but not sufficient to inhibit phosphodiesterase (PDE) activity, thereby minimizing or eliminating adverse events.

Also provided are compositions that increase the apparent half life of a platelet number reducing agent, such as anagrelide, 3-OH anagrelide or analog or derivative thereof, 2, 3, 4, 5, 6, 7, 8, 9, 10, 11, 12, 13, 14 or 15 or more fold.

Also provided are compositions that reduce the adverse event profile of a platelet number reducing agent, such as anagrelide, 3-OH anagrelide or analog or derivative thereof, by selectively producing a plasma level of the platelet number reducing agent that affects the TPO-induced platelet production but does not meaningfully affect (e.g., does not induce adverse reactions or clinical symptoms associated with) phosphodiesterase activity, such as adverse reactions or clinical symptoms associated with PDE III or PDE V activity.

Also provided are compositions that bifurcate the mechanisms of action of anagrelide and/or 3-OH anagrelide on phosphodiesterase and megakaryocytopoiesis.

The compositions provided herein include a dosage of a platelet number reducing agent, such as anagrelide, 3-OH anagrelide or an analog or derivative thereof, of at or about 10 ng to at or about 10000 ng. In some embodiments, the compositions include a dose of platelet number reducing agent selected from among of at or about 10 ng to at or about 100 ng, at or about 25 ng to at or about 250 ng, at or about 50 ng to at or about 500 ng, at or about 75 ng to at or about 750 ng, at or about 100 ng to at or about 1000 ng, at or about 250 ng to at or about 2500 ng, at or about 500 ng to at or about 5000 ng, at or about 750 ng to at or about 7500 ng and at or about 1000 ng to at or about 10000 ng.

In some embodiments, the compositions include a dose of platelet number reducing agent of at or about 50 μg to at or about 1000 μg. In some embodiments, the compositions include a dosage of 1000 μg or less. In some embodiments, the compositions include a dosage of a platelet number reducing agent of from about 100 μg or 100 μg to about 900 μg or 900 μg. In some embodiments, the compositions include a dosage of a platelet number reducing agent of from about 200 μg or 200 μg to about 800 μg or 800 μg. In some embodiments, the compositions include a dosage of a platelet number reducing agent of 50 μg, 100 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg or 1000 μg.

Also provided are compositions of a platelet number reducing agent, such as anagrelide, 3-OH anagrelide or analog or derivative thereof, that provide a $C_{max}$ that is 50%, 45%, 40%, 35%, 30%, 25%, 20% or 15% or less of an immediate release formulation.

Also provided are compositions of a platelet number reducing agent, such as anagrelide, 3-OH anagrelide or analog or derivative thereof, where $T_{max}$ is delayed by about 1 hour or 1 hour to about 8 hours or 8 hours, including 1, 2, 3, 4, 5, 6, 7 or 8 hours.

Also provided are compositions of a platelet number reducing agent, such as anagrelide, 3-OH anagrelide or analog or derivative thereof, that provide an exposure in serum of the agent of at least 24 hours, or at least 36 hours, or from at or about 8 to at about 48 hours, e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours.

Also provided are controlled release compositions that include an amount of an agent that reduces circulating platelet numbers effective to reduce circulating platelet number in a subject in a delivery form formulated for release in an amount and at a rate that provides a $C_{max}$ that is 50% or less of an immediate release formulation of the platelet number reducing agent while maintaining total exposure sufficient to reduce platelet number. In some embodiments, the $C_{max}$ is, 45%, 40%, 35%, 30%, 25%, 20% or 15% or less of an immediate release formulation of the platelet-reducing agent. In some embodiments, the area under the curve ($AUC_{0-\infty}$) is 55%, 56%, 57%, 58%, 59%, 60%, 65%, 70%, 75%, 80%, 85%, 90%, 95%, 100%, 105%, 110%, 115%, 120% or 125% of an immediate release formulation.

Also provided are controlled release compositions that include an amount of an agent that reduces the number of circulating platelets, such as anagrelide, 3-OH anagrelide or analog or derivative thereof, effective to reduce the number of circulating platelets in a subject in a delivery form formulated for release where the apparent half life of the platelet number reducing agent is increased by at least a factor of two with respect to an immediate release formulation. In some embodiments, the apparent half life of the platelet number reducing agent is increased to at least 4 hours, particularly to at least 6 or 8 or 10 or 12 hours.

Also provided are controlled release compositions that include an amount of an agent that reduces the number of circulating platelets, such as anagrelide, 3-OH anagrelide or analog or derivative thereof, effective to reduce circulating platelet number in a subject in a delivery form that provides an effective duration of activity of the platelet number reducing agent of 5, 6, 7, 8, 9, 10, 11, 12, 13, 14, 15, 16, 17, 18, 19, 20, 21, 22, 23 or 24 hours or more.

Also provided are controlled release compositions that include an amount of an agent that reduces the number of circulating platelets, such as anagrelide, 3-OH anagrelide or analog or derivative thereof, effective to reduce circulating platelet number in a subject in a delivery form formulated to achieve a steady state plasma level of the platelet number reducing agent within 6 doses or fewer.

Exemplary platelet number reducing agents include anagrelide, 3-hydroxy anagrelide, an analog or derivative of anagrelide and pharmaceutically acceptable salts thereof. The platelet number reducing agent can be released in an amount and at a rate that reduces circulating platelet number without meaningfully influencing (e.g., without eliciting adverse reactions associated with) a phosphodiesterase (PDE) system, such as PDE III and PDE V, thereby reducing the adverse event profile of the platelet number reducing agent. The composition can regulate the platelet number reducing agent to a restricted plasma concentration range sufficient to interfere with TPO-induced platelet production without meaningfully inhibiting a PDE system. The composition also can release the platelet number reducing agent at a rate and in an amount to provide a restricted plasma concentration range to reduce circulating platelet number in a subject without meaningfully affecting cellular levels of cAMP and/or cGMP (e.g., without eliciting adverse reactions associated with modulation of cellular levels of cAMP and/or cGMP).

Also provided herein are compositions that include a plurality of solid support cores having an optional preparatory coat; a substrate layer that includes a platelet number reducing coat; an optional seal coat layer that includes a substantially water-soluble polymer on or enveloping the substrate layer; a release control component effective for controlled release of the platelet number reducing agent; an optional finishing coat and/or an optional enteric coating. The solid support cores can be spheroid, particularly spherical. The solid core can be a spheroid granule, pellet or bead that includes a substantially water soluble, swellable or insoluble material or combinations thereof. Exemplary materials of the solid support core include sugar, starch or derivatives thereof, alginate, gellan gum, a polyol or combinations thereof. For example, the solid core can be a non-pareil sugar sphere.

The composition can include a preparatory coat on or enveloping the solid core. The preparatory coat can include a hydrophilic polymer. Exemplary hydrophilic polymers include cellulose derivatives, such as hydroxypropyl methyl cellulose (HPMC), hydroxypropyl cellulose (HPC), carboxymethyl cellulose (CMC), guar gum, xanthan gum, starch, including amylose and amylopectin, modified starch or polyvinylpyrrolidone (PVP).

In the compositions provided herein, the platelet number reducing agent can be in the form of microparticles. The microparticles maintain or increase availability of the agent and can enhance its solubility. The microparticles of the platelet number reducing agent can have a diameter of less than about 25 μm or 25 μm such as ranging from about 0.05 to about 25.0 μm or 0.05 to 25.0 μm, including less than or equal to 12, 11, 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06 or 0.05 microns. The microparticles can be selected to be uniformly of one size, such as 10 microns, or the microparticles can be a distribution of sizes, such as at least 90% less than 25 microns or at least 50% less than or equal to 12 microns. The size of the platelet number reducing agent microparticles can vary within large limits which are set by the desired rates of release of the agent and by physical stability and mechanical properties of the final product.

The compositions provided herein can include an excipient, such as a binder, a surfactant, a filler or combinations thereof. Exemplary binders include water-soluble, hydrophilic polymers, such as polyvinyl pyrrolidone, a cellulosic polymer (such as hydroxypropyl methylcellulose, hydroxypropyl cellulose, carboxy methyl cellulose, hydroxymethyl cellulose, particularly hydroxypropyl methylcellulose, and in particular a low molecular weight hydroxypropyl methylcellulose), gelatin, gum arabic, gellan gum, xanthan gum, carrageenan, polyethylene oxide, dextrin, a starch or starch derivative, povidone and polymethacrylates. Exemplary fillers include lactose, glucose, fructose, sucrose, dicalcium phosphate, a polyol (such as sorbitol, mannitol, lactitol, xylitol, isomalt and erythritol), a hydrogenated starch hydrolysate, corn starch, potato starch, and cellulose acetate, or a mixture thereof. In some embodiments, the composition includes a surfactant.

The compositions provided herein can include a release control component. The release control component can include any polymer that modulates the release characteristics of an active agent, such as a platelet number reducing agent. Exemplary polymers include ethyl cellulose, hydroxypropyl cellulose, hydroxypropyl methyl cellulose or a mixture of two or more of such cellulose derivatives, polyvinyl acetate, povidone, cross-linked starch, cross-linked chitosan, cross-linked gelatin, cross-linked hyaluronic acid, cross-linked polyvinyl alcohol, cross-linked sodium carboxymethyl cellulose, cross-linked polyvinyl pyrrolidone, carboxypolymethylene, zein or combinations thereof, particularly ethyl cellulose or a combination of ethyl cellulose and hydroxypropyl methyl cellulose, or polyvinylacetate, or a combination of polyvinyl acetate and povidone.

The compositions provided herein optionally include a finishing coat on or enveloping the release control component. The finishing coat can include a hydrophilic polymer. Exemplary hydrophilic polymers include hydroxypropyl methyl cellulose (HPMC), hydroxypropyl cellulose (HPC), carboxymethyl cellulose (CMC), other cellulose ethers, polyvinyl alcohol, polyethylene glycol, starch, xanthan gum, gellan gum, modified starch, polyvinylpyrrolidone (PVP) and combinations thereof. The compositions also can include an enteric coating, which includes a selectively soluble polymer. Generally, the polymer of an enteric coating selectively hydrates at a designated pH, usually at a pH more alkaline than the stomach. Exemplary enteric coatings include, but are not limited to, acrylic resins, fats, fatty acids, waxes, wax mixtures, shellac, ammoniated shellac, phenylsalicylate, methacrylic acid copolymers, maleic acid co-polymers, such as styrene maleic acid co-polymers, and the phthalate or succinate salts of the following polymers: cellulose acetate, hydroxyethyl ethyl cellulose, hydroxypropyl methyl cellulose and polyvinyl acetate, or combinations thereof.

The compositions can be provided in a delivery form such as a tablet or a capsule or an edible film or as a free flowing formation such as a sachet or suspension. In some embodiments, the delivery form includes an immediate release form of the platelet number reducing agent in combination with a controlled release composition as described herein.

Also provided are compositions that include a platelet number reducing agent, formulated to release the platelet number reducing agent in an amount effective to reduce an elevated level of circulating platelet count in a subject to near normal or normal levels.

Also provided are compositions that include a platelet number reducing agent, formulated to release the platelet number reducing agent in an amount effective to reduce circulating platelet count in a subject to low normal or below normal levels.

Also provided are compositions that include a platelet number reducing agent and another therapeutic agent. Exemplary of these other therapeutic agents are anti-inflammatory agents, anti-thrombotic agents, ADP receptor antagonists, glycoprotein IIb/IIIa receptor inhibitors, cyclooxygenase-2 inhibitors, fibrinolytic agents, lipid reducing agents, HMG-CoA reductase inhibitors, angiotensin system inhibitors, chemotherapeutic anti-cancer drugs, alkylating agents, thromboxane synthetase inhibitors, cell signaling molecules and JAK-2 inhibitors.

Also provided are unit dosage forms that include a tablet formed from, or a capsule containing, spheroid granules, pellets or beads that include an amount from about 10 ng or 10 ng to about 1000 µg or 1000 µg of microparticles of a platelet number reducing agent, where the spheroid granules, pellets or beads include a solid support core of a substantially water soluble, swellable or insoluble material; an optional preparatory coat; a substrate layer including the microparticles of the platelet number reducing agent; an optional seal coat layer including a substantially water-soluble polymer on or enveloping the substrate layer; a release control component effective for controlled release of the platelet number reducing agent; and an optional finishing coat, where the unit dosage form produces a peak plasma level of platelet number reducing agent at least 50% lower than produced by an immediate release formulation. In some embodiments, such unit dosage forms include an immediate release form of a platelet number reducing agent. In some embodiments, the immediate release form of the platelet number reducing agent includes spheroid granules, pellets or beads that include an amount from about 10 ng or 10 ng to about 1000 µg or 1000 µg of a platelet number reducing agent; and the spheroid granules, pellets or beads include a solid support core of a substantially water soluble, swellable or insoluble material; an optional preparatory coat; and a substrate layer that includes the microparticles of the platelet number reducing agent.

Also provided are methods of reducing circulating platelet number in a subject. The methods include administering to the subject any of the controlled release compositions including a platelet number reducing agent described herein. In some embodiments, the composition delivers an amount of the platelet number reducing agent effective to reduce circulating platelet count in the subject by at least 10% of pre-treatment levels. In some embodiments, an elevated circulating platelet count is reduced to at least a normal level. In some embodiments, the circulating platelet count is reduced to at least a low normal level. In some embodiments, the subject has a normal platelet count prior to treatment. In some embodiments, the subject has an above normal platelet count prior to treatment. In the methods provided herein, the platelet number reducing agent is released in an amount and at a rate that reduces adverse events associated with immediate release formulations of the platelet reducing agent. In the methods provided herein, the platelet number reducing agent is released in an amount and at a rate that reduces circulating platelet number in a subject without overtly causing clinical symptoms that prevent or limit therapeutic use of the platelet number reducing agent. In embodiments where the platelet number reducing agent is anagrelide, 3-OH anagrelide or a metabolite or derivative or analog thereof, the agent is released at a rate and in an amount that reduces circulating platelet number in a subject without inhibiting or minimally inhibiting phosphodiesterase (PDE), such as PDE III and PDE V or combinations thereof, so as to reduce the adverse event profile of the platelet number reducing agent.

Also provided are methods of treating or preventing a thrombotic or thromboembolic event or to inhibit a vasoocclusive event in a subject. The methods include administering to a subject in need of such treatment any of the controlled release compositions of platelet number reducing agent described herein, where the composition delivers an amount of the platelet number reducing agent effective to reduce circulating platelet count in the subject by at least 10% of pre-treatment levels. In some embodiments, an elevated circulating platelet count is reduced to at least a normal level. In some embodiments, the circulating platelet count is reduced to at least a low normal level. In some embodiments, the subject has a normal platelet count prior to treatment. In some embodiments, the subject has an above normal platelet count prior to treatment.

Also provided are methods of treating a subject with a vascular disease. The methods include administering to a subject in need of such treatment a controlled release composition including a platelet number reducing agent as described herein, where the composition delivers an amount of the platelet number reducing agent effective to reduce circulating platelet count in the subject by at least 10% of pre-treatment levels. The vascular disease can be arteriosclerosis, cardiovascular disease, cerebrovascular disease, renovascular disease, mesenteric vascular disease, pulmonary vascular disease, ocular vascular disease or peripheral vascular disease.

Also provided are methods for treating hypercholesterolemia, hypertension and/or atherosclerosis, which include administering to a subject in need of such treatment a controlled release composition including a platelet number reducing agent as described herein.

In some embodiments, a composition provided herein is administered prior to a surgical procedure. The composition including the platelet number reducing agent is administered at a time prior to surgery sufficient for at least one round of platelet turnover to occur. About 10-20% of normal platelets are renewed every day. Thus, for normal platelets, a complete round of platelet turnover generally occurs every 5-10 days. Thus, the composition including the platelet number reducing agent is administered at or about 5 to 10 days prior to surgery. In some embodiments, the platelet number reducing agent is administered at a time prior to surgery sufficient for at least two rounds of platelet turnover to occur. Thus, the composition including the platelet number reducing agent is administered at or about 10 to 20 days prior to surgery. Exemplary surgical procedures include coronary angiography, coronary stent placement, coronary by-pass surgery, carotid artery procedure, peripheral stent placement, vascular grafting, thrombectomy, peripheral vascular surgery, vascular surgery, organ transplant, artificial heart transplant, vascular angioplasty, vascular laser therapy, vascular replacement and vascular stenting.

In some embodiments, a composition provided herein is administered to a subject following a surgical procedure, such as coronary angiography, coronary stent placement, coronary by-pass surgery, carotid artery procedure, peripheral stent placement, vascular grafting, thrombectomy, peripheral vascular surgery, vascular surgery, organ transplant, artificial heart transplant, vascular angioplasty, vascular laser therapy, vascular replacement and vascular stenting.

Also provided are methods of treatment or prevention of a thrombotic, thromboembolic or vaso-occlusive event that includes co-administering a platelet number reducing agent composition described herein with another therapeutic agent. Exemplary other therapeutic agents that can be co-administered include anti-inflammatory agents, anti-thrombotic agents, ADP receptor antagonists, glycoprotein IIb/IIIa receptor inhibitors, cyclooxygenase-2 inhibitors, fibrinolytic agents, lipid reducing agents, HMGCoA reductase inhibitors, angiotensin system inhibitors, chemotherapeutic anti-cancer drugs, alkylating agents, thromboxane synthetase inhibitors, cell signaling molecules and JAK-2 inhibitors.

In some embodiments, the composition includes an anti-inflammatory agent in addition to a platelet number reducing agent. In some embodiments, the methods include co-administration of a platelet number reducing agent composition described herein with an anti-inflammatory agent. Exemplary anti-inflammatory agent s include alclofenac; alclometasone dipropionate; algestone acetonide; alpha amylase; amcinafal; amcinafide; amfenac sodium; amiprilose hydrochloride; anakinra; anirolac; anitrazafen; apazone; aspirin; balsalazide disodium; bendazac; benoxaprofen; benzydamine hydrochloride; bromelains; broperamole; budesonide; carprofen; ciclopofen; cintazone; cliprofen; clobetasol propionate; clobetasone butyrate; clopirac; cloticasone propionate; cormethasone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; flufenamic acid; flumizole; flunisolide acetate; flunixin; flunixin meglumine; fluocortin butyl; fluorometholone acetate; fluquazone; flurbiprofen; fluretofen; fluticasone propionate; furaprofen; furobufen; halcinonide; halobetasol propionate; halopredone acetate; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lornoxicam; loteprednol etabonate; meclofenamate-sodium; meclofenamic acid; meclorisone dibutyrate; mefenamic acid; mesalamine; meseclazone; methylprednisolone suleptanate; morniflumate; nabumetone; naproxen; naproxen sodium; naproxol; nimazone; olsalazine sodium; orgotein; orpanoxin; oxaprozin; oxyphenbutazone; paranyline hydrochloride; pentosan polysulfate sodium; phenbutazone sodium glycerate; pirfenidone; piroxicam; piroxicam cinnamate; piroxicam olamine; pirprofen; prednazate; prifelone; prodolic acid; proquazone; proxazole; proxazole citrate; rimexolone; romazarit; salcolex; salnacedin; salsalate; salicylates; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triclonide; triflumidate; zidometacin; glucocorticoids; and zomepirac sodium. In particular, the anti-inflammatory agent is aspirin.

In some embodiments, the composition includes an ADP receptor antagonist in addition to a platelet number reducing agent. In some embodiments, the methods include co-administration of a platelet number reducing agent composition described herein with an ADP receptor antagonist. Exemplary ADP receptor antagonists include clopidogrel, ticlopidine, prasugrel, sulfinpyrazone, AZD6140, AZD6933 and AR-C69931. In some embodiments, the ADP receptor antagonist is clopidogrel. In some embodiments, the ADP receptor antagonist is prasugrel.

In some embodiments, the composition includes a glycoprotein IIb/IIIa receptor inhibitor in addition to a platelet number reducing agent. In some embodiments, the methods include co-administration of a platelet number reducing agent composition described herein with a glycoprotein IIb/IIIa receptor inhibitor. Exemplary glycoprotein IIb/IIIa receptor inhibitors include abciximab, fradafiban, lamifiban, lotrafiban, orbofiban, roxifiban, sibrafiban, tirofiban and xemilofiban.

In some embodiments, the composition includes an anti-coagulant agent in addition to a platelet number reducing agent. In some embodiments, the methods include co-administration of a platelet number reducing agent composition described herein with an anti-coagulant agent. Exemplary an anti-coagulant agents include a vitamin K antagonist, coumarin and coumarin derivatives, warfarin sodium; a heparin; ardeparin sodium; bivalirudin; bromindione; coumarin dalteparin sodium; desirudin; dicumarol; lyapolate sodium; nafamostat mesylate; phenprocoumon sulfatide; and tinzaparin sodium.

In some embodiments, the composition includes a thrombolytic agent in addition to a platelet number reducing agent. In some embodiments, the methods include co-administration of a platelet number reducing agent composition described herein with a thrombolytic agent. Exemplary thrombolytic agents include ancrod, anistreplase, bisobrin lactate, brinolase, Hageman factor (i.e., factor XII) fragments, tissue factor pathway inhibitor (TFPI), molsidomine, plasminogen activators such as streptokinase, tissue plasminogen activators (TPA) and urokinase, plasmin and plasminogen, and inhibitors of factor Xa, factor VIIa, factor IXa, factor Va, factor VIIIa, factor XIa, factor XIIa and factor XIIIa.

In some embodiments, the composition includes a lipid reducing agent in addition to a platelet number reducing agent. In some embodiments, the methods include co-administration of a platelet number reducing agent composition described herein with a lipid reducing agent. Exemplary lipid reducing agents include bezafibrate, ciprofibrate, clofibrate, etofibrate, fenofibrate, gemfibrozil, ronifibrate and simfibrate; a statin, such as atorvastatin, cerivastatin, fluvastatin, lovastatin, mevastatin, pitavastatin, pravastatin, rosuvastatin and simvastatin, niacin or a niacin derivative, including acipimox, aluminium nicotinate, niceritrol (pentaerythritol tetranicotinate), nicofuranose and nicotinyl alcohol, a bile acid sequestrant, including colesevelam, colestyramine, colestipol and colextran, a CETP inhibitor, such as anacetrapib, benfluorex, cholestyramine, dextrothyroxine, ezetimibe, laropiprant, meglutol, omega-3-triglycerides, policosanol, probucol and tiadenol.

In some embodiments, the composition includes a cyclooxygenase-2 (COX-2) inhibitor in addition to a platelet number reducing agent. In some embodiments, the methods include co-administration of a platelet number reducing agent composition described herein with a COX-2 inhibitor. Exemplary COX-2 inhibitors include aspirin, celecoxib (e.g., as marketed under the trademark Celebrex®), lumiracoxib (e.g., as marketed under the trademark Prexige®) and etoricoxib (e.g., as marketed under the trademark Arcoxia®).

In some embodiments, the composition includes an angiotensin system inhibitor in addition to a platelet number reducing agent. In some embodiments, the methods include co-administration of a platelet number reducing agent composition described herein with an angiotensin system inhibitor. Exemplary angiotensin system inhibitors include angiotensin-converting enzyme (ACE) inhibitors, such as benazepril, captopril, cilazapril, delapril, enalapril, fosinopril, imidapril, lisinopril, moexipril, perindopril, quinapril, ramipril, spirapril, temocapril, trandolapril and zofenopril, angiotensin II receptor antagonists, such as azilsartan, candesartan, eprosartan, irbesartan, losartan, olmesartan, tasosartan, telmisartan and valsartan, agents that activate the catabolism of angiotensin II, and agents that prevent the synthesis of angiotensin I from which angiotensin II is ultimately derived.

In some embodiments, the composition includes a chemotherapeutic cancer drug in addition to a platelet number reducing agent. In some embodiments, the methods include co-administration of a platelet number reducing agent composition described herein with a chemotherapeutic cancer drug. Exemplary chemotherapeutic cancer drugs include busulfan, carmustine, chlorambucil, cyclophosphamide, doxorubicin, estramustine, hepsulfan, hydroxycarbamide (hydroxyurea), ifosfamide, lomustine, melphalan, methotrexate, pipobroman and thioTEPA. In some embodiments, a chemotherapeutic cancer drug is hydroxycarbamide.

In some embodiments, the composition includes a thromboxane synthetase inhibitor in addition to a platelet number reducing agent. In some embodiments, the methods include co-administration of a platelet number reducing agent composition described herein with a thromboxane synthetase inhibitor. Exemplary thromboxane synthetase inhibitors and 1-carboxyhexyl-, 1-carboxyheptyl, and 1-carboxyoctyl-imidazoles, 4(Z)-6-[(4RS,5SR)-4-(2-hydroxyphenyl)-1,3-dioxan-5-yl]hex-4-enoic acid, BM-573, camonagrel, CGS-12970, daltroban, dazmegrel, DTTX30, E-6700, FCE-27262, imitrodast (CS-518), isbogrel (CV-4151), ketoconazole, KK-505, KY-063, nafagrel (DP-1904), ozagrel (OKY-046), picotamide, pirmagrel (CGS-13080), ridogrel, SQ29548, rolafagrel (FCE-22178), satigrel (E-5510), sulotroban, terbogrel and UK 38485.

In some embodiments, the composition includes a cell signaling molecule in addition to a platelet number reducing agent. In some embodiments, the methods include co-administration of a platelet number reducing agent composition described herein with a cell signaling molecule. Exemplary cell signaling molecules include a cytokine, a neutrophil activating peptide-2 and its analogs, macrophage inflammatory protein and its analogs, and platelet-factor 4.

In some embodiments, the composition includes a JAK-2 inhibitor in addition to a platelet number reducing agent. In some embodiments, the methods include co-administration of a platelet number reducing agent composition described herein with a JAK-2 inhibitor. Exemplary JAK-2 inhibitors include AT9283, VX-680, MK0457, TG101209, INCB018424, LS104, XLO19, TG101348, vorinostat, 4-aryl-2-amino-pyridines and 4-aryl-2-aminoalkyl-pyridines as described in WO/2007/089768 and the inhibitors described in U.S. Pat. No. 7,070,972.

The methods can include administration of an amount of a platelet number reducing agent whereby platelet count is reduced by at least 20%, and in some embodiments platelet count is reduced by at least 50%. The methods can include administration of an amount of a platelet number reducing agent whereby platelet count is reduced to below $200 \times 10^3$ platelets per such as to a level of at or about $150 \times 10^3$ platelets per µl. The methods can include administration of an amount of a platelet number reducing agent whereby platelet count is reduced by at least 10% and to an amount above $200 \times 10^3$ platelets per µl. In some embodiments, the methods include administration of an amount of a platelet number reducing agent whereby platelet count is reduced by at least 10% and to an amount below $200 \times 10^3$ Also provided are methods for treating a myeloproliferative disease or disorder in a subject. The methods include administering a composition including a platelet number reducing agent as described herein that releases the agent in an amount and at a rate effective to reduce circulating platelet count by at least 10%, targeting a platelet count of less than $600 \times 10^3$ platelets per µl, in a subject with a myeloproliferative disease or disorder, such as idiopathic myelofibrosis, essential thrombocythemia and polycythemia vera. In some embodiments, the circulating platelet count is reduced to less than or equal to $450 \times 10^3$ platelets per µl or to the normal range.

DETAILED DESCRIPTION

Figure 1:
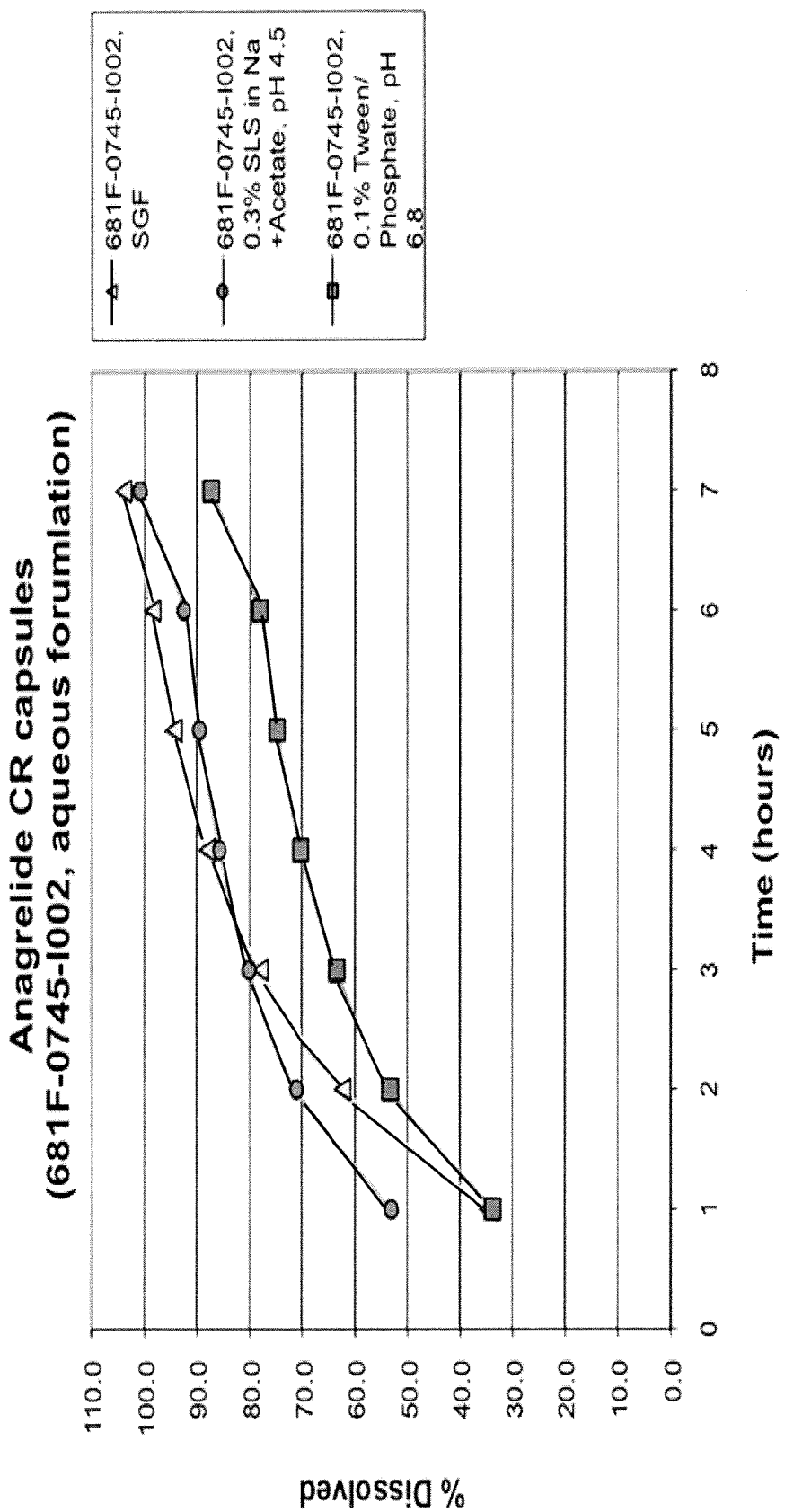
FIG. 1 is a graph showing the dissolution profiles of different anagrelide CR capsules (681F-0745-1002, aqueous formulation) at three pH conditions. The 7 hour time is considered infinity (paddles at 250 rpm for 1 hour).

A. Definitions
B. The Role of Platelets and Health
C. Platelet-related conditions and diseases
  1. Thrombotic events
  2. Vaso-occlusive events
  3. Vascular disease
  4. Myeloproliferative disorders
    a. Essential thrombocythemia (ET)
    b. Polycythemia vera (PV)
    c. Idiopathic myelofibrosis (IM)
  5. Other conditions
D. Anagrelide
  1. Chemistry
  2. Metabolites
  3. Derivatives and Analogs of Anagrelide
  4. Pharmacokinetic properties
  5. Mechanism of action
E. Compositions
  1. Form
    a. Cores
    b. Platelet number reducing agent
    c. Microparticles
    d. Coatings
      i. Optional preparatory coat
      ii. Substrate layer
      iii. Optional seal coat layer
      iv. Controlled release component
      v. Optional Finishing coat
  2. Pharmaceutical delivery forms
    a. Compositions for oral administration
    b. Compositions for other routes of administration
F. Methods of making coated particles for use in the compositions
G. Articles of Manufacture
H. Assays for determining activity of a platelet number reducing agent
I. Methods of treatment using the compositions
J. Combination Therapies
  1. Platelet adhesion inhibitors
  2. Platelet aggregation inhibitors
  3. Anti-inflammatory agents
  4. Plasminogen activator receptor antagonists
  5. Anti-thrombotic agents
  6. ADP receptor antagonists
  7. Glycoprotein IIb/IIIa receptor inhibitors
  8. Anti-coagulant and/or fibrinolytic agents
  9. Lipid reducing agents
  10. Cyclooxygenase-2 (COX-2) inhibitors
  11. Angiotensin system inhibitors
  12. Antihypertensive agents
  13. Chemotherapeutic anti-cancer drugs and alkylating agents
  14. Thromboxane synthesis inhibitors
  15. Cell signaling molecules
  16. JAK-2 inhibitors
K. Administration
L. Examples

A. Definitions

Unless specific definitions are provided, the nomenclature used in connection with, and the laboratory procedures and techniques of, analytical chemistry, biochemistry, synthetic organic chemistry, and medicinal and pharmaceutical chemistry described herein are those known in the art. All patents, patent applications and published materials referred to throughout the entire disclosure herein, unless noted otherwise, are incorporated by reference in their entirety for any purpose. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of the subject matter claimed.

Standard techniques can be used for chemical syntheses, chemical analyses, pharmaceutical preparation, formulation and delivery, and treatment of subjects. Standard techniques can be used for recombinant DNA, oligonucleotide synthesis, and tissue culture and transformation (e.g., electroporation, lipofection). Reactions and purification techniques can be performed e.g., using kits according to manufacturer's specifications or as commonly accomplished in the art or as described herein. The foregoing techniques and procedures generally are performed according to conventional methods well known in the art and as described in various general and more specific references that are cited and discussed herein. See e.g., Sambrook et al., Molecular Cloning: A Laboratory Manual (2d ed., Cold Spring Harbor Laboratory Press, Cold Spring Harbor, N.Y. (1989).

As used herein, the abbreviations for any protective groups, amino acids and other compounds are, unless indicated otherwise, in accord with their common usage, recognized abbreviations, or the IUPAC-IUB Commission on Biochemical Nomenclature (1972) *Biochem.*, 11: 942-944.

As used herein, use of the singular includes the plural unless specifically stated otherwise.

As used herein, "or" means "and/or" unless stated otherwise. Furthermore, use of the term "including" as well as other forms, such as "includes," and "included," is not limiting.

As used herein, the terms "treating" or "treatment" encompass responsive and/or prophylaxis measures, e.g., designed to inhibit, slow or delay the onset of a symptom of a disease or disorder, achieve a full or partial reduction of a symptom or disease state, and/or to alleviate, ameliorate, lessen, or cure a disease or disorder and/or its symptoms.

As used herein, "treating a subject with a disease or condition" means that the subject's symptoms are partially or totally alleviated, or remain static following treatment.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

As used herein, "prophylaxis" refers to prevention of a potential disease and/or a prevention of worsening of symptoms or progression of a disease.

As used herein, "prevention" refers to absolute prevention of a particular disease or disorder or reducing the risk of developing a disease or disorder. Since it generally is not possible to ascertain whether a disease or disorder never develops, prevention includes reduction in the risk of developing or having a disease or disorder.

As used herein, a "derivative" is a compound obtained or produced by modification of another compound of similar structure. Derivatives can be produced by one or more modification steps known in the art.

As used herein, "area under the curve or AUC" refers to the area between the peak and the baseline in peak-type signals. Area under the curve can be calculated using a summation method or by use of a mathematical function, such as a "best fit" function that approximates the peak shape of the observed data and reporting the area under the "best fit" peak function as the net area.

As used herein, the term "combination" refers to any association between two or more items or elements.

As used herein, the term "monitoring" refers to observing an effect or absence of any effect, and includes observation of a clinical subject. For example, one can monitor an effect of an agent, e.g., a platelet number reducing agent, on a parameter, e.g., platelet count, by counting the number of platelets in a given volume of blood. One also can observe a subject to determine whether any adverse events occur after administration of a therapeutic agent. As comparisons, placebo treated subjects can be used as controls. Subjects can be monitored regularly over a period of time for repeated administrations.

As used herein, the term "contacting" refers to bringing two or more materials into close enough proximity that they can interact. In certain embodiments, contacting can be accomplished in a vessel such as, e.g., a test tube, flask, petri dish or mixing tank. In certain embodiments, contacting can be performed in the presence of additional materials.

As used herein, the term "subject" is an animal, typically a mammal, including humans, nonhuman primates, dogs, cats, sheep, goats, horses, cows, pigs or rodents.

As used herein, the term "apparently healthy subject" is one who, at the time of treatment, does not exhibit disease signs or symptoms. In other words, such individuals, if examined by a medical professional, would be characterized as healthy and free of symptoms of disease. The apparently healthy subjects however can still demonstrate particular risk factors which can place them at an elevated risk of a thrombotic event. For example, such subjects can be apparently healthy and still have a family history of thrombosis-related disorders. Alternatively, the subject can have symptoms of vaso-occlusive disease (such as chest pain, heart palpitations, shortness or breath, as well as a wide range of other symptoms well known to a medical practitioner of ordinary skill) or can have been diagnosed with such disease.

As used herein, the term "patient" includes human and animal subjects.

As used herein, the term "carrier" refers to a compound that facilitates the incorporation of another compound into cells or tissues. For example, dimethyl sulfoxide (DMSO) is a commonly used carrier for improving incorporation of certain organic compounds into cells or tissues.

As used herein, the term "platelet number reducing agent" refers to any agent, chemical or compound that reduces circulating platelet number in a subject.

As used herein, the term "pharmaceutical composition" refers to a chemical compound or composition capable of inducing a desired therapeutic effect in a subject. In certain embodiments, a pharmaceutical composition contains an active agent, which is the agent that induces the desired therapeutic effect. In certain embodiments, a pharmaceutical composition contains inactive ingredients, such as, for example, carriers and excipients.

As used herein, the term "therapeutically effective amount" refers to an amount of a pharmaceutical composition sufficient to achieve a desired therapeutic effect. The effective amount will depend upon the mode of administration, the particular condition being treated and the desired outcome. It also will depend upon the stage of the disease or condition (if any), the age and physical condition of the subject, the nature of any concurrent therapy, and similar factors well known to the medical practitioner. For prophylactic applications, it is that amount sufficient to delay the onset of, inhibit the progression of, or halt altogether the particular condition being treated, thereby producing patient benefit. For therapeutic applications, it is that amount sufficient to achieve a medically desirable result, thereby producing patient benefit. In some instances, patient benefit can be measured by a reduction in morbidity and/or mortality. In some cases this is a decrease in cell maturation and/or proliferation. In the case of megakaryocytes, the medically desirable result can be to inhibit thrombosis via blocking of megakaryocyte maturation, endoreduplication and/or proliferation. In other cases, it is an increase in platelet consumption, elimination or death. Ultimately, the amount that is administered is one effective for reducing an elevated platelet count, such as in subjects with a myeloproliferative disorder, to less than $600\times10^3$ platelets per particularly to $450\times10^3$ platelets per µl or less, targeting a normal platelet count. In subjects that do not have a myeloproliferative disorder, the amount that is administered is one effective for reducing to a low normal and in some embodiments below normal levels in a subject.

As used herein, the term "pharmaceutically acceptable" refers to a formulation of a compound that does not significantly abrogate the biological activity, a pharmacological activity and/or other properties of the compound when the formulated compound is administered to a subject. In certain embodiments, a pharmaceutically acceptable formulation does not cause significant irritation to a subject.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to chloroprocaine, choline, N,N'-dibenzyl-ethylenediamine, ammonia, diethanolamine and other hydroxy alkylamines, ethylenediamine, N-methylglucamine, procaine, N-benzyl-phenethylamine, 1-para-chlorobenzyl-2-pyrrolidin-1'-ylmethyl-benzimidazole, diethylamine and other alkylamines, piperazine and tris (hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, a "vaso-occlusive event" refers to an event that is characterized by or results in a decrease in the internal diameter of blood vessels either locally or systemically to an extent that impedes blood flow in a subject. A vaso-occlusive event can be of a pathological nature. Thus, a vaso-occlusive event embraces pathological narrowing or complete occlusion of a stent, a vascular graft or a blood vessel. A vaso-occlusive event includes events that cause blood vessel narrowing or occlusion (such as thrombotic events, thromboembolic events and intimal hyperplasia) as well as conditions resulting from such blood vessel narrowing (such as myocardial infarction and ischemic stroke). A vaso-occlusive event also includes abnormal blood vessel growth induced by the presence of platelets and the factors they secrete. An example of this latter form of vaso-occlusive event is intimal hyperplasia which results in a narrowing of the blood vessels (i.e., reduction in the diameter of blood vessels either locally or throughout an extended segment of the vessel) due to a hyperproliferation of cells of the intimal layer of the blood vessel wall.

As used herein, "pathological narrowing or occlusion" refers to narrowing or occlusion that is abnormal and/or disease-related.

As used herein, a "thrombus" refers to an aggregation of blood factors, primarily platelets and fibrin with entrapment of cellular elements, frequently causing vascular obstruction at the point of its formation.

As used herein, a "thrombotic event" refers to an event associated with the formation or presence of a thrombus in a subject, particularly when present in the vasculature. Thrombotic events embrace thrombosis at a local primary site as well as at a distal site (i.e., thromboembolism) and a distal thrombotic event (e.g., a thromboembolic event such as for example an embolic stroke).

As used herein, "thrombosis" collectively refers to conditions caused by the formation, development, or presence of a thrombus. As used herein, the term thrombosis is intended to embrace thromboembolism.

As used herein, "thromboembolism" refers to conditions characterized by the blocking of a vessel, other than at the initial site of thrombus formation, by a thrombus that has been carried to the distal site by the blood current.

As used herein, "inhibiting a vaso-occlusive event" refers to the prevention of the formation of a vaso-occlusive event, or to the reduction of the progression and/or consequences of an already established vaso-occlusive event or to induction of regression of a vaso-occlusive event.

As used herein, "peripheral vascular disease" refers to diseases of blood vessels outside the heart and brain. The term peripheral vascular disease includes any disorder that affects any of the blood vessels. The term often is used as a synonym for peripheral artery disease. Peripheral vascular diseases often are caused by structural modifications in the blood vessels, including narrowing and inflammation. The structural modification can include deposition of materials on the walls of the blood vessels, such as the build up of fat or plaque that inhibits or blocks normal blood flow.

As used herein, "intermittent claudication" refers to a narrowing of the arteries that supply blood to the legs, resulting in a limited supply of oxygen to the leg muscles. Intermittent claudication often manifests as cramps, aches and occasionally a burning pain in the legs that is intermittent in nature. The narrowing of the artery can be transient, such as due to a vasospasm, or can be permanent, such as due to atherosclerosis.

As used herein, "myocardial infarction" refers to an irreversible injury to the heart muscle. Myocardial infarction generally results from an abrupt decrease in coronary blood flow following a thrombotic occlusion (e.g., a thromboembolism) of a coronary artery. The thrombus, in many instances, forms after the rupture of atherosclerotic plaques in diseased coronary arteries. Such injury is highly correlated with factors such as cigarette smoking, hypertension and lipid accumulation.

As used herein, "stroke" refers to sudden death of brain cells caused by reduced blood flow to the brain, often caused by a cerebrovascular accident, including a thrombus or embolus that occludes an artery (an ischemic stroke), or due to rupture of an artery or hemorrhage into the brain (hemorrhagic stroke).

As used herein, "transient ischemic attack" or "TIA" refers to a transient acute neurological dysfunction resulting from a thromboembolism in the cerebral circulation.

TIAs are also referred to as a "warning stroke" or "mini-stroke" because they produce stroke-like symptoms but generally no permanent damage. The symptoms that often accompany a TIA are similar to those associated with a stroke, and include sudden dizziness, loss of balance or coordination, sudden visual disturbance, such as loss of acuity in one or both eyes, confusion, trouble speaking or sudden loss of comprehension, and sudden weakness or numbness in the face or extremities such as an arm or leg or both, often effecting only one side of the body.

As used herein, "amaurosis fugax" refers to temporary monocular blindness resulting from a thromboembolism in the retinal vasculature.

As used herein, a "primary vaso-occlusive event" refers to the first known vaso-occlusive event experienced by the subject.

As used herein, a "secondary vaso-occlusive event" refers to a vaso-occlusive event that occurs in a subject known or diagnosed as having previously experienced a vaso-occlusive event (i.e., a primary vaso-occlusive event).

As used herein, a "normal platelet count" refers to a number of platelets in an average subject in a control population, which includes subjects having similar characteristics as the treated individual, such as age and sex. The "normal" level also can be a range, for example, where a population is used to obtain a baseline range for a particular group into which the subject falls. Thus, the "normal" value can depend upon a particular population selected. The "normal" levels are those of apparently healthy subjects who have no prior history of platelet-mediated disorders. Such "normal" levels then can be established as preselected values, taking into account the category in which an individual falls. Appropriate ranges and categories can be selected with no more than routine experimentation by those of ordinary skill in the art. Either the mean or another preselected number within the range can be established as the normal preselected value. As is known in the art, the typical range for platelets in a "healthy" human subject is at or about $150\times10^3$ to $450\times10^3\times10^3$ platelets per μl). For an average healthy population, a normal platelet count is at or about $250\pm50\times10^3$ As used herein, "below normal levels" of platelets refers in an average healthy population refers to a platelet count that is typically at or about $150\times10^3$ less, but greater than about $100\times10^3$ platelets/μl. Human subjects who have a platelet count of less than $100\times10^3$
of less than $25\times10^3$ As used herein, "low normal levels" refers to a platelet count in subjects that is between the median platelet count for the population and $150\times10^3$ As used herein, "near normal levels" refers to a platelet count that is at or about 10% above the range of the normal platelet count of a population. Thus, for an average healthy population as mentioned above, near normal levels would be about $500\times10^3$ As used herein, "high normal levels" refers to a platelet count that is within 10% of the top range of the normal platelet count of a population. Thus, for an average healthy population as mentioned above, high normal levels would be at or about $450\times10^3\times$
$10^3$ As used herein, the terms "platelet level," "platelet number" and "platelet count" are used interchangeably to refer to the number of platelets per a given volume of blood in a subject. The platelet count can be referred to in a number of ways (e.g., per μl of blood, per ml of blood, etc.). Generally, platelet counts are referred to herein as the
  i.e.
used.

As used herein, "treatment of a subject" refers to prophylactic and therapeutic treatment, and refers to the limiting or eliminating altogether the symptoms or the occurrence of a vaso-occlusive event.

As used herein, "co-administering" refers to administering simultaneously two or more compounds as an admixture in a single composition, or sequentially, close enough in time so that the compounds can exert an additive or even synergistic effect, i.e., on reducing cardiomyocyte death in a cardiovascular condition. An exemplary combination is anagrelide and an agent known to be beneficial in the treatment of, for example, a cardiovascular condition, e.g., aspirin.

As used herein, "atherothrombosis" refers to the interaction of blood components such as platelets and clotting factors with areas of vessel wall affected by atheroma leading to acute thrombosis and occlusion of the vessel.

As used herein, the term "pore former" refers to any material that can be dissolved, extracted or leached from the coating in the environment of use. Upon exposure to fluids in the environment of use, for example, a biological fluid, the pore formers are, e.g., dissolved, and channels and pores are formed that fill with the environmental fluid.

As used herein, the term "article of manufacture" is a product that is made and sold and that includes a container and packaging, and optionally instructions for use of the product. For purposes herein, articles of manufacture encompass packaged controlled release compositions as disclosed herein.

As used herein, the "elimination rate constant," abbreviated as IQ, refers to the first order rate constant describing drug elimination from the body. This is an overall elimination rate constant describing removal of the drug by all elimination processes including metabolism and excretion. To calculate the elimination rate constant ($K_{el}$, concentration values (y) versus time (x). Calculations can be made between a time point where log-linear elimination phase begins (TLIN) and the time at which the last concentration above the limit of quantitation (LQCT) occurred. The IQ can be taken as the slope multiplied by (−1).

As used herein, the term "$C_t$" refers to the last observed non-zero concentration.

As used herein, the term "AUC" refers to the area under the concentration-time curve and can be used as a metric for extent of exposure of a pharmaceutical.

As used herein, the term "exposure" refers to AUC.

As used herein, the term "$AUC_{0-\infty} \ldots$" or "$AUC_{0-inf}$" refers to the area under the concentration-time curve from time zero to infinity (extrapolated). $AUC_{0-\infty}$ can be calculated as $AUC_{0-t}+(C_t/K_{el})$ where $C_t$ is the calculation at time t.

As used herein, the term "total exposure" refers to $AUC_{0-\infty}$.

As used herein, the term "$AUC_{0-t}$" refers to the area under the concentration-time curve from time zero to time of last non-zero (last measurable) concentration. The linear trapezoidal rule was used to calculate $AUC_{0-t}$.

As used herein, the term "$AUC_{t/\infty}$" refers to the ratio of $AUC_{0-t}$ to $AUC_{0-\infty}$.

As used herein, the term "$C_{max}$" refers to the maximum (peak) observed plasma concentration.

As used herein, the term "$C_{min}$" refers to the minimum observed plasma concentration, which also can be referred to as the trough concentration.

As used herein, the term "$T_{max}$" refers to the time to reach the maximum (peak) observed plasma concentration $C_{max}$.

As used herein, the term "apparent half-life" or "$t_{1/2}$" "terminal half life" or "$t_{1/2\ el}$" refers to the apparent time required for half the quantity of a drug or other substance administered to an organism to be metabolized or eliminated. The apparent terminal half-life ($T_{1/2\ el}$) is $(\ln 2)/K_{el}$.

As used herein, the term "$W_{50}$" refers to the width of the plasma concentration versus time curve at 50% of the $C_{max}$.

As used herein, the term "angiotensin system inhibitor" refers to an agent that interferes with the function, synthesis or catabolism of angiotensin II.

As used herein, the term "microparticle" refers to a small particle having a diameter of from nanometers to micrometers and refers to solid particles of irregular, non-spherical or spherical shapes, including crystalline particles of micron or sub-micron dimensions.

As used herein, the term "total exposure essentially equivalent to or greater than an immediate release formulation" refers to an exposure that is from at or about 50% to at or about 250% of the total exposure provided by an immediate release formulation.

As used herein, the term "phosphodiesterase" or "PDE" refers to a cyclic nucleotide phosphodiesterase that shows specificity for purine cyclic nucleotide substrates and catalyze cyclic AMP (cAMP) and/or cyclic GMP (cGMP) hydrolysis (e.g., see Thompson, Pharma. Ther. 51: 13-33 (1991)). Cyclic nucleotide phosphodiesterases regulate the steady-state levels of cAMP and cGMP and modulate the amplitude and duration of cyclic nucleotide signal. At least eight different but homologous gene families exist in mammalian tissues. Most families contain distinct genes, many of which are expressed in different tissues as functionally unique alternative splice variants. (e.g., see Beavo, Physiological Reviews 75: 725-748 (1995) and U.S. Pat. No. 5,798, 246). Phosphodiesterase type 3 (PDE III) is an important regulator of responses mediated by cAMP in the cardiovascular system and plays a crucial role in thrombus formation. PDE III is expressed on megakaryocytes. Phosphodiesterase type 5 (PDE V) is an important regulator of responses mediated by cGMP.

As used herein, the term "adverse event profile" refers to drug-related adverse events or side effects commonly associated with a drug. For example, the adverse event profile of inhibitors of phosphodiesterases (PDEs), such as PDE III and PDE V, includes headache, palpitations, tachycardia, cardiac arrhythmia, asthenia, fluid retention, vasodilation, nausea and diarrhea. These effects are primarily mediated through the increase in cAMP and/or cGMP. Adverse events specifically related to inhibition of phosphodiesterase III include headache, diarrhea and abnormal stools, ecchymosis, edema, dizziness, palpitation, tachycardia, angina pectoris, arrhythmia, ventricular extrasystoles, rhinitis, nausea and vomiting, dyspepsia, flatulence, rash, pruritus, chest pain, abdominal pain, asthenia, increased cardiac contractility, accelerated AV nodal conduction, increased ventricular automaticity, heart rate, and coronary blood flow (e.g., see Nolan et al., Int J Cardiol. 35: 343-349 (1992); Product Monograph—Pletal (cilostazol), 2003; and Kumar et al., J Anaesth Clin Pharmacol 20(3): 227-237 (2004)). Adverse events specifically related to inhibition of phosphodiesterase V include headache, transient decreased blood flow to the optic nerve of the eye, causing sudden vision loss, transient hypotension, flushing, dyspepsia, rhinitis, and nasal obstruction (see, e.g., Kiroglu et al., Tohoku Journal of Experimental Medicine 208 (3): 251-254 (2006); Vitezic, Drug Saf. 24(4): 255-65 (2001); Golan et al., *Principles of Pharmacology: The Pathophysiologic Basis of Drug Therapy*, ($2^{nd}$ ed. (paperback, 2008), p. 377) and Lincoln, Molecular Pharmacology 66(1): 11-13 (2004). These side effects reflect the pharmacology of PDE-V inhibition, which elevates cyclic guanosine monophosphate (cGMP) levels, known to cause vasodilation. A decrease in the adverse event profile means that the occurrence, severity or reoccurrence of any of the adverse events or side effects, including those listed above, is reduced or eliminated.

As used herein, the phrase "inhibiting to a clinically significant extent" means inhibiting a system or enzyme, such as phosphodiesterase, to a degree whereby adverse events are manifest. For example, the phrase "inhibiting a phosphodiesterase to a clinically significant extent" means that the inhibition of the phosphodiesterase is to an extent that adverse events, such as headache, palpitations, tachycardia, cardiac arrhythmia, fluid retention, vasodilation, nausea or diarrhea, are manifest in a subject. The phrase "without inhibiting a phosphodiesterase to a clinically significant extent" means that the inhibition of the phosphodiesterase is to an extent that adverse events are not manifest in a subject.

As used herein, the phrase "inhibits megakaryocyte production of platelets" includes inhibition of stimulated megakaryocyte production of platelets, such as by platelet-derived growth factors and other growth factors, as well as the basal production of platelets in a subject having a normal, basal state of platelet production. Individual subjects can have their own level of basal platelet production depending on individual platelet demands. The Mpl ligand, thrombopoietin, provides a negative feedback regulation of platelet production, as circulating levels of unbound Mpl ligand are believed to induce concentration-dependent receptor-mediated proliferative and anti-proliferative maturation of megakaryocytes into platelets. As the number of circulating platelets increases, circulating Mpl ligand is bound to the platelets, and less ligand is available for binding to megakaryocytes. As circulating number of platelets decreases, more Mpl ligand is soluble and unbound, and available for binding to megakaryocytes, ultimately increasing the number of platelets. Megakaryocytes also can be stimulated to produce platelets by other factors, including platelet-derived growth factors. For example, elevated plasma levels of basic fibroblast growth factor has been observed in patients with essential thrombocythaemia and polycythemia vera. Thus, the inhibition of megakaryocyte production of platelets as used herein includes inhibition and/or reduction of basal production of platelets and the inhibition of stimulated production of platelets, such as in myeloproliferative diseases or disorders.

As used herein, the term "anagrelide" refers to 6,7-dichloro-1,5-dihydroimidazo-[2,1-b]quinazolin-2(3H)-one, including its free base form [CAS No. 68475-42-3] and its salt forms, such as the hydrochloride monohydrate [CAS No. 58579-51-4] (see *The Merck Index* ($13^{th}$ ed., 2001), entry 629, page 105). It is the hydrochloride monohydrate, such as that marketed under the trademark Agrylin® in the United States and Canada and that marketed under the trademark Xagrid® in Europe, which is marketed for the reduction of elevated platelet counts and the amelioration of thrombohemorrhagic events in patients with myeloproliferative disorders.

As used herein, the phrase "shelf stability" refers to the ability of the finished product or composition to resist degradation or significant loss in the activity of the pharmaceutical ingredient contained therein during storage. A compound, finished product or composition demonstrates shelf stability if the activity of the pharmaceutical ingredient is at least 95% of the activity of the agent at the beginning of the storage period or at least 95% of the activity of the original dosage formulation.

As used herein, the term "normal storage conditions" refers to ambient temperature or about 20° to 25° C.

As used herein, the term "accelerated testing" refers to storage conditions that include elevated temperature, such as a temperature of about 25° C., and a relative humidity of about 75%.

As used herein, the term "moisture content" or "moisture level" refers to the amount of water in a compound or composition.

As used herein, the term "effective moisture" is the moisture provided to the platelet reducing agent in a finished dosage form. The effective moisture level is sufficient to maintain the crystal water molecules (water of crystallization) in place so that the platelet reducing agent has a hydration level sufficient to maintain crystallinity of the platelet reducing agent particles.

As used herein, the term "immediate-release form" of an active agent refers to the release of the active agent substantially immediately upon contact with gastric juices or other biological fluids, such that the active agent is made bioavailable without substantial delay. An immediate release form of an active agent releases the majority of the active agent within a relatively short time, for example, within about 30 to 60 minutes after oral ingestion.

As used herein, the term "biological fluid" refers to any one or more fluids produced by a biological organism. Exemplary biological fluids include stomach or gastric fluid, intestinal fluid, saliva or other oral fluid, mucus, tears, urine, blood or blood fractions, serum and plasma.

As used herein, the term "deleterious interactions" refers to any chemical or physical interaction between an active agent and another compound or composition that negatively impacts the bioavailability or stability of the active agent. For example, a deleterious interaction can include loss of water of crystallization from a hydrated crystalline form of the active agent to an adjacent molecule or component of the composition. A deleterious interaction also can include degradation of active agent due to or accelerated by interaction with another compound or composition, such as a degradation of active agent during accelerated stability testing catalyzed by or accelerated by interaction with a component of the formulation, such as a plasticizer.

As used herein, the phrase "substantially maintains the hydrated crystal form" refers to minimizing the loss of the water of crystallization. The hydrated crystal form is maintained by keeping most or all of crystal water molecules of a hydrated crystal form of an active agent in place or in proximity to the crystal so that the active agent has a hydration level sufficient to maintain a hydrated crystal form. The loss of the water of crystallization can result in the formation of a hemihydrate crystal form. In some instances, the hemihydrate is not as stable as a hydrated crystalline form. For example, it is known in the art that the hemihydrate of anagrelide is not as stable as the hydrochloride monohydrate crystal form.

As used herein, the term "unit dose" or "unit dosage" refers to physically discrete units, receptacles or containers, such as tablets or capsule, that contain a predetermined quantity of active ingredient, such as a composition provided herein that includes an active ingredient, calculated to produce a desired therapeutic effect. The unit dosage is the formulation in which the active agent is delivered. When a unit dose is administered, it can be provided in any discrete unit, e.g., in the form of tablets or capsules. The dosage to be administered can vary depending upon the physical characteristics of the patient, the severity of the patient's symptoms, and the means used to administer the drug. The specific dose for a given patient is usually set by the judgment of the attending physician. The daily dosage can require 1 or a plurality of dosage units. Dosages can be e.g., about 10 ng to 10 mg daily. For example, tablets or capsules can include 10 ng-10 mg of active agent or a composition that includes 10 ng-10 mg of active agent, and a daily dosage can be 1 or more capsules per day.

For purposes of calculating dosages as provided based on the weight of a subject, average weight of 80 kg is used for a subject (which is based on an average weigh for a female subject of about 74 kg and an average weight for a male subject of about 86 kg).

B. The Role of Platelets and Health

Platelets are an important cellular component of blood involved in hemostasis. Platelets also are a factor in thrombotic and/or thromboembolic events. A normal platelet count is considered to be in the range of about 150,000 to 450,000 platelets per microliter of blood (e.g., see Sloan, J. Clin. Path. 4: 37-46 (1951)). "Normal" platelet count long has been thought to be critical to normal hemostasis. When the platelet count is low, bleeding and/or bruising readily occurs. Abnormally high platelet counts such as those that result from hematological proliferative disorders such as, for example, essential thrombocythemia, have been recognized as an important risk factor in thrombus formation. In very large numbers—exceeding 600,000 platelets per microliter of blood—platelets can cause clotting in blood vessels and abnormal bleeding. It has been accepted in the art that aspirin, which is known to inhibit cyclooxygenase and thereby prevents production of thromboxane $A_2$ in platelets, lowers the incidence of thrombotic and thromboembolic events.

For platelets, therapeutic regimens thus far reported primarily have as their aim an inhibition of platelet function (e.g., inhibition of platelet adhesion, aggregation or factor release). In certain myeloproliferative disorders and certain hematological malignancies, therapeutic regimes aim to reduce platelet count in patients with abnormally high levels to levels approximating normal levels. Therapeutic intervention for reducing platelet count to low normal or below normal levels in subjects without myeloproliferative disorders has not been proposed primarily since normal platelet count has been thought to be critical to normal hemostasis.

Conditions resulting from thrombotic or thromboembolic events are the leading causes of illness and death in adults in western civilization. For example, atherothrombosis, in which acute thrombosis occurs in regions of the vasculature already damaged by atheroma so precipitating stroke, myocardial infarction or limb ischemia, is a major cause of death and disability in the developed world. The importance of platelet aggregation in the acute thrombotic event is substantiated by the efficacy of platelet inhibitors such as aspirin and clopidogrel in reducing the incidence of such events. The relative risk reduction achieved by platelet inhibitors is only of the order of 25-30%, leaving substantial room for improvement.

Based on post hoc analysis of data, subjects, including those with normal levels of circulating platelets and those with elevated levels of circulating platelets, can derive medical benefit from a reduction in platelet count to low normal or below normal levels, without serious adverse consequences as a result of the platelet count reduction. The benefit can be proportional or correlative to the reduction in platelet count in a broad safety range. The compositions and methods provided herein are useful for reducing platelet number in a subject, including subjects with normal levels of circulating platelets, as well as subjects with elevated levels of circulating platelets, such as those with a myeloproliferative disorder.

C. Platelet-Related Conditions and Diseases

The compositions and methods provided herein can be used to treat subjects who have a platelet-related condition or disease. For example, the compositions and methods can be used in the treatment of subjects who have had a primary vaso-occlusive event in the past or who are experiencing a vaso-occlusive event, including subjects who have been diagnosed with thrombosis or as having a thrombotic event. The compositions and methods provided herein also can be used to treat subjects that manifest an abnormal healing of blood vessels or who are suffering from a myeloproliferative disorder.

1. Thrombotic Events

Thrombotic events, including thromboembolic events, can be serious medical conditions particularly since they can cause a reduction in blood flow to critical organs including the brain and myocardium. Examples of thrombotic events include, but are not limited to, arterial thrombosis, including stent and graft thrombosis, cardiac thrombosis, coronary thrombosis, heart valve thrombosis and venous thrombosis. Cardiac thrombosis is thrombosis in the heart. Arterial thrombosis is thrombosis in an artery. Coronary thrombosis is the development of an obstructive thrombus in a coronary artery, often causing sudden death or a myocardial infarction. Venous thrombosis is thrombosis in a vein. Heart valve thrombosis is thrombosis on a heart valve. Stent thrombosis is thrombosis resulting from and/or located in the vicinity of a vascular stent. Graft thrombosis is thrombosis resulting from and/or located in the vicinity of an implanted graft, particularly a vascular graft.

Examples of conditions or disorders that result from thrombotic events include, but are not limited, to myocardial infarction, stroke, transient ischemic attacks, amaurosis fugax, occluded autologous arteriovenous fistulae, thrombosis in arteriovenous (AV) fistulae, aortic stenosis, cardiac stenosis, coronary stenosis and pulmonary stenosis. Stenosis is the narrowing or stricture of a duct or canal. Coronary stenosis is the narrowing or stricture of a coronary artery. Cardiac stenosis is narrowing or diminution of any heart passage or cavity. Pulmonary stenosis is the narrowing of the opening between the pulmonary artery and the right ventricle. Aortic stenosis is narrowing of the aortic orifice of the heart or of the aorta itself. Stroke is a condition resulting from the lack of oxygen to the brain, which can result from one or more occlusive thrombi. Depending on the area of the brain affected, stroke can result in a wide range of symptoms from transient ischemic attacks to death (e.g., coma, reversible or irreversible paralysis, speech problems or dementia). The compositions and methods provided herein can be used to reduce the risk of a thrombotic event, e.g., stroke.

A subject with an abnormally elevated risk of stroke, for example non-hemorrhagic stroke, also can be treated using the compositions and/or methods provided herein. Subjects having an abnormally elevated risk of an ischemic stroke are a category determined according to conventional medical practice; such subjects can also be identified in conventional medical practice as having known risk factors for stroke or having increased risk of cerebrovascular events. The primary risk factors include hypertension, hypercholesterolemia, and smoking. Subjects having an abnormally elevated risk of an ischemic stroke also include individuals having any cardiac condition that can lead to decreased blood flow to the brain, such as atrial fibrillation, ventricular tachycardia, dilated cardiomyopathy and other cardiac conditions requiring anticoagulation. Subjects having an abnormally elevated risk of an ischemic stroke also include individuals having conditions including arteriopathy or brain vasculitis, such as that caused by lupus, congenital diseases of blood vessels, such as cadasil syndrome, or migraine, especially prolonged episodes.

The subject to be treated also can be one who is at abnormally elevated risk of a thrombotic event. The subject to be treated can be one who is prone to a thrombotic event. Included in this category of subjects are (1) those who have undergone a surgical procedure and are immobilized following such a procedure, (2) those who have chronic congestive heart failure, (3) those who have atherosclerotic vascular disease, (4) those who have malignancy other than a hematological malignancy which results in abnormally high platelet counts, and (5) those who are pregnant. A large majority of human subjects prone to thrombotic events do not manifest any observable perturbation in hemostasis.

One category of subjects with an abnormally elevated risk of a thrombotic event is those subjects who have previously experienced a primary thrombotic event. Subjects having an abnormally elevated risk of a thrombotic event also include (i) those who have inherited a disposition towards thrombosis, for example those with a family history of thrombosis related disorders, (ii) those who have acquired a risk of a thrombotic event such as surgical patients, and (iii) those who engage in lifestyle habits which are considered high risk indicators for thrombosis.

Lifestyle risk factors include smoking, failure to exercise and diet to the extent that it affects other risk factors such as obesity, high cholesterol, hyperlipidemia and high blood pressure (i.e., hypertension). High cholesterol (i.e., hypercholesterolemia), high blood pressure (i.e., hypertension), hyperlipidemia, and obesity are most certainly also induced by a variety of non-dietary causative elements including genetic and environmental factors.

A hyperlipidemic subject is defined as one whose cholesterol and triglyceride levels equal or exceed the limits set as described herein for the hypercholesterolemic and hypertriglyceridemic subjects. A hypercholesterolemic subject (i.e., one with high cholesterol) has either an LDL (i.e., low-density lipoprotein) level of >160 mg/dL, or an LDL level of >130 mg/dL and at least two risk factors selected from the group consisting of male gender, family history of premature coronary heart disease, cigarette smoking (more than 10 cigarettes per day), hypertension, low HDL (<35 mg/dL), diabetes mellitus, hyperinsulinemia, abdominal obesity, high lipoprotein (a), and a personal history of cerebrovascular disease or occlusive peripheral vascular disease. A hypertriglyceridemic subject has a triglyceride (TG) level of >250 mg/dL.

Subjects who are hypertensive (i.e., those that have high blood pressure) are also at risk of a thrombotic event. A hypertensive subject is one who experiences persistently high arterial blood pressure. Hypertension can have no known cause, in which case it is referred to as essential or idiopathic hypertension. Alternatively, hypertension can be associated with other primary diseases, in which case it is referred to as secondary hypertension. It is generally considered a risk factor for the development of heart disease, peripheral vascular disease, stroke and kidney disease. In adults, a diastolic pressure below 85 mmHg is considered normal, between 85 and 89 mmHg is considered high normal, 90 to 104 mmHg is considered mild hypertension, 105 to 114 mmHg is considered moderate hypertension and 115 mmHg or greater is considered severe hypertension. When the diastolic pressure is below 90 mmHg, a systolic pressure below 140 mmHg indicates normal blood pressure, between 140 and 159 mmHg is borderline isolated systolic hypertension and 160 mmHg or higher is isolated systolic hypertension. Thus, generally, normal subjects are those with a blood pressure of 140/90 or less.

Other risk factors that contribute to an elevated risk of thrombotic events, and the disorders which underlie such thrombotic events (e.g., arteriosclerosis), include hyperlipidemia, hyperglycemia and diabetes mellitus, stress and personality, low index of high density lipoproteins (HDL), male gender, age, hyperinsulinemia, high lipoprotein (a) and a personal history of cerebrovascular disease or occlusive peripheral vascular disease. Hyperglycemia is a condition associated with too high a level of glucose in the blood, sometimes indicative of uncontrolled diabetes. It occurs when the body does not have enough insulin or cannot effectively use insulin to metabolize glucose. This condition can be associated with diabetes mellitus, Cushing's disease, and Cushing's syndrome. Signs of hyperglycemia are significant thirst, dry mouth, and frequent urination.

2. Vaso-Occlusive Events

Vaso-occlusive events include disorders in which the blood vessel narrowing results not necessarily from a thrombus but rather a thickening of the vessel wall such as with intimal hyperplasia. Intimal hyperplasia refers to a condition characterized by abnormal proliferation of the cells of the intimal layer of the blood vessel wall. Intimal hyperplasia is the body's response to an injury of a blood vessel. Intimal hyperplasia is a leading cause of arteriovenous graft failures and is associated with occlusive vascular graft disease. Intimal hyperplasia also has been suggested as a cause of accelerated atherosclerosis in subjects having coronary bypass grafts. Intimal hyperplasia also has been identified as a causal factor of restenosis.

The compositions and methods provided herein can be used to reduce the risk of a primary or a secondary vaso-occlusive event such as a thrombotic event or to inhibit the progression of such an event. The compositions and methods provided herein also can be used to treat subjects at abnormally elevated risk of experiencing particular vaso-occlusive events. For example, a subject with an abnormally elevated risk of myocardial infarction can be treated with the compositions or methods provided herein. Subjects can be treated prophylactically to reduce the risk of a primary or secondary myocardial infarction. This includes treating subjects with unstable angina, multiple coronary risk factors, and Prinzmetal's variant angina, as well as having any of the less common etiologic factors, including hypercoagulability, coronary emboli, collagen vascular disease, and cocaine abuse.

The compositions and methods provided herein can be used to reduce the risk of intimal hyperplasia as well as to treat a subject that has intimal hyperplasia. In the methods provided herein, a subject at risk of developing intimal hyperplasia or having intimal hyperplasia is administered a controlled release composition provided herein that delivers a platelet number reducing agent in an amount effective to reduce platelet count from at least 10% to at least 95% of pre-treatment levels. In some embodiments, the controlled release compositions including a platelet number reducing agent as described herein are administered in an amount effective to reduce platelet count by at least 20%, at least 30%, at least 40%, at least 50%, at least 60%, at least 70%, at least 80%, or at least 90% of pre-treatment levels.

3. Vascular Disease

Another category of subjects with an abnormally elevated risk of thrombosis is those subjects having vascular disease. Vascular disease is a term that broadly encompasses all disorders of blood vessels (collectively known as the vasculature) including small and large arteries and veins, and blood flow. The most prevalent form of vascular disease is arteriosclerosis, a condition associated with the thickening and hardening of the arterial wall. Arteriosclerosis or an arteriosclerotic condition as used herein means classical atherosclerosis, accelerated atherosclerosis, atherosclerosis lesions and any other arteriosclerotic conditions characterized by undesirable endothelial and/or vascular smooth muscle cell proliferation, including vascular complications of diabetes. It is responsible for the majority of deaths in the United States and in most westernized societies.

Arteriosclerosis of the large vessels is referred to as atherosclerosis. Atherosclerosis is the predominant underlying factor in disorders such as coronary artery disease, aortic aneurysm, arterial disease of the lower extremities and cerebrovascular disease. Other types of arteriosclerosis include focal calcific arteriosclerosis (Mönckeberg's sclerosis) and arteriolosclerosis. Arterial diseases other than arteriosclerosis include congenital structural defects, inflammatory or granulomatous diseases (e.g., syphilitic aortitis), and small vessel disorders such as hypertension and autoimmune diseases. Disorders which are associated with early arteriosclerosis include diabetes mellitus, hypertension, familial hypercholesterolemia, familial combined hyperlipidemia, familial dysbetalipoproteinemia, familial hypoalphalipoproteinemia, hypothyroidism, cholesterol ester storage disease, systemic lupus erythematosus, homocysteinemia, chronic renal insufficiency, chronic vitamin D intoxication, pseudoxanthoma elasticum, idiopathic arterial calcification in infancy, aortic valvular calcification in the elderly and Werner's syndrome.

Subjects with cardiovascular disease, cerebrovascular disease and/or peripheral vascular disease (e.g., diabetic feet, failed grafts) are also considered at abnormally high risk of a thrombotic event. Cardiovascular disease refers to a number of disorders of the heart and vascular system. Cerebrovascular disease refers to a number of disorders of the blood vessels in the cerebrum of the brain. Peripheral vascular disease encompasses disorders of the peripheral vasculature including that of the lower extremities.

Another category of subjects with an abnormally elevated risk of a thrombotic event are those subjects who will undergo or those who have already undergone a surgical or mechanical interventional procedure for the purposes of vessel repair and/or revascularization. Such procedures can be therapeutic or diagnostic in nature, and thus can also be elective or emergency treatments, and most likely involve the risk of formation of thrombi or the release of emboli. Procedures which fall into this category include but are not limited to vascular surgery including peripheral vascular surgery, vascular grafting, vascular laser therapy, vascular replacement, including prosthetic valve replacement, and vascular stenting, ventricular assist procedures, artificial heart transplant, heart and other organ transplants which require an interfacing of the transplanted organ with the vasculature of the transplant recipient, thrombectomy, coronary angiography, coronary and peripheral stent placements, carotid artery procedures including carotid endarterectomy, brain angiography, neurosurgical procedures in which blood vessels are compressed or occluded, cardiac catheterization, vascular angioplasty, including balloon angioplasty, coronary angioplasty, percutaneous transluminal coronary angioplasty, subintimal angioplasty, superficial femoral artery (SFA) angioplasty, SFA remote endarterectomy, and coronary by-pass surgery. In addition to the risk of thrombus formation during or immediately following the surgical procedure, there also exists a risk to subjects who have undergone a surgical procedure and are currently immobilized following the procedure. Thus the compositions and methods provided herein are intended to treat a subject prior to, during and following surgical procedures.

Other factors which predispose subjects to abnormally elevated risk of a thrombotic event are genetic risk factors and lifestyle habits. Inherited conditions can generally be regarded as hypercoagulable states or pre-thrombotic states. The pre-thrombotic subject can sometimes be identified if they present with a personal history of early (i.e., adolescent or as a young adult) and/or repeated thromboembolic events in the absence of an overt pre-disposing condition, and/or a family history of thrombosis related conditions. Subjects who have experienced pain in walking, ischemia (i.e., a deficiency of blood flow to an area of the body due to functional constriction or obstruction of a blood vessel), gangrene (i.e., a death of tissue, usually considerable in mass and generally associated with loss of blood flow), claudication (i.e., a muscle pain, ache, cramp, numbness or sense of fatigue in the lower leg while walking or exercising, which usually subsides with rest, often caused by blocked arteries in the leg), critical limb ischemia (i.e., an obstruction of the arteries to the extremities that seriously decreases the flow of blood, resulting in chronic ischemic pain, unhealing sores and ulcers, gangrene and ultimately limb loss), and chest pain, can be regarded as having a personal history of arterial thrombosis or stroke, and are thus also at risk of a thrombotic event. Risk factors for a thrombotic event also include inheritable hematological abnormalities such as deficiency and/or dysfunction in any number of factors including anti-thrombin III, protein C, protein S and clotting factor V. Cardiovascular abnormalities, i.e., congenital structural abnormalities of the cardiovascular system, are also considered risk factors for thrombotic events. Vascular abnormalities such as atherosclerotic plaque ruptures are also considered a risk factor.

The compositions and methods provided herein can be used to reduce the risk of vascular disease as well as to treat a subject that has vascular disease. In the methods provided herein, a subject at risk of developing vascular disease or having vascular disease is administered a controlled release composition provided herein that delivers a platelet number reducing agent in an amount effective to reduce platelet count from at least 10% to at least 95% of pre-treatment levels. In some embodiments, the controlled release compositions including a platelet number reducing agent as described herein are administered in an amount effective to reduce platelet count by at least 20%, at least 30%, at least 40%, at least 50%, at least 60%, at least 70%, at least 80%, or at least 90% of pre-treatment levels.

4. Myeloproliferative Disorders

The compositions and methods provided herein can be used to treat subjects who have myeloproliferative disorder or disease. A number of pathological conditions or processes are mediated in part by high levels of circulating platelets, such as those resulting from proliferative disorders, such as myeloproliferative disorders. Myeloproliferative disorders encompass a group of diseases in which the bone marrow makes too many red blood cells, white blood cells, and/or platelets. Myeloproliferative disorders include slow growing blood cancers in which large numbers of abnormal red blood cells, white blood cells, or/or platelets grow and spread in the bone marrow and the peripheral blood. Myeloproliferative disorders in which platelet number is elevated include, e.g., polycythemia vera, idiopathic myelofibrosis and essential thrombocythemia or essential thrombocytosis. Subjects suffering from such disorders having high numbers of platelets can be treated using the compositions and methods provided herein to lower platelet count a near normal or normal level. A somatic point mutation of the JAK-2 gene (an acquired V617F mutation) has been identified to be highly associated with classic myeloproliferative disorders (MPD) (e.g., see Campbell et al., Lancet 366: 1945-1953 (2005)). The V617F mutation is prevalent in subjects diagnosed with polycythemia vera, and also is found in subjects diagnosed with essential thrombocythemia and idiopathic myelofibrosis (Wagstaff et al., Drugs 66(1): 111-131 (2006)). The JAK-2 mutation appears to indicate a differential risk profile in subjects. The value of using the JAK-2 V617F mutation status of a subject as a risk factor for thrombosis in patients with myeloproliferative disorders is being investigated (e.g., see Vannucchi et al., Leukemia 21: 1952-1959 (2007) and Finazzi et al., Haematologica 92: 135-136 (2007)).

a. Essential Thrombocythemia

An exemplary proliferative disorder mediated in part by high levels of circulating platelets is essential thrombocythemia (ET). Essential thrombocythemia is a hyperproliferative disease of the bone marrow, which is characterized by an increased number of platelets (thrombocytes) in the blood. Essential thrombocythemia is defined as thrombocytosis of more than $600 \times 10^9$/L, often $1,000 \times 10^9$/L or higher, and a megakaryocytic hyperplasia in the bone marrow, according to the World Health Organization (WHO) criteria. Involvement of platelets in essential thrombocythemia is reported in Seminars in Hematology 42(4): 230-238 (2005)) and also in New Eng. J. Med. 353:1, 33-45 (2005). Thromboembolic events are a major cause of death in this patient group. There is evidence that a strict control of the platelet count decreases the incidence of thromboembolic complications.

ET is one of a number of chronic myeloproliferative disorders characterized by an elevated platelet count due to an autonomous clonal proliferation of bone marrow megakaryocytes. The underlying cause of this proliferation is unknown, but changes in the microenvironment of the bone marrow in addition to alterations in the cellular and extracellular cytokine levels have been proposed to play an important role (Tefferi, N. Engl. J. Med. 342: 1255-1265 (2000)).

A number of clinical complications associated with thrombocythemia are known. These include angina, cardiac infarction, capillary occlusion, pulmonary embolism, stroke and thrombosis. Thrombocythemia also is known to precipitate vasomotor symptoms including headache and visual disturbance. Subjects with thrombocythemia can be afflicted with the condition for several years, and although the condition does not appear to affect life expectancy, vascular complications, including arterial and venous thrombosis, can result in the death of the subject.

A number of therapies for reducing high platelet count in myeloproliferative disorders have been developed. These include physical methods, such as plateletpheresis and differential centrifugation, as well as pharmaceutical therapies. For example, therapies for the treatment of ET (essential thrombocythemia) to reduce platelet count include treatment with hydroxycarbamide (previously called hydroxyurea), anagrelide, often in combination with low-dose acetylsalicylic acid, and in some populations interferon-busulphan and pipobroman (e.g., see De Stefano et al., Haematologica 93(3): 372-380 (2008); Barbui & Finazzi, N Engl J Med 353(1): 85-86 (2005); Barbui & Finazzi, Blood Reviews 19(5): 243-252 (2005); Wagstaff & Keating, Drugs 66 (1): 111-131 (2006); Barbui & Finazzi, Blood 109(12): 5104-5111 (2007); Najean et al., Blood, 90(9): 3370-3377 (1997). Diagnostic guidelines for diagnosing and treating myeloproliferative diseases are known in the art (e.g., see Barbui et al., Haematologica 89(2): 215-232, McMullin et al., Br J Haem 130: 174-175 (2005); Nordic MPD Study Group, "Guidelines for the diagnosis and treatment of patients with polycythemia vera, essential thrombocythemia and idiopathic myelofibrosis," (2007); Barbui & Finazzi, N Engl J Med 353(1): 85-86 (2005); and Tefferi & Vardiman, Leukemia 22: 14-22 (2008)).

Treatment regimes for this condition include administration of hydroxycarbamide (also known as hydroxyurea) and other alkylating agents. Hydroxycarbamide is an anti-neoplastic drug that suppresses the production of blood cell precursors in the bone marrow. Hydroxycarbamide acts directly on hematopoietic stem cells and therefore is not specific for reducing platelet number (e.g., see Petrides, Expert Opin Pharmacother 5(8): 1781-1798 (2004)). Hydroxycarbamide generally is used in subjects if no other alternative is available. In high risk subjects, hydroxycarbamide is widely used, sometimes in combination with low-dose aspirin. Known side-effects are GI complications, skin alterations (including tumors) or pneumonitis. Patients treated with hydroxycarbamide as monotherapy have a low (3-6%) risk of leukemic transformation (e.g., see Cortelazzo et al., New Eng J Med 332: 1132-1136 (1995), Andersson et al., Ann Hematol 79: 40-42 (2000), and Finazzi et al., Br J Haematol 110: 577-583 (2000)). IFN- is a more recent therapeutic agent for the treatment of ET but it is expensive, must be administered as an injectable drug and its acute side effects (e.g., fatigue, depression, influenza-like symptoms, elevated liver enzymes, anorexia, alopecia, neuropsychiatric symptoms) lead to its discontinuation in a significant number of patients (Samuelsson et al., Cancer 106(11): 2397-2405 (2006) and Fruchtman, Leuk Res. 29: 481-491 (2005)). Busulfan and pipobroman, alkylating anti-neoplastic agents with known carcinogenic potential, also can be used to treat ET.

b. Polycythemia Vera

Another exemplary proliferative disorder mediated in part by high levels of circulating platelets is polycythemia vera (PV). Involvement of platelets in polycythemia vera is reported in the art (e.g., see Seminars in Thrombosis and Hemostatis 32(3): 267-275 (2006)). Polycythemia vera is a chronic myeloproliferative disorder. Polycythemia vera is a clonal, acquired disease of the hematopoietic stem cell that causes the overproduction of hematopoietic cells, including red blood cells and platelets. Platelet count in subjects with polycythemia vera often is greater than $400 \times 10^9$/L, in some instances greater than $1,000 \times 10^9$/L (e.g., see Turgeon, *Clinical Hematology: Theory and Procedures*, $4^{th}$ ed., Lippincott Williams & Wilkins (2004), p. 313).

c. Idiopathic Myelofibrosis

Another exemplary proliferative disorder that is mediated in part by high levels of circulating platelets is idiopathic myelofibrosis. Idiopathic myelofibrosis is a clonal, acquired disease of the hematopoietic stem cell, usually beginning with an abnormal change in the DNA of a single hematopoietic stem cell in the marrow (e.g., see *Idiopathic Myelofibrosis*, The Leukemic & Lymphoma Society, No. 14 (2007). Production of abnormal cells may replace normal cell production, and a progressive fibrosis or scarring of the bone marrow occurs, reducing its ability to produce blood cells. In compensation, blood cells are produced in other organs, such as the spleen and the liver, which are not as efficient as blood marrow in producing blood cells. In idiopathic myelofibrosis, excessive megakaryocytes, the cells that produce platelets, are produced, usually with the concurrent release of cytokines in the bone marrow. The excess of cytokines in the bone marrow can stimulate the production of fibrous tissue in the bone marrow. Platelet count in subjects with idiopathic myelofibrosis often is greater than $600 \times 10^9$/L.

5. Other Conditions

It has been shown that in subjects with coronary artery disease, the quantity of residual thrombus after fibrinolysis and the frequency of coronary events after percutaneous intervention can be correlated with the baseline platelet count (e.g., see Stone et al., N Eng J Med 346: 957-966 (2002) and Nikolsky et al., Am J Cardiol. 99(8): 1055-1061 (2007)). It has been demonstrated that the risk of atherothrombotic events tends to increase as platelet count increases. Hence, a reduced platelet count to within the normal or low normal range or below in subjects at risk of atherothrombotic events can lead to a reduction in those events.

In addition, in situations where it is desirable to inhibit a pathological condition or process mediated in part by normal levels of circulating platelets, subjects can be treated to lower platelet count to a low normal level or below normal level, thereby inhibiting the development, progression or propagation of the condition or accelerating or enhancing its regression. Reducing the number of platelets also results in a reduction of the incidence of abnormal vessel growth induced by the presence of platelets.

Further, atherothrombotic events in the coronary, cerebral and peripheral circulation are leading causes of death and disability in the developed world and the prevalence of these events is increasing as the so-called "western lifestyle" with its associated high levels of hypertension, obesity, diabetes mellitus and dyslipidemia spreads globally (see, e.g., Grant, Br J Diabetes Vasc Dis 2: 347-348 (2002), Lopex et al., Nat Med 4:1241-1243 (1998) and Kannel et al., Circulation 59: 8-13 (1979)). Platelets are known to play a major role in the pathogenesis of atherothrombosis as evidenced by the efficacy of anti-platelet agents such as aspirin and clopidogrel in reducing the incidence of such events in a variety of clinical circumstances (see, e.g., Antithrombotic Trialists' Collaboration, BMJ 324: 71-86 (2002), CAPRIE Steering Committee, Lancet 348: 1329-1339 (1996), Gerschutz et al., Cleveland Clinic J Med 69: 377-385 (2002); Kneid et al., Arch Intern Med. 163: 1145-1153 (2003), Yusuf et al., N Engl J Med. 345: 494-502 (2001). Even when the major mechanisms involved in platelet aggregation are addressed using combination therapy with aspirin (to inhibit thromboxane $A_2$ production and to inhibit the cyclooxygenase pathway) and clopidogrel (to inhibit adenosine diphosphate-induced platelet aggregation pathways and to block the P2Y12 receptor) the reduction in cardiovascular events is only of the order of 25-30% and there is an associated increase in bleeding that can be serious and even life-threatening. Other exemplary conditions or disorders that can benefit from a reduction in the number of circulating platelets include sticky platelet syndrome, peripheral vascular diseases, including peripheral arterial disease, acute coronary syndrome, intermittent claudication, and ischemias, including bowel ischemia, cardiac ischemia, cerebral ischemia, colonic ischemia, critical limb ischemia, intestinal ischemia, lung ischemia-reperfusion injury (LIRI), mesenteric ischemia, renal ischemia and retinal ischemia.

D. Anagrelide

An agent that reduces platelet number is anagrelide. Anagrelide (6,7-dichloro-1,5-dihydroimidazo-[2,1-b]quinazolin-2(3H)-one) is an oral imidazoquinazoline originally developed as an inhibitor of platelet aggregation but subsequently found to have value as a platelet number reducing agent for the treatment of patients suffering from ET. Anagrelide exists as the free base and as a salt form, usually the hydrochloride monohydrate, although other salt forms exist. The hydrochloride monohydrate (6,7-dichloro-1,5-dihydroimidazo-[2,1-b]quinazolin-2(3H)-one mono-hydrochloride monohydrate) is marketed under the trademark AGRYLIN® in the United States and Canada and under the trademark XAGRID® in Europe. In the U.S., anagrelide is indicated for the reduction of elevated platelet counts and the amelioration of thrombohemorrhagic events in patients with thrombocythemia associated with myeloproliferative disorders. In Europe, anagrelide is indicated for the reduction of elevated platelet counts in at-risk patients with essential thrombocythemia who are intolerant to their current therapy or whose elevated platelet counts are not reduced to an acceptable level by their current therapy.

Anagrelide is a selective thrombocyte-reducing agent (e.g., see Pescatore et al., Expert Opin Pharmacother 1(3): 537-546 (2000)). In patients with essential thrombocythemia, a dosage of the immediate release form of 3 mg/day, which can be administered in divided doses, will, after the circulating platelet pool has turned over once, i.e., after approximately 10 days, result in a decrease in the number of circulating platelets of approximately 30-50 percent, indicating that anagrelide modulates megakaryocytopoiesis.

1. Chemistry

Anagrelide is an imidazoquinazoline that is sparingly soluble in dimethylsulfoxide and N,N-dimethylformamide and very slightly soluble in water. Anagrelide is insoluble in diethyl ether or n-heptane. Anagrelide can be made using any of the processes known in the art (e.g., see U.S. Pat. Nos. 3,932,407; 4,146,718; 4,208,521; 4,357,330; Re 31,617; 5,801,245, and 6,388,073 and WO/2002/008228). Commercially, as discussed in U.S. Pat. No. 5,801,245, anagrelide has been prepared as the hydrochloride monohydrate from the intermediate, ethyl N-(6-amino-2,3-dichlorobenzyl)glycine by reaction with cyanogen bromide in hot alcohol solution, or, preferentially, by reaction with cyanogen bromide (CNBr) in an aprotic solvent to give the iminoquinazoline intermediate, which is isolated and then reacted with a base in a hot solution of alcohol to form anagrelide base. For example, anagrelide can be prepared as shown in Scheme I below, by treating ethyl 2-(6-amino-2,3-dichlorobenzyl-amino)acetate with CNBr in toluene under reflux to produce ethyl 2-(5,6-dichloro-2-imino-1,2-dihydroquinazolin-3(4H)-yl)acetate, which, when treated with triethylamine in ethanol under reflux, yields anagrelide free base. The free base can be converted to anagrelide hydrochloride monohydrate by appropriate treatment with HCl. The CAS® Registry Number for anagrelide monohydrochloride is 58579-51-4.

6,7-dichloro-3-hydroxy-1,5-dihydro-imidazo[2,1-b]quinazolin-2-one 3-hydroxy-anagrelide

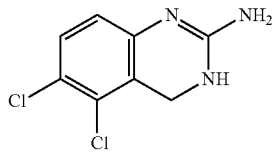

2-amino-5,6-dichloro-3,4-dihydroquinazoline

In a study of patients with essential thrombocythemia (ET) or other myeloproliferative diseases, 3-hydroxy anagrelide

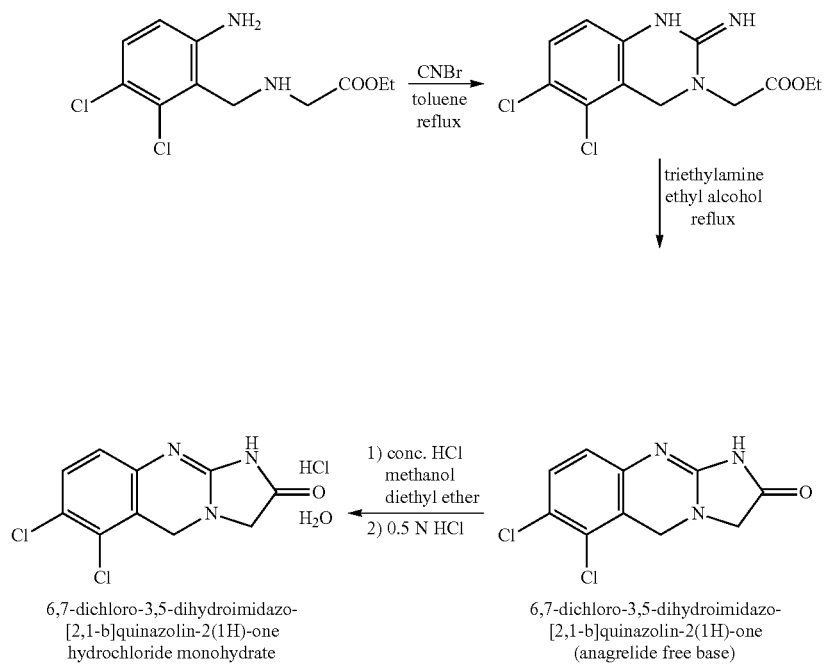

Anagrelide (free base and hydrochloride monohydrate) is commercially available (e.g., Shire plc, Wayne, PA; Ash Stevens, Inc., Riverview, MI; Hallochem Pharmaceutical Co., Ltd., Sichuan, China; and Cipla Ltd., Bangalore, India).

2. Metabolites

Anagrelide is extensively metabolized in man to two major metabolites: 3-hydroxy anagrelide (6,7-dichloro-3-hydroxy-1,5-dihydro-imidazo[2,1-b]quinazolin-2-one, also known as BCH24426 and SPD604 and referred to as 3-HA) and a subsequent bio-transformation product 2-amino-5,6-dichloro-3,4-dihydroquinazoline (also known as RL603):

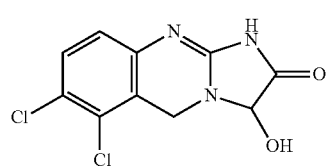 [SMILES: O=C1NC2=Nc3ccc(Cl)c(Cl)c3CN2C1O]

(3-HA) was found to be the major circulating component in blood representing about 45% of all drug-related products in the plasma. The other metabolite (RL603) constituted about 33% of the plasma components in these patients. Anagrelide itself represented less than about 20% of the plasma constituents. The observed half-life for anagrelide was about 1.7 h, followed by 3-HA with a half-life of 3.9 and finally RL603 with a half-life of 8.7 h. (Summary of Shire data on file with the FDA, entitled "Attachment G: Evidence for the primary role of anagrelide's major metabolite, 3-hydroxy anagrelide in the drug's clinical activity, available, for example, at the website: fda.gov/ohrms/dockets/dailys/04/aug04/081604/04p-0365-cp0000'-08-Tab-G-vol1.pdf).

3-Hydroxy anagrelide is equipotent with anagrelide in its in vitro effects on megakaryocytopoiesis and therefore potentially platelet lowering but it is 40 times more potent as a PDEIII inhibitor and therefore as an inotrope, chronotrope and vasodilator. The further metabolite RL603 is essentially inactive.

3. Derivatives and Analogs of Anagrelide

Analogs and derivatives of anagrelide have been reported by a number of groups. Jones et al. reports the synthesis of an analog, RS-82856 (N-cyclohexyl-N-methyl-4-(7-oxy-1,2,3,5-tetrahydroimidazo-[2,1b]quinazolin-2-one (Jones et al., J. Med. Chem. 30:295-303 (1987)). Derivatives of anagrelide synthesized by directed replacement of side chains on anagrelide also have been reported (e.g., see Meanwell et al., J. Med. Chem. 35:2672-2687 (1992)). Other anagrelide analogs have been described in U.S. Pat. Nos. 3,932,407; 4,146,718 and RE31,617. For example, Beverung, Jr. et al. (U.S. RE31,617 (1984)) discloses optionally substituted 1,2,3,5-tetrahydroimidazo[2,1-b]-quinazolin-2-ones and 6(H)-1,2,3,4-tetrahydropyrimido-[2,1-b]quinazolin-2-ones. These include 1,2,3,5-tetrahydroimidazo-[2,1-b]-quinazolin-2-one, 7-bromo-1,2,3,5-tetrahydro-imidazo[2,1-b]-quinazolin-2-one, 7-nitro-1,2,3,5-tetrahydroimidazo[2,1-b]-quinazolin-2-one, 7-amino-1,2,3,5-tetrahydro-imidazo-[2,1-b]-quinazolin-2-one, 6-hydroxy-1,2,3,5-tetrahydroimidazo-[2,1-b]-quinazolin-2-one, 7-hydroxy-1,2,3,5-tetrahydroimidazo-[2,1-b]-N-quinazolin-2-one, 8-bromo-6-[H]-1,2,3,4-tetrahydroimidazo[2,1-b]-quinazolin-2-one, 6-methyl-7-nitro-1,2,3,5-tetrahydroimidazo[2,1-b]-quinazolin-2-one, 7-bromo-6-methyl-1,2,3,5-tetrahydro-imidazo[2,1-b]-quinazolin-2-one, 7-chloro-6-methyl-1,2,3,5-tetrahydro-imidazo[2,1-b]-quinazolin-2-one, 6-chloro-7-bromo-1,2,3,5-tetrahydroimidazo[2,1-b]-quinazolin-2-one, 6,7-dichloro-1,2,3,5-tetrahydro-imidazo[2,1-b]-quinazolin-2-one, 7-amino-6-methyl-1,2,3,5-tetrahydro-imidazo[2,1-b]-quinazolin-2-one, 7-amino-6-methyl-1,2,3,5-tetrahydroimidazo[2,1-b]-quinazolin-2-one, 6-methyl-1,2,3,5-tetrahydro-imidazo[2,1-b]-quinazolin-2-one, 3-(carboxymethyl)-3,4-dihydro-5-methyl-4-methylene-1H-quinazolin-2-one, 3-(carboxymethyl)-4,5-dimethyl-1,2,3,4-tetrahydroquinazoline-2-one, 2-chloro-3-carbethoxymethyl-4,5-dimethyl-3,4-dihydro-quinazoline, 5,6-dimethyl-1,2,3,5-tetrahydro-imidazo[2,1-b]-quinazolin-2-one, 3-(carbethoxy-methyl)-3,4-dihydro-6-methylene-1H-quinazolin-2-one, 3-(carbethoxymethyl)-4,6-dimethyl-1,2,3,4-tetrahydro-quinazolin-2-one, 2-chloro-3-carbethoxymethyl-4,6-dimethyl-3,4-dihydroquinazoline, 5,7-dimethyl-1,2,3,5-tetrahydroimidazo-[2,1-b]-quinazolin-2-one, 5-methyl-3-(carbethyoxy-methyl)-1,2,3,4-tetrahydroquinazolin-2-one, 2-chloro-3-carbethoxymethyl-5-methyl-3,4-dihydroquinazoline hydrochloride and 6-methyl-1,2,3,5-tetrahydroimidazo-[2,1-b]-quinazolin-2-one.

All the aforementioned metabolites, analogs and/or derivatives of anagrelide are suitable for use in the compositions and methods provided herein to reduce platelet count in a subject, either to near normal or normal levels in subjects that have high platelet counts, or to a low normal or below normal level in subjects having normal platelet counts with the purpose of preventing or treating a vaso-occlusive event. In some instances these benefits are achieved by reducing the platelet count to low normal while in other instances the platelet count is reduced to below normal levels.

4. Pharmacokinetic Properties

The pharmacokinetics of anagrelide in humans are linear in the 0.5-2 mg dose range. After oral administration of the marketed immediate release formulation, anagrelide is rapidly absorbed to about 70% in the gastrointestinal tract and the drug is metabolized, mainly during first pass, to the two main metabolites, the active 3-hydroxy anagrelide and the inactive 5,6-dichloro-3,4-dihydroquinazol-2-yl amine. Another subsequent urinary metabolite of anagrelide N-(5,6-dichloro-3,4-dihydroquinazalin-2-yl)-2-oxoacetamide. In fasted subjects, peak plasma levels occur about 1 hour after a 0.5 mg immediate release dose. Dose proportionality has been found in the dose range of about 0.5 mg to 2 mg. Anagrelide is primarily metabolized by CYP1A2; less than 1% is recovered in the urine as anagrelide.

The terminal half-lives of anagrelide when administered in the commercially available instant release formulation and the active metabolite 3-hydroxy anagrelide are 1.7 and 3.9 hours. Individual titration of anagrelide dosages allows the effects of age or hepatic or renal impairment to be taken into consideration. Anagrelide specifically, reversibly and dose-dependently blocks the maturation of late-stage megakaryocytes, thus reducing platelet counts in subjects. The drug appears to normalize platelet coagulant function, does not stimulate myelofibrotic progression and, unlike hydroxyurea, is not associated with angio-genesis or damage to DNA. The inhibitory effect of anagrelide, and the 40-fold more potent 3-hydroxy anagrelide metabolite, on phosphodiesterase, including PDEIII, results in positive inotropic effects and potential for pharmacodynamic interactions with other PDE inhibitors (Gisslinger, Semin Thromb Hemost 32: 430-436 (2006)). There is evidence that anagrelide also interferes with the activation of the thrombopoietin (TPO) receptor (Petrides, Semin Thromb Hemost. 32(4): 399-408 (2006)). Anagrelide is thought to act by interfering with the effect of thrombopoietin on megakaryocyte production of platelets, thereby reducing platelet number. Other effects of anagrelide are described in the art (e.g., see U.S. Pat. Nos. 3,932,407 and 4,146,718).

Anagrelide inhibits and is metabolized by cytochrome P450 1A2 (abbreviated CYP1A2), a member of the cytochrome P450 mixed-function oxidase system. The inhibition occurs at much higher levels than those expected at therapeutic exposure (about 900-fold) and is therefore considered not relevant for the clinical exposure. The presence of the human metabolites (RL603 and SPD604) in rat and dog plasma confirms, from a metabolic perspective, the suitability of these species as appropriate toxicological models for human safety evaluation. No drug-drug interactions were identified between anagrelide and hydroxycarbamide or aspirin.

5. Mechanism of Action

Anagrelide reduces platelet count by a direct effect on the megakaryocyte believed to involve inhibition of TPO-induced signalling through the c-Mpl receptor, which is encoded by the c-mpl gene. In vitro studies of cultured megakaryocytes have demonstrated that the inhibition effects of anagrelide on the TPO/c-Mpl system occur at very low concentrations of anagrelide. Anagrelide and its 3-hydroxy metabolite also inhibit phosphodiesterase, including phosphodiesterase III and V. The most common drug-related adverse events (headache, palpitations, fluid retention, nausea and diarrhea) are believed to be due to the inhibition of cyclic AMP phosphodiesterase III and/or cyclic GMP phosphodiesterase V. Adverse events generally are dose-dependent and associated with PDE effects including vasodilation with a direct positive ionotropic effect. These effects are primarily mediated through the increase in cAMP and/or cGMP. Palpitations, tachycardia and cardiac arrhythmia are the most commonly reported cardiovascular adverse events. Other adverse events associated with vasodilation include nausea, vomiting and headaches. Another adverse event specifically related to increases in cGMP is visual disturbance. In total, the vast majority of the reported adverse effects with the use of anagrelide can be attributed to PDE inhibitory activity.

The compositions provided herein exploit the fact that separate mechanisms of action exist for anagrelide and its active metabolite—one that exhibits its effects on the cellular levels of cAMP and cGMP through the effects on phosphodiesterase and a second that is produced through an as yet not completely defined mechanism involving the TPO-induced stimulations of megakaryocytes. The compositions provided herein regulate the platelet number reducing agent to a restricted plasma concentration range effective for reducing circulating platelet number without overtly causing clinical symptoms that prevent or limit therapeutic use of the anagrelide, 3-OH anagrelide or a derivative or analog thereof.

The marketed formulation known in the art is an immediate release formulation. The pharmacokinetics of the immediate release formulation is characterized by the production of a very sharp plasma peak, followed by rapid distribution and elimination phases. In the immediate release formulations, peak plasma concentrations occur 1 hour after administration to fasting subjects and then decline rapidly. Although cytochrome P450 metabolism has been identified involving the CYP1A2 isozyme and anagrelide is excreted in the feces (approximately 10% of $^{14}C$ labelled anagrelide in humans), the molecule is mainly eliminated via the kidneys (>70% of $^{14}C$ labelled anagrelide in humans) as either the parent compound (<1%), or as one of two major urinary metabolites, 2-amino-5,6-dichloro-3,4-dihydroquinazoline and N-(5,6-dichloro-3,4-dihydroquinazalin-2-yl)-2-oxoacetamide. Several studies have identified that the parent compound and the 3-OH plasma metabolite are active against the PDE III enzyme and the TPO-induced stimulation of megakaryocytes. Another plasma metabolite, RL603, is believed inactive in either pharmacological system.

In vitro studies of cultured megakaryocytes have demonstrated that TPO inhibition effects with anagrelide are seen at very low concentrations (0.01-5 µg/mL, equivalent to 0.032-0.16 µM at 310.55 g/mol) and that higher concentrations did not produce greater response. Ex vivo studies for the inhibition of cAMP and cGMP PDE activities using sonicated human platelets demonstrated anagrelide $IC_{50}$ concentrations of 0.054 and 34 µM, respectively. Further, in vivo studies with anagrelide in several models suggest that the PDE III inhibition effects occur at greater plasma concentrations (effective oral doses of 0.1 mg-100 mg/kg).

The compositions provided herein provide a pharmacokinetic profile of anagrelide and its metabolites and pharmaceutically acceptable salts, derivatives and analogs, to reduce the peak plasma concentration ($C_{max}$) while generating effecting serum concentration and maintaining sustained exposure (area under the concentration-time curve, AUC) of the active ingredient. The compositions provided herein retain the platelet lowering effect while reducing the often intolerable adverse effect profile. For example, the controlled release (CR) compositions as described herein including anagrelide were compared with a marketed immediate release formulation of anagrelide (XAGRID®) in a single dose cross-over study at a dose of 0.5 mg. The CR compositions provided herein demonstrate lowered $C_{max}$ while minimizing inter-subject variability.

The compositions provided herein exploit the differences in the effective concentrations between the two pharmacological systems that are affected by anagrelide and the active metabolite, 3-OH anagrelide. The compositions provided herein exploit the fact that separate mechanisms of action exist for anagrelide—one that exhibits its effects on the cellular levels of cAMP and cGMP through the effects on phosphodiesterase, and a second that is produced through an as yet not completely defined mechanism involving the TPO receptor on megekaryocytes, thereby reducing platelet number.

E. Compositions

Provided herein are compositions for the controlled or sustained release of platelet reducing agents. Provided is a composition that includes a solid support core of a substantially water soluble, swellable or insoluble material; an optional preparatory coat, where the preparatory coat is from 0-5% by weight of the composition; a substrate layer that includes a binder and 50 µg to 10 mg of microparticles of a platelet number reducing agent, where the binder is present at a weight of 0.1-5% by weight of the composition and the platelet-reducing agent is in a form that has a shelf stability of at least three months, such as a hydrated crystal form, and at least 90% of the microparticles are 25 microns or less; a release control component effective for controlled release of the platelet number reducing agent, where the release control component is present at a weight of 0-10% by weight of the composition, such as 0.1%-10%; and an optional finishing coat and/or enteric coating, where the finishing coat and/or enteric coating is present at a weight of 0-10% by weight of the composition.

In one embodiment, the composition further includes a seal coat layer that includes a substantially water-soluble polymer on the substrate layer, where the seal coat is present at a weight of 0-10% by weight of the composition; and where the seal coat is disposed between the substrate layer and the release control component and the seal coat reduces chemical interaction between the platelet reducing agent and the release control component and/or the platelet reducing agent and the optional finishing coat.

A seal layer as described herein provides an improved composition. For example, in compositions described herein where the platelet reducing agent is in a hydrated crystal form, the hydrated crystal form of the platelet-reducing agent is substantially maintained for a shelf period of at least three months, typically six months or more. Moreover, the compositions having improved stability as described herein provide better bioavailability profiles. For example, a composition containing anagrelide monohydrate as described herein provides improved bioavailability compared to conventional controlled release formulations such as those disclosed by Burnside et al. (U.S. Patent Publication No. 2004/0062800).

In the compositions provided herein, a plasticizer can be used without reducing the stability of a dosage form containing a platelet reducing agent, such as anagrelide hydrochloride monohydrate. For example, provided herein is a composition where the release control component and/or the optional finishing layer includes a plasticizer and the seal layer reduces deleterious interactions between the platelet reducing agent and the plasticizer.

In some embodiments, the compositions provided herein include a substrate layer formed by a process that substantially maintains the hydrated crystal form of the platelet reducing agent. For example, provided herein are compositions where the platelet reducing agent is spray dried onto the solid support.

In some embodiments, the platelet reducing agent has a moisture content between 0.5% and at or about 10%. In some embodiments, the platelet reducing agent has a moisture content between at or about 1% and at or about 8%. In some embodiments, the platelet reducing agent has a moisture content between at or about 2% and at or about 7%. In some embodiments, the platelet reducing agent has a moisture content between at or about 3% and at or about 6%. In some embodiments, the platelet reducing agent has a moisture content of at least 6%. In some embodiments, the platelet reducing agent has a moisture content of 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10%.

Moisture content can be measured using any method known in the art. For example, moisture content can be measured by the Karl Fischer assay for determining water content, which is described in *Pharmacopeial Forum*, 24(1): 5438-5441 (January-February 1998). Titrimetric techniques using a Mitsubishi CA-06 Moisture Meter (Mitsubishi Chemical Corporation, Tokyo, Japan) or a Mettler DL-35 instrument using Karl-Fisher reagent also can be used. Another method for determining moisture content is thermogravimetric analysis (TGA). TGA is a measure of the thermally induced weight loss of a material as a function of the applied temperature. One skilled in the art will appreciate that other commonly used thermal analyses for measuring moisture content also can be used, such as differential scanning calorimetry.

In some embodiments, the compositions provided herein have a moisture content of at or about 0.5% to at or about 5% by weight. In some embodiments, the composition has a moisture content between at or about 1% and at or about 3%. In some embodiments, the composition has a moisture content of 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75% or 5%. In one embodiment, a composition is provided where the composition has a moisture content of at least about 5% by weight. In some embodiments, the composition has a moisture content of 2% or less.

In embodiments where the platelet reducing agent is in a hydrated crystal form, the effective moisture of the composition is sufficient to maintain the crystal water molecules in place so that the platelet reducing agent has a hydration level sufficient to maintain crystallinity of the platelet reducing agent particles. The effective moisture can be determined empirically for the specific platelet number reducing agent. In some embodiments, the composition has an effective moisture of at least 1%. In some embodiments, the compositions provided herein have an effective moisture of between 1% and 10%. In some embodiments, the compositions provided herein have an effective moisture of greater than 5%. In some embodiments, the platelet reducing agent is anagrelide hydrochloride monohydrate and the compositions have an effective moisture content of at least 6%. In some embodiments, a composition having a moisture content of between at or about 1% to at or about 3% has an effective moisture sufficient to maintain a hydrated crystalline form of a platelet reducing agent, such as anagrelide hydrochloride monohydrate, in its hydrated crystal form.

In some embodiments, the seal coat, when applied to the substrate, can be formulated to control water migration from the substrate layer. For example, the seal coat can be formulated to maintain the moisture of the platelet reducing agent in the substrate layer, e.g., by preventing loss or migration of the moisture from the substrate layer to other layers of the composition. In embodiments where the platelet reducing agent is in a hydrated crystal form, the seal coat can be formulated to maintain an effective moisture in the substrate layer such that the water of crystallization is maintained in the platelet reducing agent and the agent retains is hydrated crystal form for extended periods of time, e.g., for at least 3 months, or at least 6 months or at least 12 months or longer.

For some platelet reducing agents in a hydrated crystal form, loss of the water of crystallization can result in loss of activity or decomposition of the agent. For example, loss of the water of crystallization during mishandling or storage of anagrelide can result in hydrolysis of the lactam ring of anagrelide. The hydrolysis of the lactam ring of anagrelide presents a long-term stability problem for conventional anagrelide pharmaceutical formulations (e.g., see U.S. Pat. No. 6,388,073). The loss of the water of crystallization can result in the formation of a hemihydrate crystal form. It is known in the art that the hemihydrate of anagrelide is not as stable as the hydrochloride monohydrate crystal form. The seal coat of the composition can be used to minimize or eliminate water loss from the substrate layer, minimizing loss of the water of crystallization from the anagrelide hydrochloride monohydrate, thereby minimizing or eliminating hydrolysis of the lactam ring of the anagrelide. In some embodiments, the seal coat is formulated to minimize water migration from the substrate layer, thereby producing a localized effective moisture sufficient to maintain the crystal water molecules in place so that the platelet reducing agent has a hydration level sufficient to maintain crystallinity of the platelet reducing agent particles for extended periods of time.

The compositions provided herein have a shelf stability of at least 3 months at ambient temperature. In some embodiments, the compositions have a shelf stability at room temperature of at least 6 months. In some embodiments, the compositions have a shelf stability at room temperature of at least 12 months. The compositions provided herein also demonstrate enhanced stability under accelerated storage stability testing. In some embodiments, the compositions provided herein maintain at least 95% of the initial activity of the platelet reducing agent (as measured at the beginning of the storage period) after at least 2 months of storage of about 40° C. at about 75% relative humidity. In some embodiments, the compositions provided herein maintain at least 95% of the initial activity of the platelet reducing agent after least 3 months of storage of about 40° C. at about 75% relative humidity. In some embodiments, the compositions provided herein maintain at least 95% of the initial activity of the platelet reducing agent after least 6 months of storage of about 40° C. at about 75% relative humidity.

The platelet reducing agent can be any agent that reduces the number of circulating platelets. In one embodiment, the platelet number reducing agent is anagrelide. In some embodiments, the anagrelide is present as a hydrated crystal form. In some embodiments, the platelet reducing agent is anagrelide hydrochloride monohydrate. For example, provided herein are compositions where the substrate layer includes 1 μg to 10000 μg of microparticles of anagrelide (measured as the free base). In some embodiments, the substrate layer includes 10 μg to 1000 μg of microparticles of anagrelide. In some embodiments, the substrate layer includes 100 μg to 800 μg of microparticles of anagrelide. In some embodiments, the substrate layer includes 200 μg to 600 μg of microparticles of anagrelide.

Also provided herein are unit dosage forms, which include spheroid granules, pellets or beads that include an amount from at or about 10 ng to at or about 10000 μg of a platelet-reducing agent, where the platelet-reducing agent is present in a form that has a shelf stability of at least 3 months; where the spheroid granules, pellets or beads include a solid support core of a substantially water soluble, swellable or insoluble material; an optional preparatory coat; a substrate layer including the platelet number reducing agent; a seal coat layer that includes a substantially water-soluble polymer on the substrate layer; a release control component effective for controlled release of the platelet reducing agent; and an optional finishing coat and/or enteric coating, where the unit dosage form provides a peak plasma level of the platelet number reducing agent at least 50% lower than produced by an immediate release formulation of the platelet number reducing agent; and the seal coat is disposed between the substrate layer and the release control component and reduces chemical interaction between the platelet reducing agent and the release control component and/or the platelet reducing agent and the optional finishing coat. In one embodiment, the platelet number reducing agent is in the form of a hydrated crystal. In one embodiment, the platelet number reducing agent is provided in the form of free flowing microparticles.

Also provided herein are compositions that provide an optimal pharmacokinetic profile of the platelet number reducing agent that reduces platelet count in a subject while minimizing adverse events or side effects. In one embodiment, provided herein are compositions that provide an optimal pharmacokinetic profile of the platelet number reducing agent anagrelide or a metabolite, analog or derivative or pharmaceutically acceptable salt or prodrug thereof with a reduction of the $C_{max}$ while maintaining the platelet reducing ability of the agent. In some embodiments, the anagrelide is anagrelide hydrochloride monohydrate. In some embodiments, the platelet number reducing agent is 3-hydroxy anagrelide or a pharmaceutically acceptable salt thereof. In some embodiments, the platelet number reducing agent is a derivative or analog of anagrelide or a pharmaceutically acceptable salt thereof.

The compositions provided herein provide a plasma concentration profile that does not produce the peak/valley characteristics found in the marketed immediate release formulation, such as XAGRID® (Shire Pharmaceuticals). In some embodiments, the $C_{max}$ is 50% or less of an immediate release control formulation, such as XAGRID® (Shire Pharmaceuticals). In some embodiments, the $C_{max}$ is 25% or less of an immediate release formulation. In some embodiments, the $C_{max}$ is 50%, 45%, 40%, 35%, 30%, 25%, 20% or 15% or less of an immediate release formulation.

In some embodiments, compositions provided herein increase the duration of exposure and reduce the peak plasma concentration compared to an immediate release control formulation.

In embodiments where the platelet number reducing agent is anagrelide, e.g., the composition is designed to provide a peak plasma concentration of from at or about 100 pg/mL to at or about 5000 pg/mL of anagrelide. In some embodiments, the composition is designed to provide a peak plasma concentration of the anagrelide of from 500-4500 pg/mL. In some embodiments, the composition is designed to provide a peak plasma concentration of the anagrelide of from 600-4000 pg/mL. In some embodiments, the composition is designed to provide a peak plasma concentration of the anagrelide of from 700-3500 pg/mL. In some embodiments, the composition is designed to provide a peak plasma concentration of the anagrelide of from 800-3000 pg/mL. In some embodiments, the composition is designed to provide a peak plasma concentration of the anagrelide of from 900-2500 pg/mL. In some embodiments, the composition is designed to provide a peak plasma concentration of the anagrelide of from 1000-2000 pg/mL. In some embodiments, the composition provides a peak plasma concentration of anagrelide of 1050 pg/mL, 1100 pg/mL, 1150 pg/mL, 1200 pg/mL, 1250 pg/mL, 1300 pg/mL, 1350 pg/mL, 1400 pg/mL, 1450 pg/mL, 1500 pg/mL, 1550 pg/mL, 1600 pg/mL, 1650 pg/mL, 1700 pg/mL, 1750 pg/mL, 1800 pg/mL, 1850 pg/mL, 1900 pg/mL, 1950 pg/mL, 2000 pg/mL, 2050 pg/mL, 2100 pg/mL, 2150 pg/mL, 2200 pg/mL, 2250 pg/mL, 2300 pg/mL, 2350 pg/mL, 2400 pg/mL, 2450 pg/mL, 2500 pg/mL, 2550 pg/mL, 2600 pg/mL, 2650 pg/mL, 2700 pg/mL, 2750 pg/mL, 2800 pg/mL, 2850 pg/mL, 2900 pg/mL, 2950 pg/mL, 3000 pg/mL, 3050 pg/mL, 3100 pg/mL, 3150 pg/mL, 3200 pg/mL, 3250 pg/mL, 3300 pg/mL, 3350 pg/mL, 3400 pg/mL, 3450 pg/mL, 3500 pg/mL, 3550 pg/mL, 3600 pg/mL, 3650 pg/mL, 3700 pg/mL, 3750 pg/mL, 3800 pg/mL, 3850 pg/mL, 3900 pg/mL, 3950 pg/mL, 4000 pg/mL, 4050 pg/mL, 4100 pg/mL, 4150 pg/mL, 4200 pg/mL, 4250 pg/mL, 4300 pg/mL, 4350 pg/mL, 4400 pg/mL, 4450 pg/mL, 4500 pg/mL, 4550 pg/mL, 4600 pg/mL, 4650 pg/mL, 4700 pg/mL, 4750 pg/mL, 4800 pg/mL, 4850 pg/mL, 4900 pg/mL, 4950 pg/mL or 5000 pg/mL.

In some embodiments, the composition is designed to provide a peak plasma concentration of the anagrelide of from at or about 100 pg/mL to at or about 1000 pg/mL. In some embodiments, the composition is designed to provide a peak plasma concentration of the anagrelide of from at or about 200 pg/mL to at or about 800 pg/mL. In some embodiments, the composition provides a peak plasma concentration of anagrelide of from 250-750 pg/mL. In some embodiments, the composition provides a peak plasma concentration of anagrelide of 300-700 pg/mL. In some embodiments, the composition provides a peak plasma concentration of anagrelide of 350-550 pg/mL. In some embodiments, the composition provides a peak plasma concentration of anagrelide of 100 pg/mL, 150 pg/mL, 200 pg/mL, 250 pg/mL, 300 pg/mL, 350 pg/mL, 400 pg/mL, 450 pg/mL, 500 pg/mL, 550 pg/mL, 600 pg/mL, 650 pg/mL, 700 pg/mL, 750 pg/mL, 800 pg/mL, 850 pg/mL, 900 pg/mL, 950 pg/mL or 1000 pg/mL.

In some embodiments, the composition is designed to provide a peak plasma concentration of 3-OH anagrelide of from at or about 250 to at or about 5000 pg/mL. In some embodiments, the composition is designed to provide a peak plasma concentration of the 3-OH anagrelide of from at or about 500 pg/mL to at or about 4500 pg/mL. In some embodiments, the composition is designed to provide a peak plasma concentration of the 3-OH anagrelide of from at or about 600 pg/mL to at or about 4000 pg/mL. In some embodiments, the composition is designed to provide a peak plasma concentration of the 3-OH anagrelide of from at or about 700 pg/mL to at or about 3500 pg/mL. In some embodiments, the composition is designed to provide a peak plasma concentration of the 3-OH anagrelide of from at or about 800 pg/mL to at or about 3000 pg/mL. In some embodiments, the composition is designed to provide a peak plasma concentration of the 3-OH anagrelide of from at or about 900 pg/mL to at or about 2500 pg/mL. In some embodiments, the composition is designed to provide a peak plasma concentration of the 3-OH anagrelide of from at or about 1000 pg/mL to at or about 2000 pg/mL. In some embodiments, the composition provides a peak plasma concentration of the 3-OH anagrelide of 1050 pg/mL, 1100 pg/mL, 1150 pg/mL, 1200 pg/mL, 1250 pg/mL, 1300 pg/mL, 1350 pg/mL, 1400 pg/mL, 1450 pg/mL, 1500 pg/mL, 1550 pg/mL, 1600 pg/mL, 1650 pg/mL, 1700 pg/mL, 1750 pg/mL, 1800 pg/mL, 1850 pg/mL, 1900 pg/mL, 1950 pg/mL, 2000 pg/mL, 2050 pg/mL, 2100 pg/mL, 2150 pg/mL, 2200 pg/mL, 2250 pg/mL, 2300 pg/mL, 2350 pg/mL, 2400 pg/mL, 2450 pg/mL, 2500 pg/mL, 2550 pg/mL, 2600 pg/mL, 2650 pg/mL, 2700 pg/mL, 2750 pg/mL, 2800 pg/mL, 2850 pg/mL, 2900 pg/mL, 2950 pg/mL, 3000 pg/mL, 3050 pg/mL, 3100 pg/mL, 3150 pg/mL, 3200 pg/mL, 3250 pg/mL, 3300 pg/mL, 3350 pg/mL, 3400 pg/mL, 3450 pg/mL, 3500 pg/mL, 3550 pg/mL, 3600 pg/mL, 3650 pg/mL, 3700 pg/mL, 3750 pg/mL, 3800 pg/mL, 3850 pg/mL, 3900 pg/mL, 3950 pg/mL, 4000 pg/mL, 4050 pg/mL, 4100 pg/mL, 4150 pg/mL, 4200 pg/mL, 4250 pg/mL, 4300 pg/mL, 4350 pg/mL, 4400 pg/mL, 4450 pg/mL, 4500 pg/mL, 4550 pg/mL, 4600 pg/mL, 4650 pg/mL, 4700 pg/mL, 4750 pg/mL, 4800 pg/mL, 4850 pg/mL, 4900 pg/mL, 4950 pg/mL or 5000 pg/mL.

In some embodiments, the composition provides a peak plasma concentration of the 3-OH anagrelide of from at or about 250 pg/mL to at or about 1000 pg/mL. In some embodiments, the composition provides a peak plasma concentration of the 3-OH anagrelide of from at or about 300 pg/mL to at or about 900 pg/mL. In some embodiments, the composition provides a peak plasma concentration of 3-OH anagrelide of from at or about 350 pg/mL to at or about 850 pg/mL. In some embodiments, the composition provides a peak plasma concentration of 3-OH anagrelide of from at or about 400 pg/mL to at or about 800 pg/mL. In some embodiments, the composition provides a peak plasma concentration of 3-OH anagrelide of at or about 450 pg/mL to at or about 750 pg/mL. In some embodiments, the composition provides a peak plasma concentration of 3-OH anagrelide of at or about 500 pg/mL to at or about 700 pg/mL. In some embodiments, the composition provides a peak plasma concentration of 3-OH anagrelide of at or about 600 pg/mL to at or about 800 pg/mL. In some embodiments, the composition provides a peak plasma concentration of 250 pg/mL, 300 pg/mL, 350 pg/mL, 400 pg/mL, 450 pg/mL, 500 pg/mL, 550 pg/mL, 600 pg/mL, 650 pg/mL, 700 pg/mL, 750 pg/mL, 800 pg/mL, 850 pg/mL, 900 pg/mL, 950 pg/mL or 1000 pg/mL.

In some embodiments, the compositions provide an extended presentation of elevated levels of a platelet number reducing agent, such as anagrelide, 3-OH anagrelide or derivatives or analogs thereof. For example, in some embodiments, the controlled release compositions provided herein produce a $W_{50}$ (the width of the plasma concentration vs time curve at 50% of the $C_{max}$) that is from at or about 1.25 to at or about 5 times the $W_{50}$ of an immediate release formulation. In some embodiments, the $W_{50}$ of the controlled release composition is from at or about 3 to at or about 5 times the $W_{50}$ of an immediate release formulation. In some embodiments, the $W_{50}$ of the controlled release composition is from at or about 50% to 400% greater than the $W_{50}$ of an immediate release control. In some embodiments, the $W_{50}$ is from at or about 75% to 300% greater than an immediate release control. In some embodiments, the $W_{50}$ is from at or about 100% to 250% greater than an immediate release control. In some embodiments, the $W_{50}$ is 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, 325%, 350%, 375%, 400%, 425%, 450%, 475% or 500% greater than the $W_{50}$ of an immediate release control. In some embodiments, the $W_{50}$ of the compositions provided herein is from at or about 0.5 to at or about 10 hours. In some embodiments, the $W_{50}$ of the compositions provided herein is from at or about 0.75 to at or about 8 hours. In some embodiments, the $W_{50}$ of the compositions provided herein is from at or about 1 to at or about 6 hours. In some embodiments, the $W_{50}$ of the compositions provided herein is from at or about 7 to at or about 10 hours. In some embodiments, the $W_{50}$ of the compositions provided herein is 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75 or 8 hours.

In some embodiments, the $T_{max}$ is delayed by at or about 1 hour to at or about 6 hours. In some embodiments, the $T_{max}$ is delayed by 2 to 4 hours. In some embodiments, the $T_{max}$ is delayed by 3 to 6 hours. In some embodiments, the $T_{max}$ is delayed by 2 to 3 hours. In some embodiments, the compositions provided herein provide release characteristics that achieve an exposure in serum of from at or about 6 hours to at or about 12 hours. In some embodiments, the compositions provided herein provide release characteristics that achieve an exposure in serum of from at or about 6 hours to at or about 8 hours. In some embodiments, the compositions provided herein provide release characteristics that achieve an exposure in serum of from at or about 8 hours to at or about 12 hours. In some embodiments, the compositions provided herein provide release characteristics that achieve an exposure in serum of from at or about 10 hours to at or about 12 hours. In some embodiments, the compositions provided herein provide release characteristics that achieve an exposure in serum of 5, 5.5, 6, 6.5, 7, 7.5, 8, 8.5, 9, 9.5, 10, 10.5, 11, 11.5 or 12 hours.

The compositions provided herein also result in an increased apparent half life of the drug. In one embodiment, the apparent half life is increased from at or about 1.3 hours in an immediate release formulation to at or about 10 or more hours. Due to the increase in apparent $t_{in}$ from 1.3 hours to 10 or more hours in humans with the compositions provided herein, a steady state plasma level can be produced within a small number of doses. In some embodiments, the apparent half life is increased 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75 or 15 hours.

The compositions provided herein reduce the adverse event profile by selectively producing a plasma level of the platelet number reducing agent that affects TPO-induced megakaryocytopoiesis while avoiding influencing the PDE systems, particularly PDE III and PDE V. The dosing regime of the compositions provided herein can be adjusted for once-daily or multiple doses per day. For example, in one embodiment, the composition provides a dosage of active ingredient to be administered twice daily to achieve a steady state and to produce the desired pharmacodynamic effect. In other embodiments, the composition provides a dosage of active ingredient to be administered once daily to achieve a steady state and to produce the desired pharmacodynamic effect.

In one embodiment, provided herein are sustained release orally administrable dosage unit forms that have an effective duration of activity of 5, 6, 7, 8, 9, 10, 11, 12, 13, 14, 15, 16, 17, 18, 19, 20, 21, 22, 23, 24 hours or more and are suitable for administration on a once daily or twice daily basis. In another embodiment, the compositions provided herein include an orally administrable sustained release dosage unit form containing anagrelide or its active metabolite, or a pharmaceutically acceptable derivative, analog or salt thereof, as an active ingredient, where the composition produces a reduced peak plasma level after administration and sustained exposure of at or about 8 hours or more, such as 8, 9, 10, 11, 12, 13, 14, 15, 16, 17, 18, 19, 20, 21, 22, 23, 24 hours.

The compositions provided herein provide an optimal pharmacokinetic profile of anagrelide or 3-OH anagrelide or analog or derivative thereof, with a reduction of the $C_{max}$, thereby reducing platelet number is a subject. The compositions release the anagrelide or 3-OH anagrelide or analog or derivative thereof in an amount and at a rate sufficient to inhibit TPO but not significantly inhibiting PDE, such as PDE III or PDE V, thereby minimizing or eliminating adverse events associated with PDE, such as those events mediated through an increase in cellular cAMP and/or cGMP levels. For example, in vivo studies with anagrelide in several models suggest that the PDE III inhibition effects are at greater plasma concentrations (effective oral doses of 0.1 mg-100 mg/kg) than required for TPO inhibition effects.

Exemplary dosages of platelet number reducing agent, e.g., anagrelide, 3-OH anagrelide or analogs or derivatives thereof, included in a single dosage unit form, such as a capsule, tablet, pill, troche, pastille, dragée, wafer, powder, elixir, suspension, syrup, caplet, lozenge or dissolvable film, can range from at or about 50 µg to at or about 2500 µg, such as 2500 µg, 2000 µg, 1900 µg, 1800 µg, 1700 µg, 1600 µg, 1500 µg, 1400 µg, 1300 µg, 1200 µg, 1100 µg, 1000 µg, 900 µg, 800 µg, 700 µg, 600 µg, 500 µg, 400 µg, 300 µg, 200 µg, 100 µg or 50 µg. In some embodiments, the dosage of platelet number reducing agent is selected from among at or about 10 ng to at or about 100 ng, at or about 10 ng to at or about 250 ng, at or about 10 ng to at or about 500 ng, at or about 10 ng to at or about 100 ng, at or about 10 ng to at or about 1000 ng, at or about 10 ng to at or about 250 ng, at or about 25 ng to at or about 250 ng, at or about 50 ng to at or about 500 ng, at or about 75 ng to at or about 750 ng, at or about 100 ng to at or about 1000 ng, at or about 250 ng to at or about 2500 ng, at or about 500 ng to at or about 5000 ng, at or about 750 ng to at or about 7500 ng and at or about 1000 ng to at or about 10000 ng. In some embodiments, the dosage of platelet number reducing agent is 10 ng, 20 ng, 30 ng, 40 ng, 50 ng, 60 ng, 70 ng, 80 ng, 90 ng, 100 ng, 125 ng, 150 ng, 175 ng, 200 ng, 225 ng, 250 ng, 275 ng, 300 ng, 325 ng, 350 ng, 375 ng, 400 ng, 425 ng, 450 ng, 475 ng, 500 ng, 525 ng, 550 ng, 575 ng, 600 ng, 625 ng, 650 ng, 675 ng, 700 ng, 725 ng, 750 ng, 775 ng, 800 ng, 825 ng, 850 ng, 875 ng, 900 ng, 925 ng, 950 ng, 975 ng or 1000 ng. In some embodiments, the dosage of platelet number reducing agent is 1 µg, 1.25 µg, 1.5 µg, 1.75 µg, 2 µg, 2.25 µg, 2.5 µg, 2.75 µg, 3 µg, 3.25 µg, 3.5 µg, 3.75 µg, 4 µg, 4.25 µg, 4.5 µg, 4.75 µg, 5 µg, 5.25 µg, 5.5 µg, 5.75 µg, 6 µg, 6.25 µg, 6.5 µg, 6.75 µg, 7 µg, 7.25 µg, 7.5 µg, 7.75 µg, 8 µg, 8.25 µg, 8.5 µg, 8.75 µg, 9 µg, 9.25 µg, 9.5 µg, 9.75 µg or 10 µg. In some embodiments, the dosage of platelet number reducing agent is 725 µg, 750 µg, 775 µg, 800 µg, 825 µg, 850 µg, 875 µg, 900 µg, 925 µg, 950 µg, 975 µg or 1000 µg.

It is understood that the precise dosage and duration of treatment is a function of the disease or condition being treated and can be determined empirically using known testing protocols or by extrapolation from in vivo or in vitro test data. It is to be noted that concentrations and dosage values can also vary with the severity of the disease or condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the compositions, methods and other subject matter provided herein. The dosage can be administered as a single daily dose, as 2-4 divided doses a day, every 2 days, every 3 days, every 4 days, every 5 days, every week, every 10 days, every 2 weeks, every month, or more.

In some embodiments, the compositions provided herein release anagrelide or 3-OH anagrelide or an analog or derivative thereof to produce a circulating concentration sufficient to elicit growth factor inhibition effects on megakaryocyte production of platelets, thereby reducing platelet number, but a concentration not sufficient to inhibit phosphodiesterase (PDE) activity to a clinically significant extent, thereby minimizing or eliminating adverse events.

By appropriate selection of dosage of anagrelide, 3-OH anagrelide or an analog or derivative thereof and its presentation as microparticles in a controlled release composition that includes a plurality of drug loaded solid cores that include a controlled release component, the apparent half life of anagrelide or 3-OH anagrelide or an analog or derivative thereof is increased 2, 3, 4, 5, 6, 7, 8, 9, 10, 11, 12, 13, 14, 15 or more fold. The compositions provided herein also delay $T_{max}$ by at or about 1 hour to at or about 6 hours. The compositions provided herein also provide an exposure in serum of from at or about 6 hours to at or about 18 hours, including 6, 7, 8, 9, 10, 11, 12, 13, 14, 15, 16, 17 and 18 hrs.

The compositions provided herein reduce the adverse event profile of anagrelide or 3-OH anagrelide or an analog or derivative thereof by selectively producing a plasma level of anagrelide or 3-OH anagrelide or an analog or derivative thereof that affects megakaryocytopoiesis but does not inhibit PDE systems, including PDE III and/or PDE V systems, to a clinically significant extent.

Also provided herein is an oral sustained release pharmaceutical unit dosage form containing a therapeutically effective amount of anagrelide, 3-hydroxy anagrelide, an analog or derivative thereof or a pharmaceutically acceptable salt thereof, where the unit dosage form is a tablet formed from, or a capsule containing, spheroid granules, pellets or beads that include an amount from at or about 10 ng to at or about 1000 µg of anagrelide, 3-hydroxy anagrelide, an analog or derivative thereof or a pharmaceutically acceptable salt thereof, the spheroid granules, pellets or beads including a core of a substantially water soluble, swellable or insoluble material; an optional preparatory coat; a substrate layer including the microparticles of anagrelide, 3-hydroxy anagrelide, an analog or derivative thereof or a pharmaceutically acceptable salt thereof; an optional seal coat layer including a substantially water-soluble polymer on the substrate layer; a release control component effective for controlled release of the active ingredient; and optionally a finishing coat and/or enteric coating, such that the unit dosage form provides a peak plasma level of anagrelide, 3-hydroxy anagrelide or an analog or derivative thereof at least 50% lower than produced by an immediate release formulation, and provides circulating anagrelide, 3-hydroxy anagrelide, or an analog or derivative thereof for at least 4 hours. In some embodiments, microparticles of anagrelide, 3-hydroxy anagrelide, an analog or derivative thereof or a pharmaceutically acceptable salt thereof are used in the composition.

1. Form of the Controlled Release Compositions

In one embodiment, the compositions provided herein include a plurality of water soluble, swellable or insoluble cores that optionally include a preparatory layer on or enveloping the core, a substrate layer containing a platelet number reducing agent, such as anagrelide, 3-OH anagrelide or pharmaceutically acceptable salts, derivatives or analogs thereof, an optional seal coat layer over or enveloping the substrate layer, a controlled release layer and an optional finishing coat and/or enteric coating on or enveloping the controlled release layer. The plurality of cores are discrete particles that together make up a multi-unit system. Because of their small size, the discrete particles present a larger surface area than a single unit formulation. The controlled release particles also are less dependent on gastric emptying and are better distributed, minimizing any local irritation. The compositions are modified to achieve a desired drug-release profile by adjusting the weight and composition of the substrate layer, the seal coat layer, if present, and the controlled release layer.

a. Cores

Exemplary water soluble, swellable or insoluble cores include, but are not limited to, a non-pareil seed, a bead, a granule, and a pellet. In one embodiment, the core includes a bead. In one embodiment, the core includes a non-pareil seed or a pellet. The core includes a soluble or insoluble material, such as sugar, starch, including modified starches, or a polyol, or combinations thereof. The core has a size in the range of at or about 100 to at or about 1500 microns. In some embodiments, the core has a size in the range of at or about 500 microns to at or about 1000 microns. In some embodiments, the core has a size in the range of at or about 1000 microns to at or about 1500 microns. In some embodiments, the core has a size in the range of from at or about 100 to at or about 500 microns. In some embodiments, the core has a size in the range of from at or about 200 to at or about 250 microns. In some embodiments, the core has a size in the range of from at or about 1000 to at or about 1400 microns (14-18 mesh sieve).

In some embodiments, the core has a size in the range of from at or about 600 to at or about 700 microns (25-30 mesh sieve). In some embodiments, the core has a size in the range of from at or about 1000 to at or about 1200 microns (16-18 mesh sieve). In some embodiments, the core has a size in the range of from at or about 500 to at or about 600 microns (30-35 mesh sieve). In some embodiments, the core has a size in the range of from at or about 850 to at or about 1200 microns (16-20 mesh sieve). In some embodiments, the core has a size in the range of from at or about 425 to at or about 500 microns (35-40 mesh sieve). In some embodiments, the core has a size in the range of from at or about 850 to at or about 1000 microns (18-20 mesh sieve). In some embodiments, the core has a size in the range of from at or about 250 to at or about 425 microns (40-60 mesh sieve). In some embodiments, the core has a size in the range of from at or about 700 to at or about 850 microns (20-25 mesh sieve).

The release profile of the compositions provided herein can be modulated by the selection of the size of the solid core. Smaller size cores can be selected to provide greater surface area for presentation of the platelet number reducing agent, facilitating presentation to biological fluids, such as gastric fluids, for dissolution of the platelet number reducing agent. Selection of larger solid cores can result in a lower surface area for presentation of the platelet number reducing agent to biological fluids, resulting in slower dissolution rates. In some embodiments, a combination of different size solid cores can be selected for preparation of the compositions provided herein to achieve a targeted dissolution rate.

b. Platelet Number Reducing Agent

Any compound that reduces the number of platelets in a subject can be used in the compositions provided herein. Exemplary platelet number reducing agents include anagrelide, 3-OH anagrelide and analogs and derivatives thereof; hydroxycarbamide (previously called hydroxyurea); busulphan; cyclophosphamide; ranimustine and pipobroman (e.g., see De Stefano et al., Haematologica 93(3): 372-380 (2008); Barbui & Finazzi, Blood Reviews 19(5): 243-252 (2005); Wagstaff & Keating, Drugs 66 (1): 111-131 (2006); Barbui & Finazzi, Blood 109(12): 5104-5111 (2007) and Najean et al., Blood, 90(9): 3370-3377 (1997)). In some embodiments, the anti-platelet agent is anagrelide, 3-OH anagrelide, derivatives or analogs of anagrelide, or pharmaceutically acceptable salts of anagrelide or 3-OH anagrelide, or combinations thereof. In some embodiments, the platelet number reducing agent is a combination of hydroxycarbamide and anagrelide, 3-OH anagrelide, derivatives or analogs of anagrelide, or pharmaceutically acceptable salts of anagrelide or 3-OH anagrelide, or combinations thereof.

c. Microparticles

Some platelet number reducing agents are sparingly soluble in water. For example, anagrelide is poorly soluble in water. As described herein, it and other such drugs can be made more bioavailable when provided in the form of small particles. In some embodiments, the platelet number reducing agent, such as anagrelide or 3-OH anagrelide or derivatives or analogs or pharmaceutically acceptable salts thereof, is in the form microparticles. Such microparticles provide a higher surface area and provide improved oral bioavailability. The microparticles can be prepared by reducing the size of the platelet number reducing agent by a micronization process. Any micronization process known in the art can be used (e.g., see U.S. Pat. Nos. 5,145,684, 5,302,401 and 5,470,583). Exemplary micronization processes include sonication, microfluidization, homogenization, wet grinding and milling, including rotary impact milling, rotor stator colloid milling, jet milling and air impact milling (e.g., see U.S. Pat. Nos. 5,091,187, 5,091,188, 5,972,366 and 6,994,283). Commercial manufacturers provide micronization services (e.g., see Micron Technologies, Inc., Exton, Pa.). In some embodiments, the platelet number reducing agent is micronized to yield microparticles having diameters ranging from at or about 0.05 to at or about 25 microns. In some embodiments, the platelet number reducing agent is micronized to yield microparticles having diameters less than 25 microns. In some embodiments, the platelet number reducing agent is micronized to yield microparticles having diameters less than or equal to 25, 24, 23, 22, 21, 20, 19, 18, 17, 16, 15, 14, 13, 12, 11, 10, 9, 8, 7, 6, 5, 4, 3, 2, 1, 0.75 or 0.5 microns.

The microparticles also can be crystals of the platelet number reducing agent grown to be within the size range contemplated. Crystalline microparticles of the platelet reducing agent can be produced by any method known in the art, and can be recovered by any suitable method, including filtration, centrifugation or spray drying (e.g., see U.S. Pat. Nos. 4,595, 418 and 6,682,761, WO0206538, Vehring et al., Pharm Res. 25(5): 999-1022 (2008) and Rasenack et at, Powder Technology, Vols. 143-144, pages 291-296 (2004)). The size of the drug microparticles can vary within large limits which are set by the desired rates of release of the drug and by physical stability and mechanical properties of the final product. In some embodiments, crystals of the platelet number reducing agent are grown and recovered to produce microparticles having diameters less than or equal to 25, 24, 23, 22, 21, 20, 19, 18, 17, 16, 15, 14, 13, 12, 11, 10, 9, 8, 7, 6, 5, 4, 3, 2, 1, 0.75 or 0.5 microns.

In some embodiments, the desired release profile is achieved by a combination of decreasing the particle size of the platelet number reducing agent by micronizing the agent to the requisite size and surface area or growing crystals of the platelet number reducing agent of the requisite size and surface area, resulting in microparticles, including microparticles less than or equal to 25 microns, such as less than or equal to 25, 24, 23, 22, 21, 20, 19, 18, 17, 16, 15, 14, 13, 12, 11, 10, 9, 8, 7, 6, 5, 4, 3, 2, 1, 0.75 or 0.5 microns, which increases the surface area of the active agent for improved or sustained bioavailability; application of the microparticles of the active agent on a solid core, and using a release control component effective for controlled release of the platelet number reducing agent.

The release profile of the platelet number reducing agent can be modulated by reducing the size of the platelet number reducing agent to form microparticles. For example, $C_{max}$ can be decreased by increasing the size of the microparticles of the platelet number reducing agent, making the agent less easily soluble. Conversely, the $C_{max}$ can be increased by decreasing the size of the microparticles, making the agent more easily soluble. Adjusting the size of the microparticles of the platelet number reducing agent also can be used to modulate $T_{max}$ and AUC or exposure. In some embodiments, a distribution of microparticle size or a combination of larger and smaller microparticles is used to provide a combination of slow and fast solubility of the platelet number reducing agent.

d. Coatings

The compositions provided herein include a solid core overlayered with one or more coatings. The coatings modulate the release profile in the compositions provided herein. The presence of one or more coatings, the composition of the coatings, such as the polymer selected, its molecular weight or solubility in biological fluids, the characteristics of any excipient included in the coating, and the thickness of the coating can be adjusted to achieve the desired release profile.

An exemplary composition provided herein includes a sugar bead as the solid core, which optionally is overlayed with a preparatory coat; a substrate layer that includes microparticles of a platelet number reducing agent on or enveloping the solid core; an optional seal coat layer on or enveloping the substrate layer; a controlled release layer; and optionally a finishing coat layer and/or an enteric coating layer on or enveloping the controlled release layer. The desired release profile of the composition can be achieved by the appropriate selection of the size or distribution of sizes of the solid cores, the size and/or distribution of sizes of the microparticles of the platelet number reducing agent in the substrate layer, the thickness and composition of the seal coat layer, if present, the thickness and composition of the controlled release layer, and the thickness and composition of the finishing coat layer and/or enteric coating layer, if present. Adjusting these components of the composition allows pharmacokinetic properties of the composition, such as the $C_{max}$, $T_{max}$ and AUC, to be modulated.

i. Optional Preparatory Coat

In some embodiments, an optional a preparatory coat is applied on the surface of the core between the core and the substrate layer containing the active ingredient. The preparatory coat can be prepared so that when applied to the cores, the dried preparatory coat adds from at or about 0.1% to at or about 5% by weight to the weight of the composition. Exemplary weights of the preparatory coat include 0.5%, 0.55%, 0.6%, 0.65%, 0.7%, 0.75%, 0.8%, 0.85%, 0.9%, 0.95%, 1%, 1.05%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.05%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3%, 3.05%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4%, 4.05%, 4.1%, 4.15%, 4.2%, 4.25%, 4.3%, 4.35%, 4.4%, 4.45%, 4.5%, 4.55%, 4.6%, 4.65%, 4.7%, 4.75%, 4.8%, 4.85%, 4.9%, 4.95% and 5% (weight % basis). Exemplary polymers that can be included in the optional preparatory coat include cellulose derivatives, including hydroxypropyl methyl cellulose (HPMC) and carboxymethylcellulose (CMC), xanthan gum, starch, including amylose or amylopectin, modified starch, polyvinylpyrrolidone (PVP) and combinations thereof. The preparatory coat smoothes the surface of the core such that the surface area is more consistent from lot to lot, thereby improving the surface area and overall coating quality when the substrate layer containing the active ingredient is applied.

ii. Substrate Layer

In the compositions provided herein, the platelet-reducing agent can be coated on the surface of a solid support core or on the optional preparatory layer on the core via a substrate layer that includes at least one excipient, such as, but not limited to, a binder, a surfactant and a filler. Exemplary binders include, but are not limited to, water-soluble, hydrophilic polymers, such as polyvinyl pyrrolidone, a cellulosic polymer, such as hydroxypropyl methylcellulose, hydroxypropyl cellulose, carboxymethyl cellulose, hydroxymethyl cellulose, gelatin, gum arabic, gellan gum, xanthan gum, carrageenan, polyethylene oxide, polymethacrylates, dextrin, and starch or starch derivatives or combinations thereof. In some embodiments, the binder includes a hydroxypropyl methylcellulose. In one embodiment, the binder includes a low molecular weight hydroxypropyl methyl cellulose. In some embodiments, the binder includes povidone.

If a binder is included in the substrate layer, the binder can be present in an amount of at or about 0.1-5% of the weight of the composition (weight %). For example, the binder in the substrate layer, when dry on a finished composition, can represent 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.05%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3%, 3.05%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4%, 4.05%, 4.1%, 4.15%, 4.2%, 4.25%, 4.3%, 4.35%, 4.4%, 4.45%, 4.5%, 4.55%, 4.6%, 4.65%, 4.7%, 4.75%, 4.8%, 4.85%, 4.9%, 4.95% or 5% of the weight of the final composition.

In some embodiments, the substrate layer includes a filler. Examples of suitable fillers include, but are not limited to lactose, glucose, fructose, sucrose, dicalcium phosphate, sugar alcohols, such as sorbitol, mannitol, lactitol, xylitol, isomalt, erythritol, and hydrogenated starch hydrolysates (a blend of several sugar alcohols), corn starch, potato starch, and cellulose acetate, or a mixture thereof. In some embodiments, the substrate layer includes a surfactant. The surfactant can be anionic, such as sodium lauryl sulfate (USP) and its derivatives, cationic, such as the quaternary ammonium halides (such as cetyl pyridinium chloride) or non-ionic, such as linear fatty alcohol ethoxylates or the polyoxyethylene condensation products (such as Spans and Tweens or polyoxyethylene polypropylene glycol, such as Pluronic F68, available from BASF Corp., Mt. Olive, N.J.), polyglycerol esters of fatty acids, polyoxethylene sorbitan monolaurate, polyoxethylene sorbitan mono- or tri-stearate, polyoxyethylene sorbitan monoleate, propylene glycol mono and diesters of fats and fatty acids, sorbitan monostearate, poloxamer and its derivatives, medium chain triglyceride, caprylocaproyl macrogolglycerides, diethyleneglycol monoethyl ether, PEG-6 olive oil, PEG-6 peanut oil, PEG-6 hydrogenated palm kernel oil, propylene glycol dicaprylate/dicaprate, polysorbate, sorbitan esters, polyethoxylated castor oil, PEG-60 hydrogenated castor oil, PEG-40 hydrogenated castor oil, sodium lauryl glutamate, disodium cocoamphodiacetate, Polyoxyl 23 lauryl ester and combinations thereof.

iii. Seal Coat Layer

The compositions provided herein include a seal coat layer overlaying the substrate layer that includes one or more platelet-reducing agents. The seal coat layer can be provided in order to prevent physical or chemical interactions, such as a hydrophobic interaction, between the substrate layer including the platelet number reducing agent and the controlled release layer. The seal coat layer also can be used to modulate the release profile of the composition. For example, a seal coat layer can be included to decrease dissolution rates upon exposure to biological fluids, thereby allowing modulation of $C_{max}$, $T_{max}$ and AUC or exposure. For example, the dissolution rate can be slowed by increasing the thickness of the seal coat layer, or by selecting a polymer that hydrates slowly in biological fluids, or by selecting a polymer having a high molecular weight or that exhibits a high viscosity upon hydration, or any combination thereof. The hydration characteristics of the polymer used in the optional seal coat layer is governed by the structure, size and properties of its macromolecules. The solubility of the seal coat layer also can be modulated by optionally including at least one excipient, such as a binder, a surfactant, or a filler.

Examples of suitable polymers that can be included in the seal coat layer include, but are not limited, to water-soluble, hydrophilic polymers, such as povidone (PVP: polyvinyl pyrrolidone), low molecular weight hydroxypropyl cellulose (HPC), low molecular weight hydroxypropyl methylcellulose (HPMC), low molecular weight carboxy methyl cellulose (CMC), low molecular weight ethyl cellulose, gelatin, polyethylene oxide, gum arabic, dextrin, magnesium aluminum silicate, starch, and polymethacrylates and combinations thereof. In one embodiment, the seal coat layer includes HPMC. In some embodiments, such as where the controlled release layer includes a fatty acid or fatty acid ester, the substrate layer is overcoated with a seal coat layer prior to coating with the controlled release layer. In particular, when the controlled release layer includes a fatty acid selected from among oleic, steric, linoleic, myristic, palmitic, and lauric, and the platelet number reducing agent is anagrelide, 3-OH anagrelide or derivatives or analogs thereof, the substrate layer is overcoated with a seal coat layer prior to coating with the controlled release layer. The overlayering of the substrate layer with the seal coat layer prior to application of the controlled release layer can eliminate hydrophobic interactions between the anagrelide or 3-OH anagrelide and a fatty acid in the controlled release layer. Such hydrophobic interactions between the active ingredient and a fatty acid can result in a fatty acid/active ingredient complex that negatively impacts on the release profile of the active ingredient from the resulting controlled release composition.

The seal coat layer can be present in an amount of at or about 1% to at or about 10% of the weight of the composition (weight %). For example, the seal coat layer, when dry on a finished composition, can represent 1%, 1.05%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.05%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3%, 3.05%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4%, 4.05%, 4.1%, 4.15%, 4.2%, 4.25%, 4.3%, 4.35%, 4.4%, 4.5%, 4.5%, 4.6%, 4.6%, 4.7%, 4.75%, 4.8%, 4.85%, 4.9%, 4.95%, 5%, 5.05%, 5.1%, 5.15%, 5.2%, 5.25%, 5.3%, 5.35%, 5.4%, 5.45%, 5.5%, 5.55%, 5.6%, 5.65%, 5.7%, 5.75%, 5.8%, 5.85%, 5.9%, 5.95%, 6%, 6.05%, 6.1%, 6.15%, 6.2%, 6.25%, 6.3%, 6.35%, 6.4%, 6.45%, 6.5%, 6.55%, 6.6%, 6.65%, 6.7%, 6.75%, 6.8%, 6.85%, 6.9%, 6.95%, 7%, 7.05%, 7.1%, 7.15%, 7.2%, 7.25%, 7.7%, 7.75%, 7.4%, 7.45%, 7.5%, 7.55%, 7.6%, 7.65%, 7.7%, 7.75%, 7.8%, 7.85%, 7.9%, 7.95%, 8%, 8.05%, 8.1%, 8.15%, 8.2%, 8.25%, 8.3%, 8.35%, 8.4%, 8.45%, 8.5%, 8.55%, 8.6%, 8.65%, 8.7%, 8.75%, 8.8%, 8.85%, 8.9%, 8.95%, 9%, 8.1%, 9.15%, 9.2%, 9.25%, 9.3%, 9.35%, 9.4%, 9.45%, 9.5%, 9.55%, 9.6%, 9.65%, 9.7%, 9.75%, 9.8%, 9.85%, 9.9%, 9.95% or 10% of the weight of the spheroid multiparticulates (coated solid cores).

iv. Release Control Component

The release profile of the compositions provided herein also can be modulated by including a release control component. In some embodiments, the spheroid multiparticulates of the compositions provided herein include a release control component effective for controlled release of the platelet number reducing agent. Any film-forming polymer known in the art that can modulate the release of an active agent from a pharmaceutical composition can be used in the composition (e.g., see U.S. Pat. Nos. 3,065,143; 3,427,378; 3,444,290; 3,458,622; 3,555,151; 3,574,820; 3,976,764; 4,140,755; 4,173,626; 4,248,857; 4,252,786; 4,259,314; 4,309,404; 4,309,405). The characteristics of the polymer used in the film-coating are governed by the structure, size and properties of its macromolecules. A release control coating layer can be included to decrease dissolution rates upon exposure to biological fluids, thereby allowing modulation of $C_{max}$, $T_{max}$ and AUC or exposure.

Common film-forming polymers used in pharmaceuticals as non-enteric materials that can be used in the compositions provided herein include ethyl cellulose, hydroxypropyl cellulose, hydroxypropyl methyl cellulose or a mixture of two or more of such cellulose derivatives, polyvinyl acetate, povidone, cross-linked starch, cross-linked chitosan, cross-linked gelatin, cross-linked hyaluronic acid, cross-linked polyvinyl alcohol, cross-linked sodium carboxymethyl cellulose, cross-linked polyvinyl pyrrolidone, carboxypolymethylene, zein or combinations thereof.

An exemplary film-forming polymer is ethyl cellulose, used by itself or in combination with other film-forming polymers. Ethyl cellulose is a cellulose ether that is formed by the reaction of ethyl chloride with alkaline cellulose, and is generally insoluble in water and gastrointestinal fluid. It is commonly used in combination with hydroxypropyl methylcellulose and other film-formers to toughen or influence the dissolution rate of the film. Due to the solubility characteristics of ethyl cellulose, this polymer can be applied as an aqueous dispersion or an organic solvent dispersion. Aqueous ethyl cellulose dispersions can include dispersion agents, surfactants, such as sodium lauryl sulfate, anti-foam agents, plasticizers and solubility aids. Exemplary plasticizers include acetylated monoglyceride; acetyl glycols; acetyl tributyl citrate; butyl phthalyl butyl glycolate; dibutyl sebacate; dibutyl tartrate; diethyl phthalate; dimethyl phthalate; ethyl phthalyl ethyl glycolate; glycerin; propylene glycol; triacetin; triacetin citrate; tributyl citrate; and tripropionin. For example, ethyl cellulose can be blended with dibutyl sebacate, and ammonium oleate to prepare a dispersion of stabilized, plasticized ethyl cellulose particles (e.g., see U.S. Pat. Nos. 4,123,403 and 4,502,888). Organic solvent dispersions of ethyl cellulose can include any suitable organic solvent. Exemplary organic solvents include alcohols, such as ethanol, propanal, and butanol, acetone, ethyl acetate and ethyl lactate. Organic solvent dispersions of ethyl cellulose also can include dispersing aids, surfactants and plasticizers. The organic solvent coating systems can include water, and thus are not strictly non-aqueous. These systems are predominantly organic in nature due to the greater proportion of organic solvent in the mixed dispersions. In some embodiments, the controlled release layer includes ethyl cellulose.

Another exemplary film-forming polymer is polyvinyl acetate, used by itself or in combination with other film-forming polymers, such as povidone. Polyvinyl acetate can be formulated into aqueous dispersions, and provides excellent film-forming properties and pH-independent adjustment of release rate. Aqueous polyvinyl acetate dispersions can include dispersion agents, surfactants, such as sodium lauryl sulfate, anti-foam agents, plasticizers and solubility aids. Exemplary plasticizers include acetylated monoglyceride; acetyl glycols; acetyl tributyl citrate; butyl phthalyl butyl glycolate; dibutyl sebacate; dibutyl tartrate; diethyl phthalate; dimethyl phthalate; ethyl phthalyl ethyl glycolate; glycerin; propylene glycol; triacetin; triacetin citrate; tributyl citrate, and tripropionin. Commercially available film-coating formulations containing polyvinyl acetate can be used. Exemplary commercially available formulations that can be included in the release control component include an aqueous dispersion of polyvinyl acetate stabilized with povidone and sodium lauryl sulfate, such as the commercially available formulation marketed under the trademark KOLLICOAT® (from BASF, Florham Park, N.J.).

In some embodiments, the controlled release layer includes a hydrophilic pore former. The pore former included in the controlled release layer can be any art recognized pore forming chemical species that is compatible for use with the control component. For example, when the control release component includes ethyl cellulose, the hydrophilic pore former is selected to be compatible with ethyl cellulose dispersions. Pore formers can be water-soluble hydrophilic polymers, proteins, sugars or sugar alcohols. Exemplary pore formers include cellulose ethers, including hydroxypropyl methylcellulose, sodium alginate, polyvinylpyrrolidone, cross-linked polyvinylpyrrolidone, polyethylene oxide, polyethylene glycol, pullulan, dextran, sucrose, glucose, fructose, mannitol, lactose, mannose, galactose, and sorbitol. In one embodiment, the pore former is hydroxypropyl methylcellulose.

The amount of pore former included in the controlled release layer depends to some degree on the chemistry of the pore former selected, but for purposes of illustration and not limitation, when hydroxypropyl methylcellulose is selected as the pore former, it can be used in a range from at or about 0.1 to 10%, including from at or about 0.25% to at or about 5.0%. In some embodiments, the pore former can represent a large portion of the applied solution (e.g.; 25% of the applied solution). In terms of weight gain of the compositions after a solution containing the pore former is applied, the pore former may constitute 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.05%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3%, 3.05%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4%, 4.05%, 4.1%, 4.15%, 4.2%, 4.25%, 4.3%, 4.35%, 4.4%, 4.45%, 4.5%, 4.55%, 4.6%, 4.65%, 4.7%, 4.75%, 4.8%, 4.85%, 4.9%, 4.95% or 5% of the weight of the spheroid multiparticulates (i.e., weight gain of the coated solid cores based on the applied pore former). The relative amounts of pore former and controlled release polymer, such as ethyl cellulose, in the controlled release layer can be varied to adjust the rate of release, with larger proportions of pore former resulting in faster release rates compared to smaller proportions of pore former. In some embodiments, the controlled release layer contains at or about 60% to at or about 95% by weight of ethyl cellulose and at or about 40% to at or about 5% by weight of hydroxypropyl methylcellulose. In some embodiments, the controlled release layer contains at or about 90% ethyl cellulose and at or about 10% hydroxypropyl methyl cellulose. In some embodiments, the controlled release layer contains at or about 85% ethyl cellulose and at or about 15% hydroxypropyl methylcellulose. The ratio of ethyl cellulose to the pore former in the controlled release layer can range from at or about 1:1 to at or about 12:1. In some embodiments, the ratio is 10:1 or 9:1 ethyl cellulose to the pore former. In some embodiments, the ratio is from at or about 2:1 to at or about 4:1 ethyl cellulose to the pore former.

When ethyl cellulose is used as a controlled release film forming polymer, an effective amount of a suitable plasticizing agent can be included. Addition of a plasticizer modulates the physical properties of the film. Examples of suitable plasticizers include, but are not limited to, long chain fatty alcohols such as, for example, cetyl alcohol, myristyl alcohol, and stearyl alcohol, fatty acids, such as oleic, steric, linoleic, myristic, palmitic, and lauric, fatty acid esters, such as sorbityl derivatives and glycerides, acetylated mono-glycerides, glycerides such as glyceryl esters of fatty acids or hydrogenated aliphatic acids such as, for example, glyceryl monostearate, glyceryl distearate, castor oil and derivatives thereof, glyceryl esters of hydrogenated castor oil, dibutyl sebacate, diethyl phthalate and other phthalate esters, glycerin, propylene glycol, tributyl citrate, triethyl citrate and triacetin.

The controlled release layer is prepared by deposition of one or more film-forming polymers resulting in coats or layers that can represent from at or about 0.1-25% by weight of the final coated product, such as at or about 0.15 to at or about 20%, or at or about 0.2 to at or about 15%, or at or about 0.25 to at or about 10%. In some embodiments, the controlled release layer represents at or about 0.25 to at or about 5% of the weight of the composition. In some embodiments, the controlled release layer represents about from 2.5% to at or about 7.5% of the weight of the composition. In some embodiments, the controlled release layer represents about from 4% to at or about 12% of the weight of the composition. The controlled release layer can be applied at a lesser or greater weight gain depending upon the physical properties of the therapeutically active agent and the desired release rate, whether a plasticizer is incorporated in the composition and the manner of incorporation of such a plasticizer, if used, for example. In some embodiments, the controlled release layer is 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.05%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3%, 3.05%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4%, 4.05%, 4.1%, 4.15%, 4.2%, 4.25%, 4.3%, 4.35%, 4.4%, 4.45%, 4.5%, 4.55%, 4.6%, 4.65%, 4.7%, 4.75%, 4.8%, 4.85%, 4.9%, 4.95%, 5%, 5.05%, 5.1%, 5.15%, 5.2%, 5.25%, 5.3%, 5.35%, 5.4%, 5.45%, 5.5%, 5.55%, 5.6%, 5.65%, 5.7%, 5.75%, 5.8%, 5.85%, 5.9%, 5.95%, 6%, 6.05%, 6.1%, 6.15%, 6.2%, 6.25%, 6.3%, 6.35%, 6.4%, 6.45%, 6.5%, 6.55%, 6.6%, 6.65%, 6.7%, 6.75%, 6.8%, 6.85%, 6.9%, 6.95%, 7%, 7.05%, 7.1%, 7.15%, 7.2%, 7.25%, 7.3%, 7.35%, 7.4%, 7.45%, 7.5%, 7.55%, 7.6%, 7.65%, 7.7%, 7.75%, 7.8%, 7.85%, 7.9%, 7.95%, 8%, 8.05%, 8.1%, 8.15%, 8.2%, 8.25%, 8.3%, 8.35%, 8.4%, 8.45%, 8.5%, 8.55%, 8.6%, 8.65%, 8.7%, 8.75%, 8.8%, 8.85%, 8.9%, 8.95%, 9%, 9.05%, 9.1%, 9.15%, 9.2%, 9.25%, 9.3%, 9.35%, 9.4%, 9.45%, 9.5%, 9.55%, 9.6%, 9.65%, 9.7%, 9.75%, 9.8%, 9.85%, 9.9%, 9.95% or 10% of the weight of the spheroid multiparticulates (coated solid cores).

Dispersions of ethyl cellulose are commercially available. For example, a commercially available aqueous dispersion of ethyl cellulose is marketed under the trademark AQUACOAT ECD® (FMC Corp., Philadelphia, Pa., U.S.A.). AQUACOAT ECD® is a water-based system that includes from 24.5-29.5% by weight ethylcellulose, 0.9%-1.7% sodium lauryl sulfate and 1.7-3.3% cetyl alcohol. Another commercially available aqueous dispersion of ethyl cellulose is marketed under the trademark SURELEASE® (Colorcon, Inc., West Point, Pa., U.S.A.). This product is prepared by incorporating a plasticizer, such as ammonium oleate, into the dispersion of ethylcellulose during the manufacturing process (e.g., see U.S. Pat. Nos. 4,123,403 and 4,502,888).

The controlled release layer is applied directly to the substrate layer or to an optional seal coat layer that is applied to the substrate layer. The release profile of the compositions provided herein can be modulated by the thickness of the release control component as well as the characteristics of the polymer or polymers selected as the release control component.

v. Optional Finishing Coat

In some embodiments, a finishing coat is applied over the controlled release layer to provide uniformity or to provide an erodible layer for manipulating release rates of the active ingredient from the spheroid multiparticulates, or as a bioadhesive for targeted release of the anti-platelet agent or for providing a tack-free bead surface. In some embodiments, an optional finishing coat is used to aid in the handling and metering of the spheroid multiparticulates, such as for capsule filling or tableting. The finishing coat can include a hydrophilic polymer, such as a hydroxyalkyl cellulose, including hydroxypropyl methyl cellulose (HPMC), hydroxypropyl cellulose (HPC), carboxymethyl cellulose (CMC), other cellulose ethers, polyvinyl alcohol, polyethylene glycol, starch, xanthan gum, gellan gum, modified starch, acrylic polymers or polyvinylpyrrolidone (PVP) or combinations thereof. The finishing coat also can include plasticizers and additional solids, such as talc or titanium oxide. Generally, the finishing coat solution/suspension includes from at or about 0.25 to at or about 15% of total solid contents, such as at or about 0.5 to at or about 10% polymer-plasticizer solids.

In some embodiments, the finishing coat layer is at or about 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.05%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3%, 3.05%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4%, 4.05%, 4.1%, 4.15%, 4.2%, 4.25%, 4.3%, 4.35%, 4.4%, 4.45%, 4.5%, 4.55%, 4.6%, 4.65%, 4.7%, 4.75%, 4.8%, 4.85%, 4.9%, 4.95%, 5%, 5.05%, 5.1%, 5.15%, 5.2%, 5.25%, 5.3%, 5.35%, 5.4%, 5.45%, 5.5%, 5.55%, 5.6%, 5.65%, 5.7%, 5.75%, 5.8%, 5.85%, 5.9%, 5.95%, 6%, 6.05%, 6.1%, 6.15%, 6.2%, 6.25%, 6.3%, 6.35%, 6.4%, 6.45%, 6.5%, 6.55%, 6.6%, 6.65%, 6.7%, 6.75%, 6.8%, 6.85%, 6.9%, 6.95%, 7%, 7.05%, 7.1%, 7.15%, 7.2%, 7.25%, 7.3%, 7.35%, 7.4%, 7.45%, 7.5%, 7.55%, 7.6%, 7.65%, 7.7%, 7.75%, 7.8%, 7.85%, 7.9%, 7.95%, 8%, 8.05%, 8.1%, 8.15%, 8.2%, 8.25%, 8.3%, 8.35%, 8.4%, 8.45%, 8.5%, 8.55%, 8.6%, 8.65%, 8.7%, 8.75%, 8.8%, 8.85%, 8.9%, 8.95%, 9%, 9.05%, 9.1%, 9.15%, 9.2%, 9.25%, 9.3%, 9.35%, 9.4%, 9.45%, 9.5%, 9.55%, 9.6%, 9.65%, 9.7%, 9.75%, 9.8%, 9.85%, 9.9%, 9.95% and 10% of the total weight of the spheroid multiparticulates (coated cores). It is contemplated that for certain applications, small amounts of non-aqueous solvents or carriers can be included in the finishing coat.

Commercially available film-coating formulations can be used. Exemplary commercially available formulations that can be included in the optional finishing coat include low viscosity hydroxypropyl methylcellulose as the polymer, such as the commercially available formulation marketed under the trademark OPADRY® (from Colorcon Corporation, West Point, Pa.). Any suitable plasticizer can be included. Anti-foam agents also can be included. Exemplary anti-foam agents include silicones or polydimethylsiloxane, such as Dow Corning® MEDICAL ANTIFOAM A COMPOUND (from Dow Corning, Midland, Mich.), which is simethicone USP.

The optional finishing coat can be overlayered on a controlled release layer that was deposited using an aqueous coating system or an organic solvent coating system. In some embodiments, the controlled release layer deposited using an organic solvent coating system is sufficiently smooth that an optional finishing coat is unnecessary.

2. Pharmaceutical Delivery Forms

The compositions provided herein can be presented in a form suitable for oral or other routes of administration.

a. Compositions for Oral Administration

In certain embodiments, oral pharmaceutical dosage forms that are either solid, gel or liquid are provided. The coated multi-particulates, such as spherical or spheroid granules, pellets or beads, prepared as described herein can be presented as a dosage unit form, such as a capsule, tablet, pill, troche, pastille, dragée, wafer, powder, elixir, suspension, syrup, caplet, lozenge or dissolvable film or in any other suitable dosage form. In some embodiments, coated multiparticulates that have different release rates are prepared and combined. For example, coated multi-particulates that release the platelet number reducing agent over a time frame of from 6-8 hours can be blended with coated multi-particulates that release the platelet number reducing agent over a time frame of from 2-4 hours or that release the platelet number reducing agent over a time frame of from 10-12 hours.

In some embodiments, the controlled release multi-particles can be combined with 0-50% immediate release particulates including a platelet number reducing agent. In some embodiments, a blend of 50% controlled release particulates as described herein and 50% immediate release particulates including an immediate release formulation of the platelet number reducing agent is presented in an oral pharmaceutical dosage forms, such as a solid, gel or liquid, particularly in the form of a capsule or a tablet.

The controlled release compositions including one or more platelet number reducing agents provided herein can be included in a solid dosage form for administration to a subject. In one embodiment, the controlled release beads are placed in a capsule in an amount sufficient to provide an effective controlled release dose when ingested and contacted by gastric fluid. Capsules can be hard or soft gelatin capsules or can be made of non-gelatin materials (e.g., see U.S. Pat. Nos. 5,342,626 and 6,214,376). In certain embodiments, pharmaceutical compositions for oral administration provided herein include push fit capsules made of gelatin or other suitable polymer(s). In certain embodiments, pharmaceutical compositions for oral administration provided herein include soft, sealed capsules made of gelatin and a plasticizer, such as glycerol or sorbitol, into which the controlled release compositions including platelet number reducing agent provided herein are loaded.

The controlled release compositions provided herein also can be compressed into tablets using any method known in the art. For example, the compositions provided herein can be mixed with a pharmaceutically acceptable matrix and compressed into a tablet. Compressed tablets, for example, can be prepared by mixing a composition provided herein with excipients intended to add binding qualities and/or disintegration qualities. The mixture is either directly compressed or granulated then compressed using methods and machinery known to those in the industry. The resultant compressed tablet dosage units then can be packaged according to market need, e.g., unit dose, rolls, bulk bottles or blister packs. For example, melted stearyl alcohol can be mixed with a composition provided herein and then blended with talc and magnesium stearate to provide a blend. The resulting blend then can be compressed into a tablet using a tablet press. Conventional tablet machinery and procedures, including direct compression, can be used. Those individuals involved in pharmaceutical solid dosage form production are versed in the processes and the machinery used in the production of solid dosage forms in the pharmaceutical industry. Types of oral tablets include compressed tablets, lozenges and coated tablets that include an enteric-, sugar- or film-coating.

In certain embodiments, the controlled release compositions provided herein are used for oral, sublingual or buccal administration. Certain of such pharmaceutical compositions are tablets or lozenges formulated in a conventional manner. The oral formulation also can be an edible film or readily dissolvable film containing the controlled release compositions described herein. Readily dissolvable edible film and their method of manufacture are well known in the art (e.g., see U.S. Pat. Nos. 6,596,298; 6,656,493; 6,923,981; and 7,241,411).

In certain embodiments, the solid dosage forms, e.g., tablets, pills, capsules and troches, which include a controlled release composition as described herein, contain one or a combination of a binding agent; a diluent; a disintegrating agent; a lubricant; a glidant; a sweetening agent and a wetting agent.

Examples of binding agents for use in the compositions provided herein include microcrystalline cellulose, gum tragacanth, gum arabic, gelatin and starch paste. Lubricants include talc, starch, magnesium or calcium stearate and stearic acid. Diluents include, for example, lactose, sucrose, starch, kaolin, salt, mannitol and dicalcium phosphate. Glidants include, but are not limited to, colloidal silicon dioxide. Disintegrating agents include croscarmellose sodium, sodium starch glycolate, alginic acid, sodium alginate, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, sucralose, neotame, acesulfame potassium and aspartame. Wetting agents include propylene glycol monostearate, sorbitan monooleate, diethylene glycol monolaurate and polyoxyethylene laural ether.

In some embodiments, an optional enteric coating is included to protect the controlled release dosage form from the acidic environment of the stomach. For example, the composition can be formulated to include an outer enteric coating that maintains its integrity in the stomach and releases the active agent in the intestine. Enteric coatings are well-known in the art. For example, enteric coatings include, but are not limited to, acrylic resins, fats, fatty acids, waxes, wax mixtures, shellac, ammoniated shellac, phenylsalicylate, methacrylic acid copolymers (such as those marketed under the trademark EUDRAGIT® polymers), maleic acid co-polymers, such as styrene maleic acid co-polymers, poly (methyl vinyl ether)maleic acid) (such as those marketed under the trademark GANTREZ® monoester resins), and the phthalate or succinate salts of the following polymers: cellulose acetate, hydroxyethyl ethyl cellulose, hydroxypropyl methyl cellulose and polyvinyl acetate, or combinations thereof.

The controlled release compositions provided herein also can be administered as a component of compositions, e.g., a suspension. Suspensions use pharmaceutically acceptable suspending agents, such as xanthan gum, carrageen, sodium carboxymethyl cellulose, pectin, guar or clay (e.g., those marketed under the trademark VEEGUM®), and preservatives.

b. Compositions for Other Routes of Administration

Other routes of administration, such as rectal administration, also are contemplated herein. In certain embodiments, the pharmaceutical composition is prepared for topical administration such as rectal administration. The pharmaceutical dosage forms for rectal administration include, but are not limited to rectal suppositories, capsules and tablets for systemic effect. In certain embodiments, the controlled release compositions provided herein are prepared for rectal administration, such as a suppository. Rectal suppositories are solid dosages for insertion into the rectum, formulated to melt or soften at body temperature. Pharmaceutically acceptable substances used in rectal suppositories include a base vehicle, such as cocoa butter, polyoxyethylene glycol (e.g., such as available under the trademark CARBOWAX™), methoxypolyethylene glycol, a glycerin-gelatin combination, and appropriate mixtures of mono-, di- and tri-glycerides of fatty acids. Combinations of the various base vehicles can be used. The suppositories optionally can include agents to raise the melting point. Agents to raise the melting point of suppositories include, e.g., spermaceti and wax. Rectal suppositories can be prepared either by the compressed method or by molding. Tablets and capsules for rectal administration are manufactured using the same pharmaceutically acceptable substance and by the same methods as for formulations for oral administration.

F. Methods of Making the Coated Particulates

The coated particulates of the controlled release compositions provided herein can be made using any appropriate method known in the art. For example, the various coating layers can be applied to a solid support, such as a water soluble, swellable or insoluble core, by conventional coating techniques such as, for instance, pan coating, fluidized bed coating, fluidized bed bottom sprayed coating, air suspension coating, compression coating, spray drying, spray congealing, solvent evaporation, coacervation, and interfacial complexation. The polymer solution or suspension can be in a conventional coating pan, or, alternatively, using an automated system such as a Fluidized Bed Processor (e.g., those available from Glatt Air Techniques Inc., Ramsey, N.J.) or a top spray or bottom spray fluid bed coaters (e.g., Precision Coater™, available from Niro Inc., Columbia, Md.). A fluidized bed is a bed of solid particles that are suspended in a stream of air or gas passing upward through the particles, in which the coating material is aerosolized. As the air travels through the particle bed, the particles are mixed in the stream of gas or air with the coating material, and so are coated and also are dried.

In one embodiment, a plurality of water soluble, swellable or insoluble core particulates, such as non-pareil beads, are coated with a substrate layer that includes a platelet number reducing agent, such as anagrelide or 3-OH anagrelide, and overlayered with a controlled release layer. In this embodiment, beads coated with a therapeutically active amount of a platelet number reducing agent are prepared, e.g., by dispersing the platelet number reducing agent in water and then applying the dispersed active agent onto a substrate, for example, non-pareil 18/20 beads. The dispersion can be applied by any technique known in the art, such as spraying, fluid bed possessing or pan coating. Optionally, additional ingredients also are added to the substrate layer solution prior to application to the solid support (e.g., non-pareil beads) in order to assist binding of the platelet number reducing agent, such as anagrelide or 3-OH anagrelide or derivatives or analogs thereof, to the solid support. For example, hydroxypropyl-methylcellulose (HPMC), carboxymethyl cellulose (CMC), hydroxypropyl cellulose (HPC) or blends thereof can be added to the substrate layer solution and the substrate layer solution mixed (e.g., for about 60 to 120 minutes) prior to application of the substrate layer solution onto the solid support. The resultant coated solid support cores including a substrate layer (e.g., non-pareil beads including a substrate layer that includes anagrelide or 3-OH anagrelide), can then optionally be overcoated with a seal coat layer, such as to separate the platelet number reducing agent from the controlled release layer. An example of a suitable seal coat layer is one that includes a cellulose derivative polymer, such as hydroxypropyl methylcellulose. Any film forming polymer known in the art can be used.

The solid support cores including the substrate layer and optionally a seal coat layer then are overcoated with a solution including one or more than one controlled release polymer. In one embodiment, the solution including the controlled release polymer is an aqueous dispersion of ethyl cellulose, such as pre-formulated aqueous dispersion of ethyl cellulose, such as those marketed under the trademark AQUACOAT® or the trademark SURELEASE®. The controlled release polymer can be applied onto the substrate layer that includes the active ingredient or the seal coat layer if present by spraying using any suitable spray equipment known in the art. A sufficient amount of the controlled release polymer to obtain a predetermined controlled release of the active agent when the coated substrate is exposed to aqueous solutions, e.g., gastric fluid, is applied. After applying the controlled release polymer layer, a further overcoat of a finishing coat, such as hydroxypropyl methylcellulose, is optionally applied to the beads. This finishing coat can be provided, if at all, in order to reduce agglomeration of the beads and to aid processing.

A colorant can be added to any of the substrate layer, optional seal coat layer, controlled release layer or optional finishing coating. For example, a colorant can be added to the aqueous dispersion of ethyl cellulose or to the solution including of the platelet number reducing agent. Coloring agents include, for example, any of the approved certified water soluble FD and C dyes, mixtures thereof; and water insoluble FD and C dyes suspended on alumina hydrate, milled aluminum lakes and opacifiers such as titanium dioxide.

For example, an anagrelide substrate layer solution (anagrelide coating solution) can be spray coated onto solid sores. The coating solution includes an amount of solids appropriate for the manufacturing equipment and conditions used. The anagrelide coated beads are referred to herein as anagrelide loaded beads. The anagrelide loaded beads are used to produce immediate release and control release formulations. Coating solutions can be prepared for the drug-loaded beads. Dosage forms (including tablets and capsules) can be prepared from the controlled release beads or a combination of immediate release beads and controlled release beads to achieve the desired release profile of the platelet number reducing agent, such as anagrelide, 3-OH anagrelide or analogs or derivatives thereof.

G. Articles of Manufacture

The controlled release compositions including a platelet number reducing agent as described herein can be packaged as articles of manufacture containing packaging material, within the packaging material a controlled release composition including a platelet number reducing agent as described herein, which is effective for reducing platelet number in a subject, or for prevention or amelioration of one or more symptoms of a disease or disorder characterized by elevated platelet count, or diseases or disorders in which platelets are implicated, and a label that indicates that the composition including a platelet number reducing agent as described herein is used to reduce platelet number in a subject or for treatment, prevention or amelioration of one or more symptoms of platelet-mediated diseases or disorders, or diseases or disorders in which platelets implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, tubes, inhalers, pumps, bags, vials, containers, syringes, bottles, and any packaging material suitable for a selected formulation and intended mode of administration and treatment. The controlled release compositions provided herein are contemplated for treatment for any disease or disorder in which platelets are a mediator or contributor to the symptoms or cause.

In certain embodiments, the controlled release compositions including a platelet number reducing agent as described herein can be presented as pharmaceutical compositions presented in a pack or dispenser device which can contain one or more unit dosage forms containing a controlled release composition including a platelet number reducing agent as described herein. The pack can, for example, contain metal or plastic foil, such as a blister pack. The pack or dispenser device can be accompanied by instructions for administration. The pack or dispenser also can be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a controlled release composition including a platelet number reducing agent as described herein formulated in a compatible pharmaceutical carrier also can be prepared, placed in an appropriate container, and labeled for treatment of an indicated condition.

H. Assays for Determining Activity of Platelet Number Reducing Agents

Some agents that reduce platelet count also can impact upon other cell lineages, particularly other hemopoietic cell lineages. In the methods provided herein, the platelet number reducing agent can be selected so that, while perhaps not exclusive for the megakaryocyte lineage, it has limited specificity for other cell types. One way of testing putatively useful agents is to perform in vitro assays in which platelets or platelet precursors (e.g., megakaryocytes, or megakaryocyte precursors) are exposed to a test compound after which their morphology (for example using an appropriate cell staining technique such as Wright's stain), number (for example using a Coulter counter) and/or colony forming ability are tested. These latter assays can be performed using either cell lines known to differentiate into the megakaryocyte lineage, or to the megakaryocyte lineage, several of which have been established in the prior art and examples of which include the Ba/F3 and UT-7/GM cell lines, or primary hemopoietic tissue, such as bone marrow. The number and quality of megakaryocyte colonies can be determined as a function of the presence and absence of the putatively useful agents.

The assays can be carried out by culturing the cells in a semi-solid culture in an amount of thrombopoietin sufficient to stimulate maximal megakaryocyte colony growth from the cell population. The putatively useful agent is then titrated into the cultures in order to determine the amount necessary to reduce megakaryocyte colony formation. In this manner, in addition to the amount of putatively useful agent necessary to inhibit megakaryocyte growth altogether, one can also determine an amount that inhibits the growth by a particular percentage. For example, if it desirable to reduce megakaryocyte growth and proliferation by 50% in order to achieve a reduction in platelet count in vivo, then the assay can be used to determine that amount of putatively useful agent necessary to inhibit megakaryocyte colony growth by 50%. An important benefit of a clonogenic assay is the ability to analyze the effect of the putatively useful agents on a wide variety of hemopoietic cell types. Since it is possible, with a correct cocktail of growth factors, to stimulate the growth of a variety of hemopoietic lineages in culture, the effect of the putatively useful agent on each lineage can be studied. Thus, putatively useful agents can be further screened for their selective action on the megakaryoctye lineage. Clonogenic assays are routinely employed by artisans of ordinary skill and are amenable to high-throughput screening.

Another way of measuring the biological activity of a putatively useful agent is to perform in vivo assays in which animals, such as mice, are injected, for example intravenously, with the compound and then analyzed for megakaryocyte growth and proliferation or platelet production. Hemopoietic populations, such as bone marrow and spleen, can be harvested from treated animals and plated into in vitro semi-solid clonogenic cultures in order to determine the effect of the putatively useful agent on megakaryocytes. The number and quality of megakaryocyte colonies derived from test animals should be compared to that of animals injected with control carrier (e.g., saline). Alternatively, animals can be assayed directly for platelet counts. This can be done in a number of ways including by bleeding the animals (usually from the tail or retro-orbital vein) and counting the number of platelets either manually using a hemocytometer or through the use of an automated cell counter, such as a Coulter counter.

Adverse side effects can also be tested in animals injected with putatively useful agents in this manner. One possible adverse side effect can be an inability to clot due to a severe reduction in platelets. To assess clotting function, standard bleeding assays can be employed, which measure the time required for bleeding from an experimentally induced wound to clot and thus stop. Platelet count and bleeding assays are routinely performed in human subjects as a measure of platelet count and platelet activity. Human subjects with a platelet count of more than $100 \times 10^3$ asymptomatic and their bleeding times are within the normal range. Bleeding times of less than 10 minutes are considered normal. When platelet count falls below $100 \times 10^3$ platelets per the bleeding time is extended and appears to be linearly related to the platelet count. Human subjects with a platelet count of less than $50 \times 10^3$ experience easy bruising, while those with a platelet count of less than $20 \times 10^3$ platelets routinely practiced by those of ordinary skill in the art and are taught in Harrison's *Principles of Internal Medicine*, Isselbacher, McGraw Hill, New York (1994).

I. Methods of Use of the Compositions

Provided herein are methods for reducing platelet count in a subject. In one embodiments, the method includes the steps of administering to a subject a controlled release composition of a platelet number reducing agent in a form that has a shelf stability of at least 3 months, and where the composition delivers an amount of the platelet number reducing agent effective to reduce platelet count in the subject by at least 10% of pre-treatment levels, where the controlled release composition releases the platelet reducing agent in an amount that does not overtly cause clinical symptoms that prevent or limit therapeutic use of the platelet number reducing agent. In some embodiments, the platelet reducing agent is in a hydrated crystal form. In some embodiments, the hydrated crystal form of the platelet-reducing agent is substantially maintained for a shelf period of at least 6 months. In some embodiments, the hydrated crystal form of the platelet-reducing agent is substantially maintained for a shelf period of at least 12 months.

Another embodiment provides a method for reducing platelet count in a subject, where the method includes administering to a subject a controlled release composition as described herein, where the composition delivers an amount of the platelet number reducing agent effective to reduce platelet count in the subject by at least 10% of pre-treatment levels, where the controlled release composition delivers the platelet reducing agent at a rate and in an amount that does not Overtly cause clinical symptoms that prevent or limit therapeutic use of the platelet number reducing agent.

Methods in which the controlled release compositions including a platelet number reducing agent as described herein are used, such as administered for treatment, alone or in combination with an immediate release formulation of the platelet number reducing agent, are provided. The methods include administering the controlled release compositions including a platelet number reducing agent as described herein to a subject for reducing platelet number in the subject and for treatment, prevention and/or amelioration of one or more symptoms of diseases or disorder in which platelets are implicated, such as thrombotic or thromboembolic events, vascular disease and myeloproliferative disorders.

The relevance of platelet number in the population considered to have a normal platelet count has been suggested by the finding that coronary heart disease mortality in otherwise healthy men is elevated in subjects with high-normal platelet counts (e.g., see Thaulow et al., Circulation 84: 613-617 (1991)). In addition, an analysis of results of the CADILLAC trial (a prospective randomized 2 by 2 factorial design study of PTCA vs. stenting and abciximab vs. no abciximab in over two thousand patients immediately after myocardial infarction) indicated that patients with higher platelet counts had higher peak myocardial enzyme levels, suggesting that patients with higher platelet counts had extensive thrombosis and larger infarcts (e.g., see Stone et al. N Eng J Med 346: 957-966 (2002) and Nikolsky et al., Am J Cardiol 99: 1055-1061 (2007). Lowering normal platelet count only modestly with low doses of anagrelide (to the low normal range, a level that does not impair hemostasis) will markedly decrease the incidence of atherothrombotic events and exhibit a more favorable risk/benefit profile than aspirin or clopidogrel. Further, a platelet lowering therapy in combination with aspirin and/or clopidogrel will further enhance antithrombotic efficacy without significant additional risk.

For subjects having a myeloproliferative disorder, such as essential thrombocythemia, platelet counts are greatly elevated and occlusive cardiovascular events are common. In essential thrombocythemia, reduction of platelet number has been recognized as an important factor in reducing atherothrombotic risk (e.g., Cortelazzo et al., J Clin Oncol 8: 556-562 (1990) and Fenaux et al., Cancer 66: 549-556 (1990). Lowering the platelet count pharmacologically reduces the risk of such events.

Thus, subjects, including those with normal levels of circulating platelets and those with elevated circulating platelet number, such as is common in certain myeloproliferative diseases or disorders, can derive medical benefit from a reduction in platelet count to low or below normal levels, without serious adverse consequences as a result of the platelet count reduction. The benefit can be proportional or correlative to the reduction in platelet count in a broad safety range. Thus in situations where it is desirable to inhibit a pathological condition or process mediated in part by normal levels of circulating platelets, subjects can be treated to lower platelet count to a low normal or below normal level, thereby inhibiting the development, progression or propagation of the condition or accelerating or enhancing its regression. In some embodiments the methods reduce the number of circulating platelets in a subject diagnosed with a myeloproliferative disease, such as essential thrombocythemia, idiopathic myelofibrosis or polycythemia vera, from an elevated level to near normal, normal, or low normal levels. The methods provided herein also are useful for reducing the incidence of abnormal vessel growth induced by the presence of platelets.

Provided herein are methods for treating a subject to reduce the risk of developing an adverse condition or to inhibit the progression and consequences of an adverse condition mediated at least in part by platelets. In one embodiment, the subject is treated to reduce platelet count to low normal levels. The methods include administering a pharmaceutically effective amount of a controlled release composition including a platelet number reducing agent as described herein, thereby reducing platelet count in the subject.

Also provided are methods for treating subjects who would benefit from lowering the number of circulating platelets. For example, provided are methods for treating subjects who would benefit from inhibiting the growth of an existing thrombus or lowering of the risk of a vaso-occlusive event such as a thrombotic event. Also provided are methods to reduce platelet count in a subject, including to normal levels in subjects that have high platelet counts, and to a low normal or below normal level in subjects having normal platelet counts for preventing or treating a vaso-occlusive event. Also provided are methods for treating subjects who have been diagnosed with a vascular disease. Also provided are methods for treating subjects who have been diagnosed with a hematological proliferative disorder, such as a myeloproliferative disease or disorder, including essential thrombocythemia, polycythemia vera and idiopathic myelofibrosis. Also provided are methods for treating subjects who will undergo or those who have already undergone a surgical or mechanical interventional procedure for the purposes of vessel repair and/or revascularization.

In some embodiment of the methods provided herein, the subject is otherwise free of symptoms calling for treatment with a platelet number reducing agent. The subject can be apparently healthy. In some embodiments, the subject does not exhibit symptoms that ordinarily call for treatment specifically with an agent which reduces platelet count. As an example, the subject can be otherwise free of signs, symptoms or evidence of disorders for which anagrelide would normally be prescribed (e.g., myeloproliferative disease). In some embodiments, the subject has been diagnosed with a myeloproliferative disease or disorder. In some embodiments, the subject has been diagnosed with polycythemia vera. In some embodiments, the subject has been diagnosed with essential thrombocythemia. In some embodiments, the subject has been diagnosed with idiopathic myelofibrosis. In some embodiments, the subject has an abnormally elevated platelet level (i.e., a platelet count that is higher than the normal range) that is not caused by a hematological proliferative disorder. In some embodiments, the subject can have a platelet count above the normal range, but without any underlying hematological proliferative disorder. In some embodiments, the subject is has not been diagnosed with a hematological proliferative disorder (such as myeloproliferative disease or disorder) that indicates the need for platelet number lowering therapy. In some embodiments, the subject has a normal platelet count prior to treatment. In some embodiments, the subject has a higher platelet count than the mean normal level but is still considered within the normal range. As an example, a subject with a platelet count of $450 \times 10^3$
to be at the high end of the normal range and is intended to be treated by the methods provided herein.

In the methods provided herein, the number of circulating platelets in a subject can be reduced to near normal or normal levels in subjects that have high platelet counts, and to a low normal or below normal level in subjects having normal platelet counts for preventing or treating a vaso-occlusive event.

The methods include administering controlled release compositions including a platelet number reducing agent as described herein in a dosage that results in reductions in platelet counts. In some embodiments, the methods include administering to a subject with a myeloproliferative disorder a composition as described herein to reduce circulating platelets resulting in platelet counts to a medically acceptable level. In some embodiments, the methods include administering to a subject with a myeloproliferative disorder a composition as described herein to reduce circulating platelets resulting in platelet counts of a medically acceptable level. In some embodiments, the methods include administering to a subject with a myeloproliferative disorder a composition as described herein to reduce circulating platelets resulting in platelet counts of equal to or less than $1,000 \times 10^3$, $950 \times 10^3$, $900 \times 10^3$, $850 \times 10^3$, $800 \times 10^3$, $750 \times 10^3$, $700 \times 10^3$ or $650 \times 10^3$, $600 \times 10^3$, $590 \times 10^3$, $580 \times 10^3$, $570 \times 10^3$, $560 \times 10^3$, $550 \times 10^3$, $540 \times 10^3$, $530 \times 10^3$, $520 \times 10^3$, $510 \times 10^3$, $500 \times 10^3$, $490 \times 10^3$, $480 \times 10^3$, $470 \times 10^3$, $460 \times 10^3$, $450 \times 10^3$, $440 \times 10^3$, $430 \times 10^3$, $420 \times 10^3$, $410 \times 10^3$, $400 \times 10^3$, $390 \times 10^3$, $380 \times 10^3$, $370 \times 10^3$, $360 \times 10^3$, $350 \times 10^3$, $340 \times 10^3$, $330 \times 10^3$, $320 \times 10^3$, $310 \times 10^3$, $300 \times 10^3$, $290 \times 10^3$, $280 \times 10^3$, $270 \times 10^3$, $260 \times 10^3$, $250 \times 10^3$, $240 \times 10^3$, $230 \times 10^3$, $220 \times 10^3$, $210 \times 10^3$, $200 \times 10^3$, $190 \times 10^3$, $180 \times 10^3$, $170 \times 10^3$, $160 \times 10^3$ or $150 \times 10^3$ In some embodiments, the methods include administering to a subject with a cardiovascular disease or thrombotic or vaso-occlusive disorder or a patient at risk for a cardiovascular disease or a thrombotic or vaso-occlusive disorder a composition as described herein to reduce circulating platelets resulting in platelet counts of equal to or less than $410 \times 10^3$, $400 \times 10^3$, $390 \times 10^3$, $380 \times 10^3$, $370 \times 10^3$, $360 \times 10^3$, $350 \times 10^3$, $340 \times 10^3$, $330 \times 10^3$, $320 \times 10^3$, $310 \times 10^3$, $300 \times 10^3$, $290 \times 10^3$, $280 \times 10^3$, $270 \times 10^3$, $260 \times 10^3$, $250 \times 10^3$, $240 \times 10^3$, $230 \times 10^3$, $220 \times 10^3$, $210 \times 10^3$, $200 \times 10^3$, $190 \times 10^3$, $180 \times 10^3$, $170 \times 10^3$, $160 \times 10^3$ or $150 \times 10^3$ In some embodiments, platelet count is reduced to below $250 \times 10^3$ but greater than or equal to $150 \times 10^3$
embodiments, the platelet count is reduced to $150 \times 10^3$ platelets/µl. In some embodiments, platelet count is reduced to below $150 \times 10^3$
$100 \times 10^3$ In some instances, it can be desirable to treat subjects having a platelet count in the normal range in order to reduce their platelet count and thereby reduce the risk of a vaso-occlusive event even if the post-treatment platelet count is still in the normal range. As an example, the methods provided herein can be used to treat a subject who has a platelet count of $450 \times 10^3$ platelets/µl which while high, is still in the normal range. The subject can be treated in order to reduce the platelet count to a lower level within the normal range (e.g., a low normal level, as described herein) or to a below normal level.

Reduction in platelet number can be measured as a percentage of the pre-treatment platelet count in a subject. Thus the controlled release compositions including a platelet number reducing agent as described herein can be administered in an amount effective to reduce platelet count from at least 10% to at least 95% of pre-treatment levels. In some embodiments, the controlled release compositions including a platelet number reducing agent as described herein are administered in an amount effective to reduce platelet count by at least 20%, at least 30%, at least 40%, at least 50%, at least 60%, at least 70%, at least 80%, or at least 90% of pre-treatment levels. In some embodiments, the subjects are normal subjects who do not have an abnormally high level of circulating platelets such as a platelet count greater than $500 \times 10^3 \times 10^3$ platelets per subjects are normal subjects who have a high level of circulating platelets that is within the normal range. In some embodiments, the subject can have a platelet count above the normal range, yet not have a hematological proliferative disorder. In some embodiments, platelets are reduced by at least 20% of pre-treatment levels. In some embodiments, platelets are reduced by at least 20% to at least 90% of pre-treatment levels. In still other embodiments, platelets are reduced by over 50% of pre-treatment levels.

The subjects can be treated so as to achieve a drop in platelet count below an absolute level (such as for example below $200 \times 10^3$
percentage drop in platelet count relative to pre-treatment levels (such as for example at least 10%). As an example, a subject can be treated so as to reduce platelet count by at least 20% and to achieve a platelet count of less than $200 \times 10^3$ The treatment methods provided herein includes administering to a subject a controlled release composition as described herein that includes an agent that reduces circulating platelet number in the subject. Any agent that reduces circulating platelet numbers can be used in the methods provided herein. Exemplary platelet number reducing agents include anagrelide, 3-OH anagrelide and all of the aforementioned active metabolites, analogs and/or derivatives of anagrelide. Another exemplary platelet number reducing agent is hydroxyurea, alone or in combination with anagrelide, 3-OH anagrelide and all of the aforementioned active metabolites, analogs and/or derivatives of anagrelide.

In some embodiments, a platelet number reducing agent having the specific effect of reducing only circulating platelet count without affecting levels of other cell types is selected. In some embodiments, a platelet number reducing agent is selected that reduces platelet number and also can reduce levels of other cell types, provided these latter reductions do not induce unacceptable levels of adverse side effects associated with such reduction in other cell types. For example, the agent can reduce the ploidy of megakaryocytes, the precursors of platelets, reducing the rate at which platelets are produced, without having any undesirable clinically important side effect on other cell types. In still another example, the agent can inhibit megakaryocyte function. It will be apparent to persons of ordinary skill in the art how to select and distinguish between such agents.

In some embodiments, the methods treat subjects who are at risk of a vaso-occlusive event. These subjects can or can not have had a previous vaso-occlusive event. In some embodiments, the methods treat subjects prior to a vaso-occlusive event, at a time of a vaso-occlusive event and/or following a vaso-occlusive event. In one embodiment, the subject can exhibit symptoms of a vaso-occlusive event. In some embodiments, the methods treat a subject that has an abnormally elevated risk of a vaso-occlusive event such as a thrombotic event. The subject can have a vascular disease. The vascular disease can be selected from among arteriosclerosis, cardiovascular disease, cerebrovascular disease, renovascular disease, mesenteric vascular disease, pulmonary vascular disease, ocular vascular disease or peripheral vascular disease.

In some embodiments, the subject to be treated has had a primary vaso-occlusive event, such as a primary thrombotic event. In some embodiments, a subject is treated to reduce the risk of a secondary thrombotic event or to inhibit the propagation of an existing thrombotic event. The thrombotic event can be selected from among arterial thrombosis, coronary thrombosis, heart valve thrombosis, coronary stenosis, stent thrombosis and graft thrombosis. The vaso-occlusive event also includes disorders or conditions that can arise from a thrombotic event or a thromboembolic event and in this regard a vaso-occlusive event includes, but is not limited to, myocardial infarction, stroke and transient ischemic attack. In some embodiments, the vaso-occlusive event is myocardial infarction. In one embodiment, the subject has had a myocardial infarction. A subject who has hypercholesterolemia, hypertension or atherosclerosis also can be treated by the methods provided herein. In one embodiment, provided is a method for treating a subject to reduce morbidity or mortality of the subject from a vaso-occlusive event, such as but not limited to thrombotic events that can lead to total or partial vessel blockage by thrombus, or arterial stenosis due to excessive cell proliferation.

In the method provided, a controlled release composition described herein is administered in an amount effective to deliver a dosage that reduces platelet count in the subject. In one embodiment, platelet count is reduced to at least low normal levels.

In some embodiments, the methods include administering a controlled release composition as described herein where the platelet number reducing agent is anagrelide. In one embodiment, the platelet number reducing agent is 3-OH anagrelide. In one embodiment, the platelet number reducing agent is a derivative of anagrelide. In one embodiment, the platelet number reducing agent is an analog of anagrelide.

In one embodiment, the platelet number reducing agent is administered in an amount ranging from at or about 1 ng/kg/day to at or about 500 ng/kg/day.

In one embodiment, the platelet number reducing agent is administered in an

In some embodiments, the platelet number reducing agent is administered in an embodiments, the platelet number reducing agent is administered in an amount ranging platelet number reducing agent is administered in an amount ranging from at or about 0.5 about 150 µg/kg/day. In some embodiments, the platelet number reducing agent is embodiments, the platelet number reducing agent is administered in an amount of 0.1, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, In some embodiments, the methods include administration of the controlled release number reducing agent, administered as a single dose or as 2-4 divided doses. In some embodiments, the controlled release compositions provided herein are provided as a dosage form that includes a dosage of a platelet number reducing agent of from 50 µg to provided as a dosage form that includes a dosage of a platelet number reducing agent of provided herein are provided as a dosage form that includes a dosage of a platelet number reducing agent of from 200 µg to 500 µg. In some embodiments, the controlled release compositions provided herein are provided as a dosage form that includes a dosage of a 200 µg, 205 µg, 210 µg, 215 µg, 220 µg, 225 µg, 230 µg, 235 µg, 240 µg, 245 µg, 250 µg, 475 µg, 480 µg, 485 µg, 490 µg, 495 µg, 500 µg, 505 µg, 510 µg, 515 µg, 520 µg, 525 µg, 750 µg, 755 µg, 760 µg, 765 µg, 770 µg, 775 µg, 780 µg, 785 µg, 790 µg, 795 µg, 800 µg, In some embodiments, the dosage of platelet number reducing agent is selected from among at or about 10 ng to at or about 100 ng, at or about 10 ng to at or about 250 ng, at or about 10 ng to at or about 500 ng, at or about 10 ng to at or about 100 ng, at or about 10 ng to at or about 1000 ng, at or about 25 ng to at or about 250 ng, at or about 50 ng to at or about 500 ng, at or about 75 ng to at or about 750 ng, at or about 100 ng to at or about 1000 ng, at or about 250 ng to at or about 2500 ng, at or about 500 ng to at or about 5000 ng, at or about 750 ng to at or about 7500 ng and at or about 1000 ng to at or about 10000 ng. In some embodiments, the dosage of platelet number reducing agent is 10 ng, 20 ng, 30 ng, 40 ng, 50 ng, 60 ng, 70 ng, 80 ng, 90 ng, 100 ng, 125 ng, 150 ng, 175 ng, 200 ng, 225 ng, 250 ng, 275 ng, 300 ng, 325 ng, 350 ng, 375 ng, 400 ng, 425 ng, 450 ng, 475 ng, 500 ng, 525 ng, 550 ng, 575 ng, 600 ng, 625 ng, 650 ng, 675 ng, 700 ng, 725 ng, 750 ng, 775 ng, 800 ng, 825 ng, 850 ng, 875 ng, 900 ng, 925 ng, 950 ng, 975 ng or 1000 ng. In some embodiments, the dosage of platelet number reducing agent is 1 µg, 1.25 µg, 1.5 µg, 1.75 µg, 2 µg, 2.25 µg, 2.5 µg, 2.75 µg, 3 µg, 3.25 µg, 3.5 µg, 3.75 µg, 4 µg, 4.25 µg, 4.5 µg, 4.75 µg, 5 µg, 5.25 µg, 5.5 µg, 5.75 µg, 6 µg, 6.25 µg, 6.5 µg, 6.75 µg, 7 µg, 7.25 µg, 7.5 µg, 7.75 µg, 8 µg, 8.25 µg, 8.5 µg, 8.75 µg, 9 µg, 9.25 µg, 9.5 µg, 9.75 µg or 10 µg. In some embodiments, the dosage of platelet number reducing agent is 725 µg, 750 µg, 775 µg, 800 µg, 825 µg, 850 µg, 875 µg, 900 µg, 925 µg, 950 µg, 975 µg or 1000 µg.

K. Combination Therapies

In some embodiments, the controlled release compositions including a platelet number reducing agent as described herein is formulated to include another agent, such as another platelet number reducing agent, or another agent that would normally be indicated for the subject. In some embodiments, the controlled release compositions including a platelet number reducing agent as described herein are administered with another agent, such as an agent that would normally be indicated for the subject. In some embodiments, the controlled release compositions including a platelet number reducing agent as described herein can be administered substantially simultaneously with the other therapeutic agents. By substantially simultaneously, it is meant that a controlled release composition including a platelet number reducing agent as described herein is administered to a subject close enough in time with the administration of the other therapeutic agent, whereby the two compounds can exert an additive or even synergistic effect, e.g., decreasing platelet number and inhibiting their ability to aggregate. In other embodiments, the controlled release compositions including a platelet number reducing agent as described herein can be administered before or after the administration of the other therapeutic agent.

The controlled release compositions including a platelet number reducing agent as described herein can include or be administered with several categories of therapeutic agents. These agents can be classified in terms of their function or in terms of the disorders for which they are indicated. Several useful categories of such agents include, but are not limited to, platelet adhesion inhibitors, platelet aggregation inhibitors, plasminogen activator receptor (PAR) inhibitors, anti-inflammatory agents, anti-thrombotic agents, ADP receptor antagonists, platelet adhesion inhibitors, glycoprotein receptor inhibitors, cyclooxygenase inhibitors, fibrinolytic agents, lipid reducing agents, renin-angiotensin system inhibitors, antihypertensive agents, compounds that irreversibly bind to $P2Y_{12}$ receptors, chemotherapeutic anti-cancer drugs and alkylating agents such as hydroxyurea, thromboxane synthetase inhibitors, compounds that inhibit thromboxane $A_2$ formation, cell signaling molecules and JAK-2 inhibitors.

1. Platelet Adhesion Inhibitors

One broad category of agents that can be included in the compositions provided herein or administered with the controlled release compositions provided herein includes platelet adhesion inhibitors. These include compounds that strongly bind to collagen, inhibiting platelet adhesion to collagen (e.g., see U.S. Pat. No. 7,090,986 and Morita et al., FEBS Journal 273: 2955-2962 (2006)). Platelet adhesion inhibitors can be identified using assays known in the art, such as the platelet adhesion inhibitor assay described in U.S. Pat. No. 5,686,571 and U.S. Pat. App. Pub. 20070202108. Exemplary platelet adhesion inhibitors include, but are not limited to, calin, jararhagin, leech anti-platelet protein (LAPP), saratin and triplatin.

2. Platelet Aggregation Inhibitors

Another broad category of agents that can be included in the compositions provided herein or administered with the controlled release compositions provided herein includes platelet aggregation inhibitors. Any platelet aggregation inhibitor can be included in the compositions or administered in combination with the compositions provided herein. Several classes of peptides have been described in the art that block the binding of adhesive proteins to activated platelets and inhibit platelet aggregation (e.g., see U.S. Pat. Nos. 4,578,079, 4,614,517, 4,661,471, 4,792,525 and 5,318,899). Among the platelet aggregation inhibitors are low molecular weight polypeptide factors, such as those from snake venoms, which have extremely high affinity for the GP IIb/IIIa complex (e.g., see Gan et al., J Biol Chem 263: 19827-19832 (1988); Huang et al., J Biol Chem 262:16157-16163 (1987); and Huang et al., Biochemistry 28:661-666 (1989)). Platelet aggregation inhibitors include fibrinogen receptor antagonists (i.e., glycoprotein IIb/IIIa fibrinogen receptor antagonists). Murine anti-GP IIb/IIIa monoclonal antibodies also block the binding of the adhesive proteins to stimulated platelets. Such monoclonal antibodies have been used to prevent coronary artery reocclusion after reperfusion with tissue plasminogen activator in dogs (see, e.g., Yasuda et al., J Clin Invest 81: 1284-1291 (1988)). Exemplary platelet aggregation inhibitors include, but are not limited to, albolabrin, applaggin, aspirin, barbourin, basilicin, batroxostatin, bitistatin, cerastin, clopidogrel, cotiarin, crotatroxin, dipyridamole, echistatin, elegantin, eristicophin, flavoviridin, halysin, hementin, horridin, ifetroban, lachesin, lutosin, molossin, moubatin, pallidipin, ruberin, salmosin, saxatlilin, tergeminin, ticlopidine, trigramin and viridian.

3. Anti-Inflammatory Agents

Another broad category of agents that can be included in the compositions provided herein or administered with the controlled release compositions provided herein containing a platelet number reducing agents includes anti-inflammatory agents. Anti-inflammatory agents include alclofenac; alclometasone dipropionate; algestone acetonide; alpha amylase; amcinafal; amcinafide; amfenac sodium; amiprilose hydrochloride; anakinra; anirolac; anitrazafen; apazone; balsalazide disodium; bendazac; benoxaprofen; benzydamine hydrochloride; bromelains; broperamole; budesonide; carprofen; cicloprofen; cintazone; cliprofen; clobetasol propionate; clobetasone butyrate; clopirac; cloticasone propionate; cormethasone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; flufenamic acid; flumizole; flunisolide acetate; flunixin; flunixin meglumine; fluocortin butyl; fluorometholone acetate; fluquazone; flurbiprofen; fluretofen; fluticasone propionate; furaprofen; furobufen; halcinonide; halobetasol propionate; halopredone acetate; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lornoxicam; loteprednol etabonate; meclofenamate-sodium; meclofenamic acid; meclorisone dibutyrate; mefenamic acid; mesalamine; meseclazone; methylprednisolone suleptanate; morniflumate; nabumetone; naproxen; naproxen sodium; naproxol; nimazone; olsalazine sodium; orgotein; orpanoxin; oxaprozin; oxyphenbutazone; paranyline hydrochloride; pentosan polysulfate sodium; phenbutazone sodium glycerate; pirfenidone; piroxicam; piroxicam cinnamate; piroxicam olamine; pirprofen; prednazate; prifelone; prodolic acid; proquazone; proxazole; proxazole citrate; rimexolone; romazarit; salcolex; salnacedin; salsalate; salicylates; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triclonide; triflumidate; zidometacin; glucocorticoids; and zomepirac sodium. One particular anti-inflammatory agent is aspirin.

4. Plasminogen Activator Receptor Antagonists

Another broad category of agents that can be included in the compositions provided herein or administered with the controlled release compositions provided herein containing a platelet number reducing agent includes plasminogen activator receptor (PAR) antagonists.

There are two known plasminogen activators: urokinase or uPA and tissue plasminogen activator or tPA. Both enzymes are present in plasma and play a critical role in fibrinolysis. Although tPA appears to be the key plasminogen activator in plasma, urokinase is associated with cell surface plasminogen activation as a result of binding to a specific cell surface urokinase receptor (uPAR, CD87). The uPAR plays a critical role in the regulation of cellular plasminogen activation. Since plasminogen is also cell surface bound, the process of plasmin generation proceeds more effectively at the cell surface, and plasmin itself is less susceptible to inhibition when active at the cell surface (e.g., see Andreasen et al., International Journal of Cancer 72: 1-22 (1997)). The known plasminogen activators differ significantly in characteristics such as their biological half-lives and their preference for fibrin. Plasminogen activators have been widely used as thrombolytic agents, such as for the treatment of thrombosis in myocardial infarction, stroke and arterial occlusion (e.g., see U.S. Pat. Nos. 5,098,840, 5,004,609, 4,851,345 and 4,258,030). Antagonists can be antibodies, peptides, proteins, nucleic acids or small organic molecules. Exemplary PAR antagonists include 2-alkylidene hydroxycumaranone derivatives as described in U.S. Pat. No. 6,200,989, cyclo [21,29] [D-Cys21Cys29]-uPA2,-3o and mimetics thereof, as described in U.S. Pat. App. Pub. No. US2003232389, spironolactone, imidapril, angiotensin converting enzyme inhibitors (ACEI, captopril, or enalapril), angiotensin II receptor antagonist (AIIRA), defibrotide (a polydeoxyribonucleotide), and porphyrins as described in EP0792647.

5. Anti-Thrombotic Agents

Another broad category of agents that can be included in the compositions provided herein or administered with the controlled release compositions provided herein containing a platelet number reducing agent includes anti-thrombotic agents. Anti-thrombotic agents include agents that prevent the formation of a blood thrombus via a number of potential mechanisms and they include fibrinolytic agents, anti-coagulant agents and inhibitors of platelet function. Anti-thrombotic agents include chemical and biological compounds that can intervene at any stage in the coagulation pathway. Examples of specific compounds include, but are not limited to, small molecules that inhibit the activity of factor Xa and heparinoid-type agents that can inhibit factor Xa and thrombin, either directly or indirectly, such as, for example, heparin, heparin sulfate, low molecular weight heparins, such as that marketed under the trademark CLIVARIN®, and synthetic oligosaccharides, such as that marketed under the trademark ARIXTRA®. Also included are direct thrombin inhibitors, such as, for example, melagatran, ximelagatran, argatroban, inogatran, and peptidomimetics of the binding site of the Phe-Pro-Arg fibrinogen substrate for thrombin. Another class of anti-thrombotic agents includes factor VII/VIIa inhibitors, such as, for example, anti-factor VII/VIIa antibodies, rNAPc2, and tissue factor pathway inhibitor (TFPI). Anti-thrombotic agents also include abbokinase, anisoylated plasminogen-streptokinase activator complex, bivalirudin, dalteparin sodium, danaparoid sodium, dazoxiben hydrochloride, dextrans, efegatran sulfate, eminase, enoxaparin sodium, ifetroban and ifetroban sodium, plasminogen, reteplase, streptokinase, tinzaparin sodium, trifenagrel, urokinase and pro-urokinase and warfarin.

6. ADP Receptor Antagonists

Another broad category of agents that can be included in the compositions provided herein or administered with the controlled release compositions provided herein containing a platelet number reducing agent includes ADP receptor antagonists. These drugs act by non-competitive antagonism at one of the platelet adenosine diphosphate (ADP) receptors, the P2Y12 receptor. The P2Y12 receptor inhibits cyclic adenosine monophosphate production and potentiates platelet aggregation. Exemplary ADP receptor antagonists include the thienopyridine derivatives clopidogrel (marketed under the trademark PLAVIX®), ticlopidine and prasugrel (also known as CS-747 and to be marketed under the trademark EFFIENT™, was developed by Daiichi Sankyo Co., and is a thienopyridine prodrug), sulfinpyrazone, AZD6140, AZD6933 and AR-C69931 (an antagonist with effects similar to those of clopidogrel).

7. Glycoprotein IIb/IIIa Receptor Inhibitors

Another broad category of agents that can be included in the compositions provided herein or administered with the controlled release compositions provided herein containing a platelet number reducing agent includes glycoprotein IIb/IIIa receptor inhibitors. These agents inhibit cell surface receptors specifically expressed by platelets or megakaryocytes. Antagonists that bind to this receptor can reversibly or permanently inhibit platelet-platelet interaction. Antagonists of the glycoprotein IIb/IIIa receptor include polyclonal or monoclonal antibodies or Fab fragments that bind to the glycoprotein IIb/IIIa receptor and modulate fibrinogen and other adhesion ligands. An exemplary anti-glycoprotein IIb/IIIa receptor antibody is abciximab. Non-antibody, non-peptide orally active antagonists of the glycoprotein IIb/IIIa receptor include the arginine-glycine-aspartate-mimetic eptifibatide, which reversibly binds to platelets, fradafiban, lamifiban, lotrafiban, orbofiban, roxifiban, sibrafiban, tirofiban and xemilofiban.

8. Anti-Coagulant and/or Fibrinolytic Agents

Another broad category of agents that can be included in the compositions provided herein or administered with the controlled release compositions provided herein containing a platelet number reducing agent includes anti-coagulant and fibrinolytic agents. Anti-coagulant agents are agents that inhibit the coagulation pathway by impacting negatively upon the production, deposition, cleavage and/or activation of factors essential in the formation of a blood clot. Although the timing or administration is controversial, anti-coagulants can be started to prevent recurrent cardiogenic emboli. Clot lysing agents, including tissue plasminogen activator and streptokinase, are being evaluated for the very early treatment of acute stroke. Nimodipine has been shown to improve survival and clinical outcome after ischemic stroke. Anti-coagulant agents include but are not limited to vitamin K antagonists such as coumarin and coumarin derivatives (e.g., warfarin sodium); glycosoamino-glycans such as heparins in unfractionated form and in low molecular weight form; ardeparin sodium, bivalirudin, bromindione, coumarin dalteparin sodium, desirudin, dicumarol, lyapolate sodium, nafamostat mesylate, phenprocoumon, sulfatide, and tinzaparin sodium.

Fibrinolytic agents are defined as agents that lyse a thrombus (e.g., a blood clot), usually through the dissolution of fibrin by enzymatic action. Examples of thrombolytic agents include, but are not limited to, ancrod, anistreplase, bisobrin lactate, brinolase, Hageman factor (i.e., factor XII) fragments, molsidomine, plasminogen activators such as streptokinase, TFPI, tissue plasminogen activators (TPA) and urokinase, and plasmin and plasminogen. Anti-coagulant agents also include inhibitors of thrombin (FIIa), FVa, FVIIa, FVIIIa, FIXa, FXa, FXIa, FXIIa and FXIIIa.

Other anti-coagulant and/or fibrinolytic agents include urokinase:anisoylated plasminogen-streptokinase activator complex, pro-urokinase (Pro-UK), rTPA (alteplase or activase, where r denotes recombinant), rPro-UK, abboinase, Eminase, streptase, bivalirudin, dalteparin sodium, danaparoid sodium, dazoxiben hydrochloride, efegatran sulfate, enoxaparin sodium, ifetroban, ifetroban sodium, tinzaparin sodium, reteplase, trifenagrel, warfarin, dextrans, anti-coagulant citrate dextrose solution, anticoagulant citrate phosphate dextrose adenine solution, anticoagulant citrate phosphate dextrose solution and anticoagulant sodium citrate solution.

9. Lipid Reducing Agents

Another broad category of agents that can be included in the compositions provided herein or administered with the controlled release compositions provided herein containing a platelet number reducing agent includes lipid reducing agents and cholesterol modulating agents. For example, HMGCoA reductase inhibitors (commonly referred to as statins) have a well-known mechanism in controlling cholesterol metabolism and commonly are used to lower cholesterol levels in subjects with or at risk of cardiovascular disease. Exemplary lipid reducing agents and/or cholesterol modulating agents include amphipathic carboxylic acids, including the fibrates bezafibrate, ciprofibrate, clofibrate, etofibrate, fenofibrate, gemfibrozil, ronifibrate and simfibrate; statins, including atorvastatin, cerivastatin, fluvastatin, lovastatin, mevastatin, pitavastatin, pravastatin, rosuvastatin and simvastatin, niacin and niacin derivatives, including acipimox, aluminium nicotinate, niceritrol (pentaerythritol tetranicotinate), nicofuranose and nicotinyl alcohol, bile acid sequestrants, including colesevelam, colestyramine, colestipol and colextran, CETP inhibitors, such as anacetrapib, benfluorex, cholestyramine, dextrothyroxine, ezetimibe, laropiprant, meglutol, omega-3-triglycerides, policosanol, probucol and tiadenol.

10. Cyclooxygenase-2 (COX-2) Inhibitors

Another broad category of agents that can be included in the compositions provided herein or administered with the controlled release compositions provided herein containing a platelet number reducing agent includes cyclooxygenase-2 (COX-2) inhibitors. Non-steroidal, anti-inflammatory drugs exert most of their anti-inflammatory, analgesic and anti-pyretic activity and inhibit hormone-induced uterine contractions and certain types of cancer growth through inhibition of cyclooxygenase. By contrast, it is believed that the inducible form, COX-2, is mainly responsible for the pathological effects of prostaglandins where rapid induction of the enzyme occurs in response to such agents as inflammatory agents, hormones, growth factors, and cytokines. Selective inhibitors of COX-2 have anti-inflammatory, antipyretic and analgesic properties similar to a conventional non-steroidal anti-inflammatory drugs. In particular, COX-2 inhibitors are believed to have a reduced potential for gastro-intestinal toxicity, a reduced potential for renal side effects, a reduced effect on bleeding times and possibly a decreased potential to induce asthma attacks in aspirin-sensitive asthmatic subjects. Exemplary COX-2 inhibitors include aspirin, celecoxib (such as that marketed under the trademark CELEBREX®), lumiracoxib (such as that marketed under the trademark PREXIGE®), etoricoxib (such as that marketed under the trademark ARCOXIA®), meloxicam, nimesulide and those described in any of the following U.S. patents (U.S. Pat. Nos. 5,474,995; 5,521,213; 5,536,752; 5,552,422; 5,604,253; 5,604,260; 5,639,780; 5,643,933; 5,677,318; 5,691; 5,698,584; 5,710, 140; 5,733,909; 5,789,413; 5,817,700; 5,849,943; 5,861,419; 5,922,742; 5,925,631. Other COX-2 inhibitors include valdecoxib (such as that marketed under the trademark BEXTRA®) and rofecoxib (such as that marketed under the trademark VIOXX®), but these have been removed from the market. A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501; WO 95/18799 and U.S. Pat. No. 5,474,995.

11. Renin-Angiotensin System Inhibitors

Another broad category of agents that can be included in the compositions provided herein or administered with the controlled release compositions provided herein containing a platelet number reducing agent includes angiotensin system inhibitors. Angiotensin system inhibitors include agents that interfere with the function, synthesis or catabolism of angiotensin II. These agents include, but are not limited to, angiotensin converting enzyme (ACE) inhibitors, such as benazepril, captopril, delapril, enalapril, fosinopril, imidapril, lisinopril, moexipril, perindopril, quinapril, ramipril, spirapril, temocapril, trandolapril and zofenopril; angiotensin II receptor antagonists, such as azilsartan, candesartan, eprosartan, irbesartan, losartan, olmesartan, tasosartan, telmisartan and valsartan; agents that activate the catabolism of angiotensin II; and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of Na+ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance that has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs. Among the most potent and useful renin-angiotensin system inhibitors are renin inhibitors, ACE inhibitors, and angiotensin II antagonists. In some embodiments, the renin-angiotensin system inhibitors are renin inhibitors, ACE inhibitors, and angiotensin II antagonists.

Angiotensin II antagonists are compounds that interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(Sar$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzyl) imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboxylic acid and analog derivatives (U.S. Pat. No. 4,816, 463); N2-tetrazole beta-glucuronide analogs (U.S. Pat. No. 5,085,992); substituted pyrroles, pyrazoles, and triazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064, 825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(−1-naphthyl)-L-alanyl-(4, thiazolyl)-L-alanyl (35,45)-4-amino-3-hydroxy-5-cyclohexa-pentanoyl-N-hexylamide, Sankyo Company, Ltd., Tokyo, Japan); SKF108566 (E-alpha-2-[2-butyl-1-(carboxy phenyl)methyl]1H-imidazole-5-yl[methylene]-2-thiophenepropanoic acid, Smith Kline Beecham Pharmaceuticals, PA); Losartan (DUP753/MK954, DuPont Merck Pharmaceutical Company); Remikirin (R042-5892, Hoffman LaRoche AG); A$_2$ agonists (Marion Merrill Dow) and certain non-peptide heterocycles (G. D. Searle and Company).

Angiotensin converting enzyme (ACE), is an enzyme that catalyzes the conversion of angiotensin I to angiotensin II. ACE inhibitors include amino acids and derivatives thereof, peptides, including di- and tri-peptides and antibodies to ACE that intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazepril (U.S. Pat. No. 4,410,520), phosphinylalkanoyl prolines such as fosinopril (U.S. Pat. No. 4,337,201) and trandolapril.

12. Antihypertensive Agents

Another broad category of agents that can be included in the compositions provided herein or administered with the controlled release compositions provided herein containing a platelet number reducing agent includes antihypertensive agents. Exemplary antihypertensive agents include renin inhibitors, such as aliskiren, beta blockers, such as acebutolol, alprenolol, atenolol, betaxolol, bisoprolol, carteolol, esmolol, levobunolol, mepindolol, metipranolol, metoprolol, nadolol, nebivolol, oxprenolol, penbutolol, pindolol, propranolol, sotalol and timolol, adrenergic agonists, such as arotinolol, carvedilol, celiprolol, clonidine, doxazocin, guanethidine, guanfacine, indoramin, labetalol, lofexidine, methyldopa, moxonidine, prazosin, rilmenidine, hydralazine hydrochloride, vasodilators such as diazoxide, hydralazine, minoxidil, nitroprusside and phentolamine, serotonin antagonists such as ketanserin, and endothelin receptor antagonists such as ambrisentan, bosentan and sitaxsentan, reserpine, and diuretics, such as bendroflumethiazide, bumetanide, chlortalidone, chlorothiazide, cicletanine, furosemide, hydrochlorothiazide, indapamide, mersalyl, metolazone quinethazone, theobromine and torasemide.

13. Chemotherapeutic Anti-Cancer Drugs and Alkylating Agents

Another broad category of agents that can be included in the compositions provided herein or administered with the controlled release compositions provided herein containing a platelet number reducing agent includes chemotherapeutic anti-cancer drugs and alkylating agents. Many of the antineoplastic and chemotherapeutic cancer drugs can be used to reduce the number of circulating platelets. Some of the chemotherapeutic drugs are alkylating agents. Alkylating agents are compounds that cross-link or cleave DNA, inhibiting replication or causing irreparable modification, resulting in apoptosis. Exemplary chemotherapeutic cancer drugs that can be used to reduce platelet number include busulfan, carmustine, chlorambucil, cyclophosphamide, doxorubicin, estramustine, hepsulfan, hydroxycarbamide or hydroxyurea, ifosfamide, lomustine, melphalan, methotrexate, pipobroman and thioTEPA. (see, e.g., Br. J. Haematol. 62: 229-237 (1986), N Engl J Med 332:1132-1136 (1995), Br J Radiol 70: 1169-1173 (1997), Scand J. Haematol 37: 306-309 (1986) and J Cell Physiol 112: 222-228 (1982)).

14. Thromboxane Synthetase Inhibitors

Another category of agents that can be included in the compositions provided herein or administered with the controlled release compositions provided herein containing a platelet number reducing agent includes thromboxane synthetase inhibitors. Thromboxane synthetase inhibitors include pyridine and imidazole derivatives. An 1555), and exemplary imidazole derivatives include 1-carboxyhexyl-, 1-carboxyheptyl, and 1-carboxyoctyl-imidazoles. Other exemplary thromboxane synthetase inhibitors include 4(Z)-6-[(4RS,5SR)-4-(2-hydroxyphenyl)-1,3-dioxan-5-yl]hex-4-enoic acid, BM-573, camonagrel, CGS-12970, daltroban, dazmegrel, DTTX30, E-6700, FCE-27262, imitrodast (CS-518), isbogrel (CV-4151), ketoconazole, KK-505, KY-063, nafagrel (DP-1904), ozagrel (OKY-046), picotamide, pirmagrel (CGS-13080), ridogrel, SQ29548, rolafagrel (FCE-22178), satigrel (E-5510), sulotroban, terbogrel and UK 38485.

15. Cell Signaling Molecules

Another category of agents that can be included in the compositions provided herein or administered with the controlled release compositions provided herein containing a platelet number reducing agent includes cell signaling molecules. Cell signaling molecules, including cytokines, such as interleukin, also can be used to modulate platelet levels, such as by modulating conversion of megakaryocytes to platelets. Exemplary signaling molecules include cytokines, growth factors and interleukins such as α-interferon (Cancer Immunol Immunother 1987 25:266-73), γ-(U.S. Pat. No. 5,472,944), macrophage inflammatory protein and its analogs (U.S. Pat. No. 5,306,709), and compounds secreted by either platelets or megakaryocytes such as platelet-factor 4 (U.S. Pat. No. 5,185,323), thrombin and thrombospondin and its amino (1-174 amino acid) terminal fragment (J Lab Clin Med 129: 231-238 (1997)).

16. JAK-2 Inhibitors

Another category of agents that can be included in the compositions provided herein or administered with the controlled release compositions provided herein containing a platelet number reducing agent includes JAK-2 inhibitors. The Janus family kinases (JAKs) are a family of protein tyrosine kinases (PTK) that are critical for receptor-mediated signal transduction. JAKs are involved in membrane signalling events that are triggered by a variety of extracellular factors that interact with cell surface receptors. JAKs initiate the cytoplasmic signal transduction cascades of cytokine receptors that lack a protein tyrosine kinase domain. A somatic point mutation of the JAK-2 gene (an acquired V617F mutation) has been identified to be highly associated with classic myeloproliferative disorders (MPD) (e.g., see Campbell et al., Lancet 366: 1945-1953 (2005)). It has been found that the mutation occurs in most patients with polycythemia vera, and can be found in about half of the subjects diagnosed with essential thrombocythemia or idiopathic myelofibrosis. Hyperactivation of JAK-STAT signaling (signal transducers and activators of transcription (STAT) proteins) has been associated with a number of diseases or conditions, including myeloproliferative disorders, including essential thrombocythemia (ET), polycythemia vera (PV) and idiopathic myelofibrosis (IMF). JAK-2 inhibitors are under development. Exemplary inhibitors of JAK-2 include AT9283, VX-680, MK0457, TG101209, INCB018424, LS104, XLO19, TG101348, vorinostat, 4-aryl-2-amino-pyridines and 4-aryl-2-aminoalkyl-pyridines as described in WO/2007/089768 and the inhibitors described in U.S. Pat. No. 7,070,972.

K. Administration

In the methods provided herein, the controlled release compositions provided herein containing a platelet number reducing agent can be administered to a subject using any mode of administration that is medically acceptable, meaning any enteral or parenteral mode that produces effective levels of the active compounds without causing clinically unacceptable adverse effects. Exemplary of such modes of administration include oral, rectal, intracavitary, subcutaneous, intramuscular, transdermal or local routes.

The controlled release compositions provided herein containing a platelet number reducing agent are administered for a length of time sufficient to provide therapeutic and/or prophylactic benefit to the subject. Generally, the controlled release compositions provided herein containing a platelet number reducing agent are administered for at least one day. In some embodiments, the compositions provided herein are administered for at least one platelet turnover cycle, or from 5-10 days. In some embodiments, the compositions provided herein are administered for at least two platelet turnover cycles, or from 10-20 days. In some instances, particularly where a subject has had a vaso-occlusive event or where the subject is at risk of such an event, the controlled release compositions provided herein can be administered for the remainder of the subject's life. The rate at which the agent is administered is determined by the controlled release composition used, which can be varied depending upon the needs of the subject and the mode of administration. In some embodiments, lower doses are administered in order to maintain a desired platelet count once it is achieved. The frequency of administration can vary. The agent can be administered once daily, twice daily, four times daily, every 2 days, every 3 days, every 4 days, every 5 days, every week, every 10 days, every 2 weeks, every month, or more, or any time therebetween as if such time was explicitly recited herein.

In some embodiments, e.g., for treating a subject with a myeloproliferative disorder, one or more dosage forms, e.g., capsules or tablets, including a composition provided herein that includes a dose of a platelet number reducing agent of from at or about 300 µg to at or about 1000 µg, can be administered once a day or multiple times a day, taken with or without food. For example, two oral dosage forms, e.g., tablets or capsules, containing a composition provided herein, each containing a dose of a platelet number reducing agent of 1000 µg, can be administered four times a day in order to provide a dose of platelet number reducing agent of 8 mg per day. In some embodiments, up to at or about 10 mg of a platelet number reducing agent can be administered per day, where a single dose is at or about 2500 µg or less. In some embodiments, a dose of platelet number reducing agent of 1000 µg is administered twice a day. In some embodiments, a dose of platelet number reducing agent of 500 µg is administered four times a day. In some embodiments, a dose of platelet number reducing agent of 400 µg is administered twice times a day.

In some embodiments, e.g., for the prophylaxis or treatment of a thrombotic or vaso-occlusive event, or to inhibit, slow or delay the onset of a cardiovascular disease or disorder or an associated symptom thereof, one or more dosage forms including a composition provided herein that includes a dose of a platelet number reducing agent of from at or about 50 µg to at or about 1000 µg, can be administered once a day or multiple times a day, taken with or without food. Exemplary dosage forms include a dose of a platelet number reducing agent of at or about 1000 µg or less, including 1000 µg, 900 µg, 800 µg, 700 µg, 600 µg, 500 µg, 400 µg, 300 µg, 200 µg, 100 µg or 50 µg. For example, two oral dosage forms containing a composition provided herein, each containing a dose of a platelet number reducing agent of at or about 100 µg, can be administered four times a day in order to provide a dose of platelet number reducing agent of 800 µg per day. In some embodiments, up to at or about 1000 µg of a platelet number reducing agent can be administered per day. In some embodiments, a dose of platelet number reducing agent of 500 µg is administered twice a day. In some embodiments, a dose of platelet number reducing agent of 250 µg is administered four times a day. In some embodiments, a dose of platelet number reducing agent of 400 µg is administered twice a day. In some embodiments, a dose of platelet number reducing agent of 300 µg is administered twice a day. In some embodiments, a dose of platelet number reducing agent of 200 µg is administered twice a day. In some embodiments, a dose of platelet number reducing agent of 100 µg is administered twice a day.

L. Examples

The following examples, including experiments and results achieved, are provided for illustrative purposes only and are not to be construed as limiting the claimed subject matter.

1. Preparation of Exemplary Compositions

Instant release and controlled release compositions of anagrelide were made using the following procedures.

A. Manufacture of Beads Including a Substrate Layer

Solid cores coated with a substrate layer including the platelet reducing agent anagrelide hydrochloride monohydrate were prepared using non-pareil 20/25 sugar beads as the solid core to produce anagrelide loaded beads (substrate coated beads). The composition of the anagrelide loaded beads is shown in Table 1.

TABLE 1

Composition of anagrelide loaded beads.

| Component | Weight % |
|---|---|
| Solid Cores: Sugar Spheres NF (non-pareil 20/25 beads) | 97.31 |
| Substrate Layer: | |
| Anagrelide HCl Monohydrate | 0.16* |
| HPMC E5 USP or HPMC E5 Premium LV EP USP | 2.53 |
| Total = | 100 |

*Overage is included to account for coating efficiency

Substrate Layer:

The solution for the substrate layer was prepared by dissolving hydroxypropyl-methylcellulose (Methocel™ E5 USP or Methocel™ E5 LV Premium, which are commercially available from Dow Chemical, Midland, Mich.) in purified water. The purified water USP (691 grams) and hydroxypropylmethylcellulose (52 grams) were mixed until all solids were dissolved. The anagrelide (3.3168 grams) then was added and mixed until all solids are well dispersed. Sonication was used to aid in the dispersion. The mixture was homogenized at 5,000 rpm for at least 20 minutes and the solution was allowed to stand for not less than 1 hour to deaerate. After deaeration, the solution was mixed using a gentle agitation to keep undissolved solids suspended without pulling air into the solutions. This solution was used to apply the substrate layer to the solid core (non-pareil 20/25 beads).

Application of the Substrate Layer Using Fluid Bed Processing:

The coating unit was prepared for processing under controlled conditions for process using the following parameters: air volume (approximately 40 scfm), atom air pressure (14-18 psi), spray rate (2-9 g/min), and filter (20 psi), and preheated to a target inlet temperature of 60° C. and outlet temperature of 32° C. The coating unit then was charged with non-pareil 20/25 beads.

When the outlet temperature reached a temperature of 32° C., coating was initiated with the substrate layer solution for 10 minutes. The substrate layer was applied in three phases of 10 minutes each until the entire substrate layer was applied. The solution container was flushed with purified water USP.

The coated non-pareils were dried for 5 minutes at a target inlet temperature of 38° C. and the coated non-pareils were discharged into a polyethylene bag. The beads coated with the substrate layer including anagrelide were sieved through 18 mesh over 35 mesh (−18/+35 mesh).

B. Manufacture of Anagrelide IR Finished Beads

Instant release compositions of anagrelide were made using the following procedures.

Preparation of Immediate Release (IR) Coating Solution 210 grams of purified water USP was added to a mixing container and the mixer speed was set at sufficient energy to produce a strong vortex.

18.2 grams HPMC (Methocel™ E5 USP or Methocel™ E5 LV Premium, which are commercially available from Dow Chemical, Midland, Mich.) slowly was added to the vortex to minimize clumping and fish-eye formation, and the solution was mixed until all solids were dissolved.

Application of the IR Layer Using Fluid Bed Processing

The coating unit was prepared for processing under controlled conditions for process using the following parameters: air volume (approximately 40 scfm), and filter (25 psi), and preheated to a target inlet temperature of 71° C.

The coating unit was charged with anagrelide loaded beads (substrate layer coated beads, 894.6 grams, −18/+35 Mesh). The IR coating was applied at a target inlet temperature of 71° C., outlet temperature of 42° C., atmospheric air pressure (approximately 20 psi), and a spray rate of approximately 5 g/min until all of the IR coating solution was applied. The coated beads were dried at an inlet temperature of 32° C. and the materials were discharged into a polyethylene bag.

The IR coated anagrelide-containing beads were sieved over −18/+35 mesh after coating with the IR formulation. The composition of the IR bead formulation is shown in Table 2.

TABLE 2

Composition of anagrelide immediate release bead formulation.

| Component | Weight % |
|---|---|
| Anagrelide loaded beads | 98 |
| Seal Coat: | |
| HPMC E5 USP or HPMC E5 Premium LV EP USP | 2 |
| Total = | 100 |

C. Manufacture of Anagrelide CR Finished Beads

Controlled release compositions of anagrelide, including compositions with a seal coat, were made using the following procedures.

1. Composition 1—"Fast" Release, No Seal Coat

Preparation of Controlled Release Coating Solution 110.8 grams purified water USP was transferred through a filter or screen into a mixing tank. 3.7 grams hydroxypropyl methylcellulose (Methocel™ E5 USP or Methocel™ E5 LV Premium, which are commercially available from Dow Chemical, Midland, Mich.) was added slowly to the vortex with constant mixing to avoid clumping and fish-eye formation and the solution was mixed until all solids were dissolved. The mixing speed was adjusted as needed to avoid foam formation. The hydroxypropyl methylcellulose was used as a pore former.

The controlled release coating included ethyl cellulose. An aqueous dispersion of ethyl cellulose including plasticizers (Surelease E-7-19040) available from Colorcon, West Point, Pa.) was used. Surelease E-7-19040 contains at or about 25% solids, of which at or about 20% is ethyl cellulose. 33.6 grams Surelease E-7-19040 was added to the solution with constant mixing and the solution was mixed for not less than 30 minutes after addition of the Surelease was completed.

Application of the CR Layer Using Fluid Bed Processing

The coating unit was prepared for processing under controlled conditions for process using the following parameters: air volume (approximately 40 scfm), and filter (25 psi), and preheated to a target inlet temperature of 71° C.

The coating unit was charged with anagrelide loaded beads (substrate layer coated beads, 894.6 grams, −18/+35 Mesh).

The CR coating was applied at a target inlet temperature of 71° C., outlet temperature of 42° C., atmospheric air pressure (approximately 20 psi), and a spray rate of approximately 5 g/min until all of the IR solution was applied.

The coated beads were dried at an inlet temperature of 32° C. and the materials were discharged into a polyethylene bag. The CR coated anagrelide-containing beads were sieved over −18/+35 mesh after coating with the CR composition. The composition of controlled release composition 1, which is a "fast release" composition that does not include a seal coat, is shown in Table 3.

TABLE 3

Composition of controlled release bead composition 1 - fast release, no seal coat.

| Component | Weight % |
|---|---|
| Anagrelide loaded beads | 96 |
| Controlled Release Layer: | |
| HPMC E5 USP or HPMC E5 Premium LV EP USP | 0.4 |
| Surelease E-7-19040 | 3.6 |
| Total = | 100 |

2. Composition 2—"Fast" Release, with Seal Coat

A "fast" release controlled release composition of anagrelide that includes a seal coat was made using the procedures described above, using the composition as described in Table 4.

TABLE 4

Composition of controlled release bead composition 2 - fast release with seal coat.

| Component | Weight % |
|---|---|
| Solid Cores: Sugar Spheres NF (non-pareil 20/25 beads) | 91.55 |
| Substrate Layer: | |
| Anagrelide HCl Monohydrate | 0.151 |
| HPMC E5 USP or HPMC E5 Premium LV EP USP | 2.379 |
| Seal Coat: | |
| HPMC E5 USP or HPMC E5 Premium LV EP USP | 1.92 |
| Controlled Release Layer: | |
| HPMC E5 USP or HPMC E5 Premium LV EP USP | 0.4 |
| Surelease E-7-19040 | 3.6 |
| Total = | 100 |

3. Composition 3—"Slow" Release, No Seal Coat

A "slow" release controlled release composition of anagrelide was made using the procedures described above, using the composition as described in Table 5.

TABLE 5

Composition of controlled release bead composition 3 - slow release, no seal coat.

| Component | Weight % |
|---|---|
| Solid Cores: Sugar Spheres NF (non-pareil 20/25 beads) | 91.65 |
| Substrate Layer: | |
| Anagrelide HCl Monohydrate | 0.15 |
| HPMC E5 USP or HPMC E5 Premium LV EP USP | 2.4 |
| Controlled Release Layer: | |
| HPMC E5 USP or HPMC E5 Premium LV EP USP | 0.4 |
| Surelease E-7-19040 | 5.4 |
| Total = | 100 |

Preparation of Dosage Forms

The beads can be tabletted into tablets or dispensed into gelatin capsules or capsules made of material other than gelatin using standard equipment. The IR coated beads, the CR coated beads (with or without seal coat) or blends thereof were placed in a gelatin capsule, as shown in Scheme II above. The composition of the capsules for a representative batch that includes CR coated beads without a seal coat is shown in Table 6.

TABLE 6

Qualitative and quantitative composition of CR and IR/CR anagrelide capsules.

| | | Amount per Batch (mg) | | | | |
|---|---|---|---|---|---|---|
| Item | Component | 100 μg CR | 300 μg CR | 100 μg IR/CR | 300 μg IR/CR | Function |
| Medicinal Product | Anagrelide HCl monohydrate | 0.1213* | 0.3639* | 0.1213* | 0.3639* | Active ingredient |
| Excipients (Medicinal | Sugar Spheres NF (Non-pareil 20/25 beads) | 97.3 | 291.9 | 97.3 | 291.9 | Pellets |

TABLE 6-continued

Qualitative and quantitative composition of CR and IR/CR anagrelide capsules.

| | | Amount per Batch (mg) | | | | |
|---|---|---|---|---|---|---|
| Item | Component | 100 μg CR | 300 μg CR | 100 μg IR/CR | 300 μg IR/CR | Function |
| Product) | HPMC E5 USP cr HPMC E5 Premium LV EP USP | 2.5 | 7.5 | 2.5 | 7.5 | Binding agent |
| IR Beads | HPMC E5 USP cr HPMC E5 Premium LV EP USP | — | — | 1.03 | 3.09 | Seal coat |
| CR Beads | Surelease E-7-19040 (Aquecous ethylcelullose dispersion) | 0.4 | 1.2 | 0.2 | 0.6 | Polymer coating |
| | HPMC E5 USP cr HPMC E5 Premium LV EP USP | 3.6 | 10.8 | 1.8 | 5.4 | Binding agent/Pore former |
| Coated Bead Weight | | 103.9** | 311.7** | 102.9** | 308.7 | — |
| Capsule | Empty capsule shell | 94.1 | 94.0 | 94.1 | 94.0 | — |
| Total Capsule Weight | (Size 0, Swedish orange) (adjusted for actual capsule shell weight) | 198.0 | 405.7 | 197.0 | 402.7 | — |

*Equivalent to 100 μg or 300 μg of Anagrelide free base.
**Final weight used adjusted for assay.

All excipients used in the production of the anagrelide compositions were compendial grade (EP/USP/NF).

As discussed below, the dosage form illustrated in Table 6 provided an advantageous human pharmacokinetic profile, however the capsules showed evidence of instability, characterized as a loss in active pharmaceutical ingredient (API) content without correlating increases in degradants. As indicated in TABLE 6, the controlled release layer was produced by application of Surelease® E7 1904, an aqueous dispersion of ethylcellulose.

Pre-formulation studies utilizing binary mixtures of the API with various excipients (ethylcellulose, Eudragit® RS and RL, Aquacoat® ECD30, ammonium oleate and Surelease® E7 1904) were conducted using a high sensitivity calorimeter in isothermal mode. Excipients were compared on their own and as mixtures with/without saturated sodium chloride solution present. In this technique, the heat changes in samples (API alone, excipient alone, API:excipient (1:1 ratio)) were monitored over 24 hours at a temperature range of 30-80° C. The API and ethylcellulose showed evidence of compatibility. The data for the API and Aquacoat were not conclusive as to compatibility. The API and Eudragit (RS and RL), Surelease and ammonium oleate all showed evidence of incompatibility. Improved dosage forms were formed by employing ethylcellulose in the excipient system and a mode of application including organic (ethanol) spray application due to the insolubility of ethylcellulose in water.

Table 7 presents the components and function of an illustrative anagrelide CR utilizing an organic formulation. The system is applied as a fluid bed spray coating in Wurster mode on non-pareil beads. A layer of API is applied in the presence of HPMC as a binder. Subsequently, a HPMC seal coat 5% (w/w) is applied to the drug-loaded beads followed by the controlled release layer including ethylcellulose, HPMC, triethylcitrate (TEC), and talc to a target weight gain of 3.5% (w/w).

TABLE 7

Components of Anagrelide 500 μg CR Capsules
2 Kg Batch (Formula F-2887-044)

| Item | Ingredients | % w/w | Quantity/Unit (mg/capsule) | Total Theoretical Quantity Required (g) | Function |
|---|---|---|---|---|---|
| Active Ingredient | Anagrelide HCl monohydrate (micronized) | 0.1186 | 0.606* | | Drug Substance |
| Excipients | Sugar Spheres (Non-Pareil 20/25 beads), NF | 89.4192 | 456.925 | | Substrate |
| | Hypromellose (HPMC E5 Premium LV), EP/USP | 7.4344 | 37.989 | | Binding agent |
| | Ethylcellulose (Ethocel Standard 10 Premium), NF/EP | 1.5509 | 7.925 | | Controlled Release agent |

TABLE 7-continued

Components of Anagrelide 500 µg CR Capsules
2 Kg Batch (Formula F-2887-044)

| Item | Ingredients | % w/w | Quantity/Unit (mg/capsule) | Total Theoretical Quantity Required (g) | Function |
|---|---|---|---|---|---|
| | Triethyl Citrate (TEC), NF/EP | 0.5908 | 3.019 | | Plasticizer |
| | Talc, EP/USP | 0.8881 | 4.528 | | Detackifier |
| | TOTAL | 100.000 | 510.992 | 1,022.0 | |
| Capsule | Empty capsule shell (Size 00 White opaque/white opaque) | | | 2,000 capsules | Container |
| | Purified Water** | | | | Solvent |
| | Ethanol** | | | | Solvent |

*Equivalent to 0.500 mg of anagrelide free base
**Evaporates during processing

2. In Vitro Dissolution Studies

In Vitro (formulation similar to the 500 µg of Table 7, adjusted to reflect a 200 µg dosage form) were performed in simulated gastric fluid using standard USP methodology and compared with the dissolution of the control commercial immediate release anagrelide 0.5 mg IR capsules (XAGRID®, Shire Pharmaceutical Contracts Limited, Hampshire, UK). The results are shown in Table 8a.

TABLE 8a

In vitro dissolution results for anagrelide capsules and control (XAGRID® IR capsules).

| | Results | | | | | | |
|---|---|---|---|---|---|---|---|
| In Vitro Dissolution Rate (mean) | Xagrid 0.5 mg IR Capsules | 100 µg CR Capsules Campaign 1 | 300 µg CR Capsules Campaign 1 | 100 µg IR/CR Capsules Campaign 1 | 300 µg IR/CR Capsules Campaign 1 | 100 µg CR Capsules Campaign 2 | 100 µg IR/CR Capsules Campaign 2 |
| 30 minutes | 92% | — | — | — | — | | |
| 1 hour | 56% | 51% | 51% | 74% | 71% | 39% | 67% |
| 2 hour | 95% | 70% | 69% | 84% | 80% | 60% | 80% |
| 3 hour | 94% | 78% | 77% | 88% | 84% | 76% | 87% |
| 4 hour | 94% | 83% | 81% | 91% | 86% | 84% | 91% |
| 5 hour | 94% | 86% | 83% | 92% | 88% | 89% | 95% |
| 6 hour | 93% | 88% | 85% | 93% | 88% | 92% | 97% |

In vitro dissolution profiles, stability and moisture content for the anagrelide CR formulations with seal coat are provided in tables 8b, 8c and 8d and FIGS. 1-4.

Dissolution of the anagrelide CR product made under aqueous conditions was investigated at three conditions (FIG. 1): Simulated Gastric Fluid (SGF), 0.3% sodium lauryl sulfate (SLS) in sodium acetate (pH 4.5), and 0.1% Tween 80 in potassium phosphate (pH 6.8). The dissolution profiles suggest that dissolution is possible for all conditions tested with the aqueous formulated materials, however lower pH systems appear to be favored in this experiment.

Figure 2:
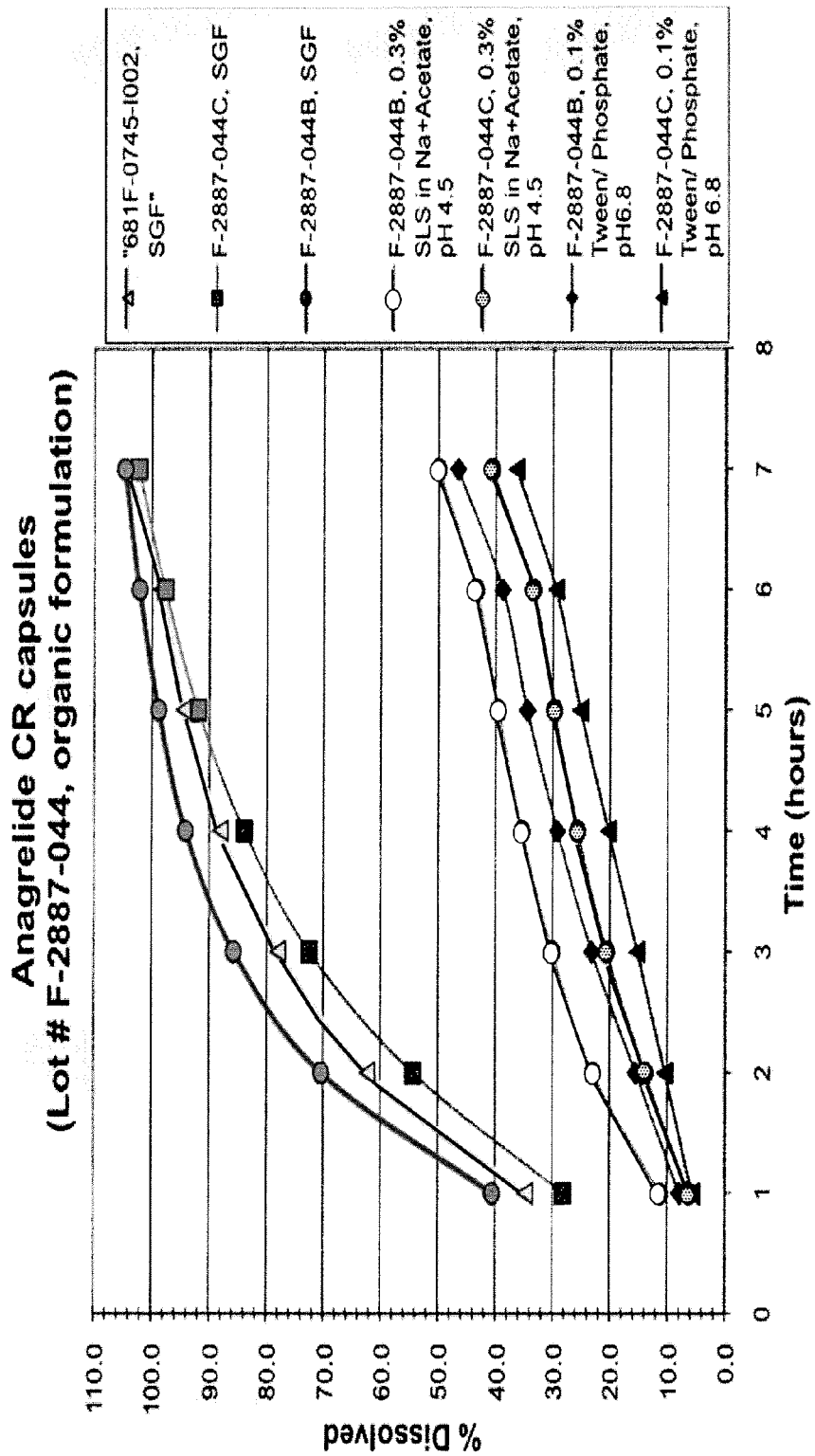
FIG. 2 is a graph showing the dissolution profiles of different anagrelide CR capsules (F-2887-044B and F-2887-044C, organic formulations) at three pH conditions. The 7 hour time is considered infinity (paddles at 250 rpm for 1 hour).

In contrast, dissolution studies with formulations using the organic coating system suggest that there may be a difference in the ability of anagrelide to dissolve compared to the aqueous coating system (FIG. 2). At the higher two pH conditions, the organic coated materials dissolve more slowly than the aqueous coated materials. Without wishing to be bound by any theory, it is contemplated that the Surelease® aqueous dispersion system may provide localized solubility support for the API in the dissolution system and thus, may distort the dissolution findings at higher pH conditions.

Figure 3:
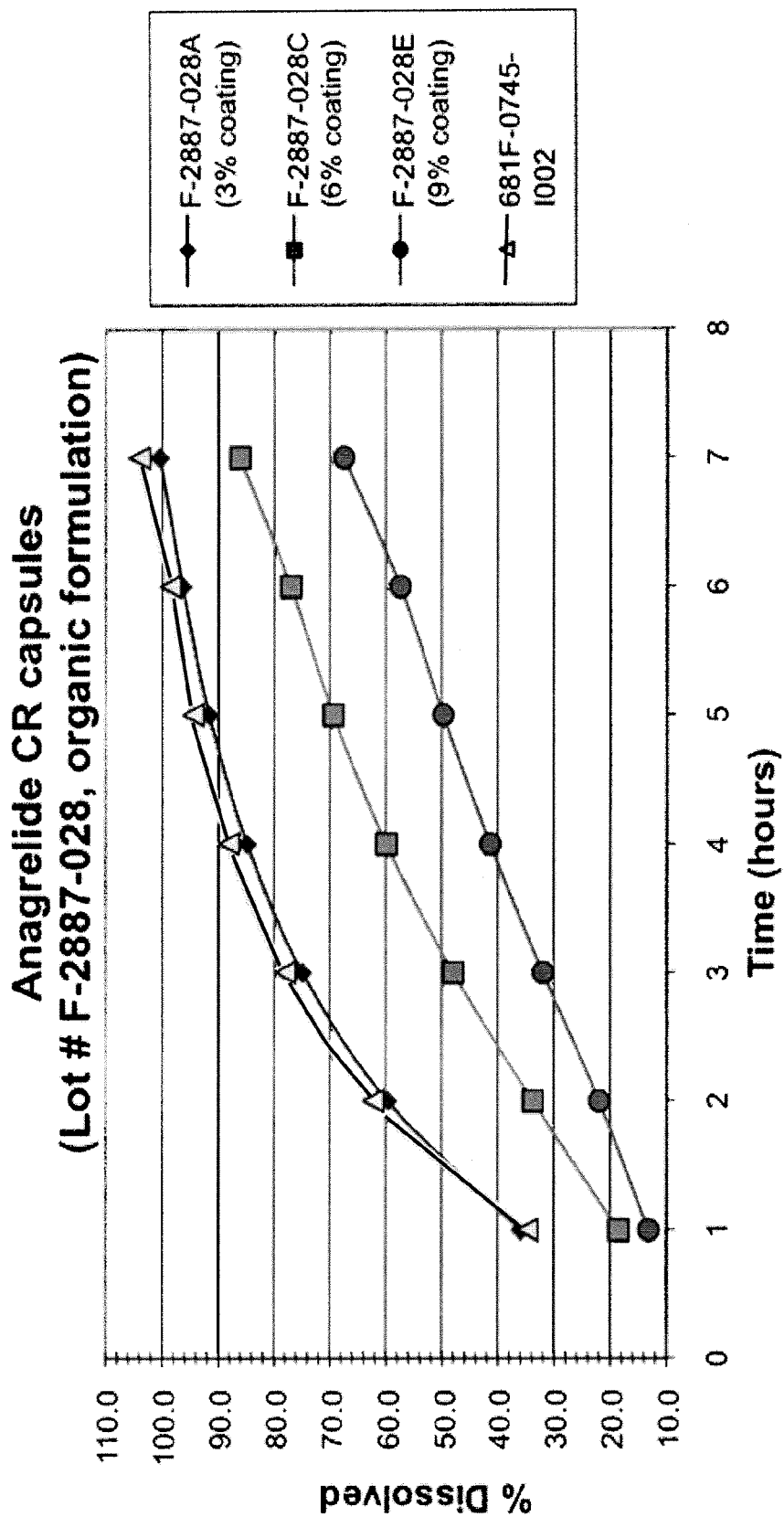
FIG. 3 is a graph showing the dissolution profiles of different anagrelide CR capsules (F-2887-028, organic formulation) in simulated gastric fluid (SGF). The 7 hour time is considered infinity (paddles at 250 rpm for 1 hour).

For the organic formulation, multiple prototypes were produced, utilizing hydroxypropylmethylcellulose (HPMC) as a binder/pore former at different ratios. A ratio of 3:1 ethylcellulose:HPMC at a weight gain of 3% (w/w) provided dissolution characteristics comparable to the dissolution characteristics obtained for the aqueous formulation (FIG. 3).

Accelerated stability samples for the organic formulation demonstrated some degradation (data not shown), which was determined to be caused by the plasticizer, TEC, in the coating formula. The level of degradation was far lower than that seen in the aqueous formulation. An investigation was conducted to determine if an alternate plasticizer (triacetin and dibutyl sebacate) would provide an effective alternate to TEC while eliminating the interaction with the API. The isothermal calorimetry data did not suggest a viable alternate to TEC. A protective barrier of 5% (w/w) HPMC was added to the coating system between the API and controlled release layers (a seal coat).

Figure 4:
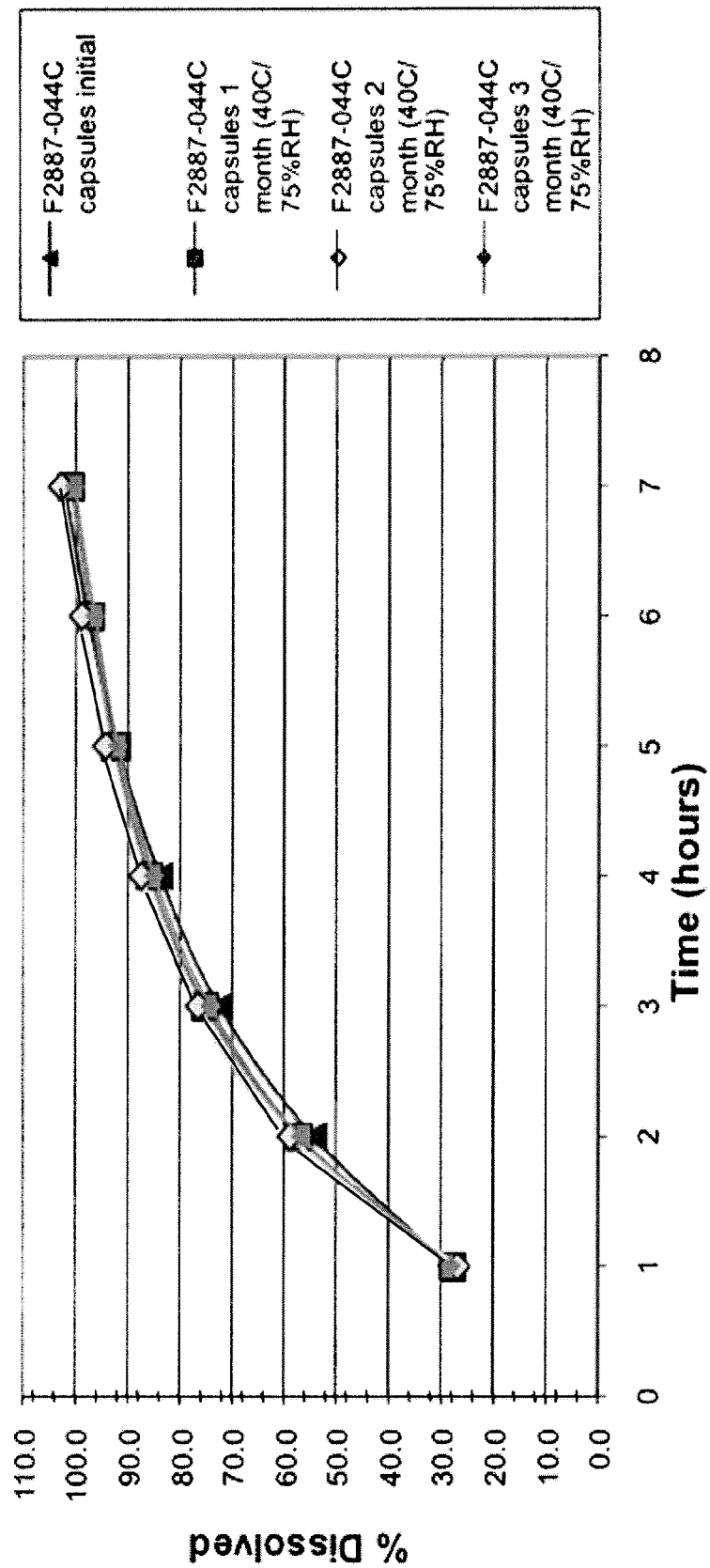
FIG. 4 is a graph showing the dissolution profiles of different anagrelide CR capsules (F-2887-044C, organic formulation) in SGF after accelerated storage stability testing. The 7 hour time is considered infinity (paddles at 250 rpm for 1 hour).
Figure 5:
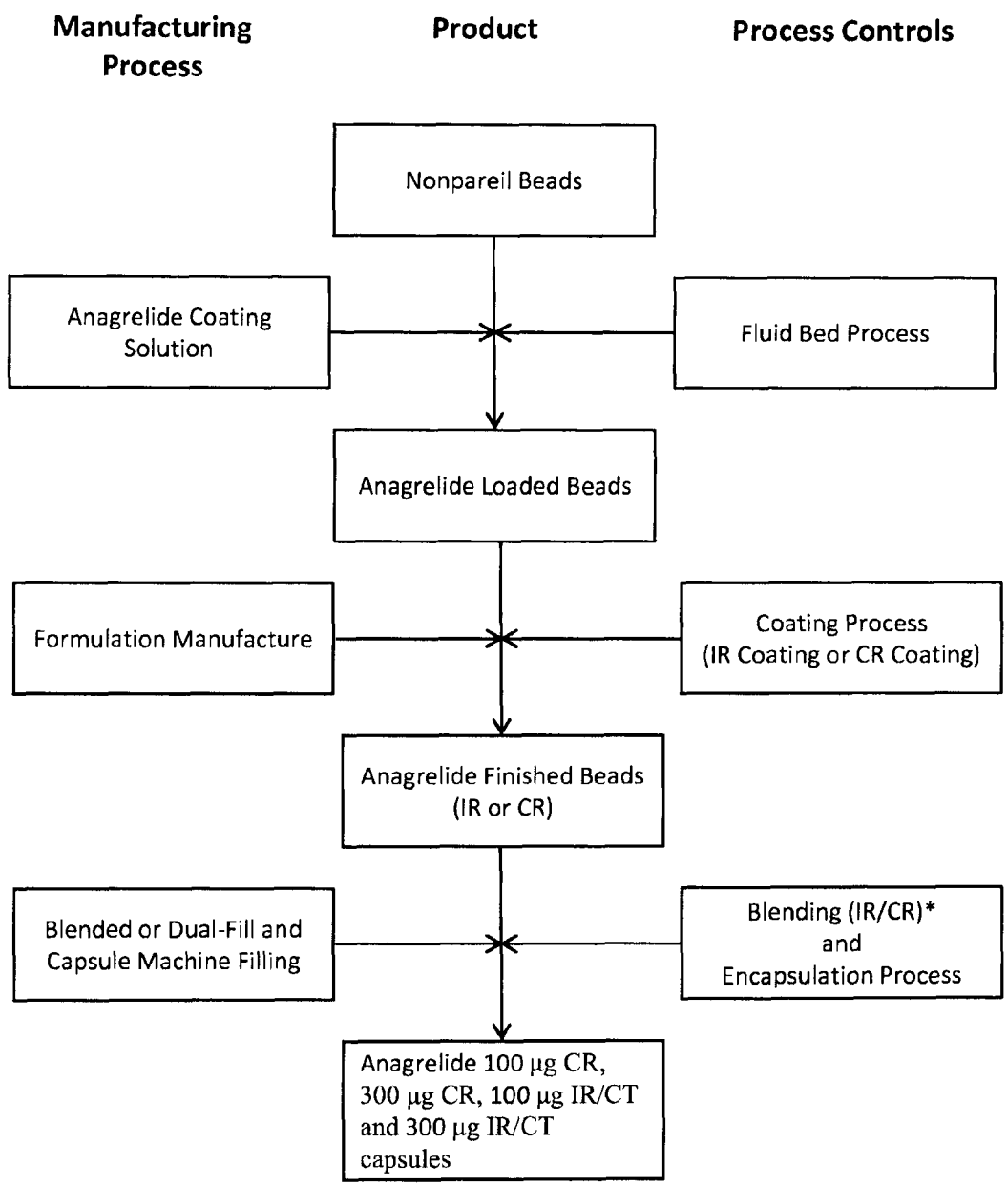
FIG. 5 is a flow chart showing an exemplary production scheme for manufacturing capsules containing anagrelide.

The three month accelerated stability of the organic formula is presented below (Table 8b, FIG. 4). Anagrelide CR capsules are stable at accelerated conditions for at least 3 months. Thus, the stability results for the organic formulation indicated stability for at least 6 months shelf life at room temperature storage conditions.

TABLE 8b

Stability of Anagrelide CR 200 µg Capsules by HPLC Analysis

| | Anagrelide | | | Individual impurities (RRT) | | |
|---|---|---|---|---|---|---|
| Condition | Assay (% label, as free base) | Moisture Content (% w/w) | Total Impurities* (% area) | 0.65** (unidentified) | 0.90** (Acid Impurity) | 1.50** (Methyl Impurity) |
| Initial | 108.7 | 1.3 | 1.01 | 0.10 | 0.82 | 0.00 |
| 1 month @ 40 C/75% RH | 103.9 | 2.2 | 2.23 | 0.63 | 1.15 | 0.09 |
| 2 months @ 40 C/75% RH | 104.6 | 2.0 | 1.99 | 0.72 | 0.94 | 0.15 |
| 3 months @ 40 C/75% RH | 101.2 | 1.2 | 2.65 | 0.58 | 1.17 | 0.23 |

RRT: relative retention time to API
*total of all impurities not corresponding to placebo RRT peaks
**gradient altered at 2 months to improve peak resolution, RRTs were 0.82, 0.95 and 1.24, respectively A stability program testing Agrylin® was conducted to compare anagrelide CR to the reference product. Tables 8c and 8d present assay and purity data for anagrelide API and Agrylin® under accelerated stability conditions. The data suggest that the major impurities found in anagrelide CR (Table 8b) are common to the reference product, Agrylin®. The data also suggest that a slow conversion to the acid form may occur in API under accelerated conditions.

3. In Vivo Baboon Studies

An in vivo animal study was performed to demonstrate that CR compositions of anagrelide as provided herein reduce the $C_{max}$ while maintaining the AUC. A non-clinical, single dose crossover, open label study of the pharmacokinetics of a single dose of five different formulations of anagrelide was conducted in 6 healthy, fasted *Papio anubis* baboons. The formulations included the marketed commercial anagrelide formulation (IR-Shire) plus compositions in the form of anagrelide-loaded non-pareil beads coated with various polymers used to control release. The trial formulations were immediate release bead (IR bead), controlled release—fast (CR-Fast), controlled release—slow (CR-Slow) and enteric coated (EC). Each baboon received a single 0.5 mg dose of each formulation using a crossover design, with at least seven days between doses. The anagrelide was administered as follows: 0.5 mg of each formulation was suspended in water and administered via oral gavage to each baboon. A three day washout was used between treatments.

The following formulations were used:

AGRYLIN®: (IR-Shire), immediate release product (0.5 mg—capsule opened and dosed via oral gavage);

Enteric Coated Anagrelide Bead Formulation (EC): Substrate layer (including anagrelide)-coated non-pareil beads were coated with EUDRAGIT® polymer for release in pH 5.5. (0.5 mg of beads dosed via oral gavage);

Controlled Release (Fast) Anagrelide Bead Formulation (CR-Fast): Substrate layer (including anagrelide)-coated non-pareil beads were coated with HPMC/Ethylcellulose for release over 4-6 hours (0.5 mg of beads dosed via oral gavage);

Controlled Release (Slow) Anagrelide Bead Formulation (CR-Slow): Substrate layer (including anagrelide)-coated non-pareil beads were coated with HPMC/ethylcellulose for release over 8-12 hours (0.5 mg of beads dosed via oral gavage); and Immediate Release Anagrelide Bead Formulation (IR Beads): Substrate layer (including anagrelide)-coated non-pareil beads that release anagrelide in 15 minutes (0.5 mg of beads dosed vial oral gavage).

Animals:

All the baboons (*papio anubis*) in the study were healthy juvenile male baboons observed to be disease free ranging in weight between 8.5 kg to 11.5 kg and in the care of the department of animal resources. The animals were on a standard diet consisting of monkey chow, fruits and vegetables between each weekly study period. Two to three animals were dosed per day, with 6 animals per week total. A three day washout was used between treatments. There were 5 treatment groups, and each animal was crossed over to each treatment group.

Dosing:

The baboons were fasted overnight. In the morning they were sedated with ketamine (1-2 mg/kg) and restrained upright in a sitting position. Following a baseline blood sample anagrelide was administered by gavage and washed down with approximately 15 mL of water and a timer started. The drug dose was kept dry in a tube until it was delivered to the gavage tube and then washed down the tube with 7-8 mL of water followed by another 7-8 mL of water. The gavage tube was inspected for any residual beads upon removal and was clean. The animals remained restrained with minimal ketamine for 4 hours for the collection of the timed blood samples and then returned to their cages and fed fruit. The remaining blood samples were collected from the baboons after light sedation with ketamine (1-2 mg/kg). Each drug formulation was given only once a week.

Adverse Events:

There were no adverse effects noted from the gavage procedure. One animal, Animal #6, had multiple bowel movements with mounding stools 1 hour following dosing with the enteric beads (EC), fast release bead formulations (CR-Fast) and immediate release beads (IR bead). This animal also vomited 2 hours post dosing of the immediate release beads (IR bead). It is assumed that animal #2 vomited post dosing of the enteric beads (EC) based on the low circulating concentration of drug in this animal. No other symptoms in any of the other animals were noted. CBC's were monitored once a week and remained in the normal range throughout the study period.

Specimen Collection and Processing:

Blood was drawn on Day 1 at predose (0) and 0.5, 1, 2, 3, 4, 6, 8, 12, and 24 hours after dosing. Samples were collected in syringes and transferred to appropriately labeled, evacuated blood collection tubes, containing K2-EDTA as the anticoagulant. Immediately after collection, the filled blood collection tubes were gently inverted several times to insure that the anticoagulant is thoroughly mixed with the blood. Within 30 minutes after collection the blood samples were centrifuged at 4° C. for 10 minutes at 3000 RPM for processing blood to plasma. Each plasma sample was harvested within 30 minutes from the centrifuged samples. Each sample was split into equally sized split samples, into labeled polypropylene screw top transfer tubes. The harvested plasma samples were transferred without delay to a freezer, where they were frozen in the upright position. Samples were maintained at −80° C. until shipping.

Plasma samples were analyzed for anagrelide and 3-OH anagrelide concentrations by LCMS/MS. An eight point calibration curve of anagrelide and a separate eight point calibration curve for 3-OH anagrelide ranging from 50-5000 pg/mL was prepared by spiking the drug-free human plasma containing K2-EDTA with an appropriate amount of anagrelide and 3-OH anagrelide. The quality control samples spiked at three concentrations (Low, Mid, High) were prepared in a similar manner. A second set of quality control samples in drug free baboon plasma were prepared to ensure that the extraction and methodology developed for the human assay would not encounter any endogenous interference from the baboon plasma.

Extraction Procedure:

A 400 μL aliquot of plasma was placed in a tube using an automatic pipet, followed by the addition of 2 mL buffer and followed by 100 μL of internal standard (15 ng/mL bromazepam). To this mixture, 0.1 mL of ascorbic acid 0.85M was added. The resultant volume was loaded onto SPE cartridges (Oasis HLB 60 mg, 3 cc). The cartridges were centrifuged, washed with Milli-Q type water, and washing solution (methanol/Milli-Q Type water (60/40). After a subsequent centrifugation, the column was eluted with methanol. The eluent was evaporated to dryness using nitrogen at 50° C. on a Turbo Vap evaporator. The dry residues were reconstituted in 200 μL of reconstitution solution (methanol/Milli Q type water (50/50) containing ammonium formate 2 mM).

A mass spectra was obtained by using an API 5000 (MDS Sciex, Toronto Canada) equipped with Heated Nebulizer. The data acquisition was ascertained by Analyst 1.4.1 (or higher, MDS Sciex, Toronto Canada). Positive mode was used for the analysis. The mass ion pair measured was 256.10 ⇔ 199.00 for anagrelide, 272.04 ⇔ 199.04 for 3-OH anagrelide and 316.40 ⇔ 182.10 for bromazepam. The mass spectrometer conditions were set as follows:

| | |
|---|---|
| Auxiliary gas pressure (GS2): 50 psi | Interface heater (Ihe): 1 |
| Nebulizer gas pressure (GS1): 50 psi | CAD gas: 10 |
| Curtain gas pressure: 25 psi | Ionization mode: Positive |
| Heated nebulizer temperature: 500° C. | Needle Corona (NC): 3.00 |

The following pharmacokinetic parameters were estimated from measured plasma anagrelide and 3-OH anagrelide concentrations for each subject and each treatment:

$C_{max}$=measured maximal concentration $T_{max}$=time to reach maximum concentration (AUC$_{all}$)=area under the concentration-time curve calculated by the linear trapezoidal rule from time 0 to the time of last sample with a quantifiable concentration ($C_t$)

AUC$_{0-\infty}$=area under the concentration time curve from time 0 extrapolated to infinity $T_{1/2}$=terminal half-life, calculated as $Ln(2)/K_{el}$ 3. Results Estimates were made for the ratios of the relevant pharmacokinetic parameters to the immediate release reference product (Shire), as shown in Table 9.

TABLE 9

Ratio of pharmacokinetic parameters to IR-Shire material as a reference.

| | IR Beads | Enteric Coated | CR-Slow | CR-Fast |
|---|---|---|---|---|
| Tmax | 1.50 (2.23) | 4.80 (4.38) | 4.39 (3.88) | 3.28 (1.53) |
| Cmax | 1.12 (0.78) | 1.01 (0.69) | 0.42 (0.25) | 0.46 (0.21) |
| AUCall | 1.00 (0.24) | 1.02 (0.45) | 0.48 (0.14) | 0.58 (0.16) |
| Half-Life | 1.60 (0.56) | 1.26 (0.90) | 1.91 (1.22) | 1.99 (1.46) |

Data are presented as mean (sd)

3.1 Immediate Release (IR-Shire) Formulation

Individual pharmacokinetic parameters and mean concentration data are presented in Tables 10 and 11.

TABLE 10

Individual and average pharmacokinetic parameters of anagrelide for baboons receiving 0.5 mg immediate release anagrelide (IR-Shire).

| Animal | Tmax (hr) | Cmax (ng/mL) | AUCall (hr * ng/mL) | HL_Lambda_z (hr) |
|---|---|---|---|---|
| 1 | 1 | 8.29 | 31.43 | 4.03 |
| 2 | 4 | 5.81 | 30.89 | 1.55 |
| 3 | 1 | 4.14 | 26.38 | 1.44 |
| 4 | 3 | 4.37 | 25.22 | 2.04 |
| 5 | 1 | 6.69 | 23.21 | 1.88 |
| 6 | 3 | 3.09 | 25.9 | 3.59 |
| Mean | 2.167 | 5.399 | 27.171 | 2.421 |
| SD | 1.329 | 1.905 | 3.278 | 1.106 |
| CV % | 61.3 | 35.3 | 12.1 | 45.7 |

TABLE 11

Individual and average pharmacokinetic parameters of 3-OH anagrelide for baboons receiving 0.5 mg immediate release anagrelide (IR-Shire).

| Animal | Tmax (hr) | Cmax (ng/mL) | AUCall (hr * ng/mL) | HL_Lambda_z (hr) |
|---|---|---|---|---|
| 1 | 0.5 | 2.14 | 8.77 | 3.96 |
| 2 | 2 | 0.68 | 4.81 | 2.34 |
| 3 | 3 | 0.6 | 3.38 | 2.51 |
| 4 | 3 | 1.11 | 6.9 | 5.4 |
| 5 | 1 | 1.31 | 5.14 | 3.24 |
| 6 | 3 | 0.48 | 3.64 | 4.28 |
| Mean | 2.083 | 1.052 | 5.439 | 3.621 |
| SD | 1.114 | 0.619 | 2.059 | 1.162 |
| CV % | 53.5 | 58.9 | 37.9 | 32.1 |

3.2 Enteric Coated Formulation

Formulations that included an enteric coating on the beads were prepared. Individual pharmacokinetic parameters and mean concentration data are presented in Tables 12-14. It is assumed that Animal #2 vomited post dosing of the enteric beads (EC) based on the lack of measurable drug for the pharmacokinetic data.

TABLE 12

Individual and average pharmacokinetic parameters of anagrelide for baboons receiving 0.5 mg enteric coated anagrelide (EC).

| Animal | Tmax (hr) | Cmax (ng/mL) | AUCall (hr * ng/mL) | HL_Lambda_z (hr) |
|---|---|---|---|---|
| 1 | 6 | 3.24 | 21.08 | 7.65 |
| 2 | 4 | 0.16 | 0.75 | 3.03 |
| 3 | 6 | 7.09 | 28.89 | 3.97 |
| 4 | 6 | 8.53 | 37.7 | 2.78 |
| 5 | 6 | 2.35 | 19.09 | 3.97 |
| 6 | 6 | 4.37 | 30.63 | 3.5 |
| Mean | 5.667 | 4.288 | 23.025 | 4.15 |
| SD | 0.816 | 3.089 | 12.828 | 1.784 |
| CV % | 14.4 | 72 | 55.7 | 43 |

TABLE 13

Individual and average pharmacokinetic parameters of 3-OH anagrelide for baboons receiving 0.5 mg enteric coated anagrelide (EC).

| Animal | Tmax (hr) | Cmax (ng/mL) | AUCall (hr * ng/mL) | HL_Lambda_z (hr) |
|---|---|---|---|---|
| 1 | 6 | 0.62 | 6.1 | 11.03 |
| 2 | Missing | Missing | Missing | Missing |
| 3 | 6 | 0.8 | 3.54 | 2.65 |
| 4 | 6 | 2.08 | 12.04 | 2.12 |
| 5 | 6 | 0.4 | 2.98 | 3.44 |
| 6 | 6 | 0.59 | 3.69 | 4.38 |
| Mean | 6 | 0.898 | 5.67 | 4.723 |
| SD | 0 | 0.675 | 3.754 | 3.629 |
| CV % | 0 | 75.2 | 66.2 | 76.8 |

TABLE 14

Mean plasma concentration of anagrelide and 3-OH anagrelide in baboons receiving 0.5 mg enteric coated anagrelide (EC).

| | Enteric Coated | | | | | |
|---|---|---|---|---|---|---|
| | Anagrelide | | | 3-OH Anagrelide | | |
| Time (hr) | Mean (ng/mL) | SD (ng/mL) | CV % | Mean (ng/mL) | SD (ng/mL) | CV % |
| 0 | NA | NC | NC | NA | NC | NC |
| 0.5 | 0.52 | NC | NC | 0.11 | NC | NC |
| 1 | 0.62 | 0.96 | 154.42 | 0.32 | NC | NC |
| 1.5 | 0.76 | 1.14 | 151.17 | 0.29 | NC | NC |
| 2 | 0.63 | 1.08 | 130.01 | 0.3 | NC | NC |
| 3 | 0.81 | 0.8 | 98.65 | 0.19 | 0.09 | 45.36 |
| 4 | 0.78 | 0.67 | 86.01 | 0.17 | 0.09 | 51.26 |
| 6 | 4.29 | 3.09 | 72.2 | 0.9 | 0.68 | 75.23 |
| 8 | 2.05 | 1.53 | 74.56 | 0.53 | 0.32 | 60.13 |
| 12 | 0.71 | 0.35 | 49.46 | 0.21 | 0.07 | 34.24 |
| 24 | 0.17 | 0.18 | 105.49 | 0.19 | NC | NC |

3.3 Controlled Release Fast Composition (CR-Fast)

Controlled release compositions of anagrelide were prepared. One composition included anagrelide loaded non-pareil beads that were overcoated with an HPMC/ethyl cellulose layer for release over 4 to 6 hours (designated as CR-Fast). Individual pharmacokinetic parameters and mean concentration data are presented in Tables 15-17.

3.4 Controlled Release Slow Composition (CR-Slow)

One controlled release composition of anagrelide was prepared by overcoating anagrelide loaded non-pareil beads with an HPMC/ethyl cellulose layer for release over 8 to 12 hours (designated as CR-Slow). Individual pharmacokinetic parameters and mean concentration data are presented in Tables 18-20.

TABLE 15

Individual and average pharmacokinetic parameters of anagrelide for baboons receiving 0.5 mg controlled release (fast) anagrelide (CR-Fast).

| Animal | Tmax (hr) | Cmax (ng/mL) | AUCall (hr * ng/mL) | HL_Lambda_z (hr) |
|---|---|---|---|---|
| 1 | 2 | 2.81 | 17.79 | 16.33 |
| 2 | 6 | 1.37 | 12.49 | 4.23 |
| 3 | 6 | 2.07 | 19.44 | 4.17 |
| 4 | 6 | 4.29 | 26.26 | 3.06 |
| 5 | 6 | 2.33 | 17.81 | 6.46 |
| 6 | 6 | 3.08 | 18.9 | 2.07 |
| Mean | 5.333 | 2.659 | 18.782 | 6.054 |
| SD | 1.633 | 0.996 | 4.424 | 5.242 |
| CV % | 30.6 | 37.5 | 23.6 | 86.6 |

TABLE 16

Individual and average pharmacokinetic parameters of 3-OH anagrelide for baboons receiving 0.5 mg controlled release (fast) anagrelide (CR-Fast).

| Animal | Tmax (hr) | Cmax (ng/mL) | AUCall (hr * ng/mL) | HL_Lambda_z (hr) |
|---|---|---|---|---|
| 1 | 2 | 0.52 | 4.17 | 15.5 |
| 2 | 6 | 0.21 | 1.54 | 4.01 |
| 3 | 8 | 0.23 | 2.09 | Missing |
| 4 | 6 | 0.8 | 4.95 | 2.6 |
| 5 | 6 | 0.45 | 3.52 | 9.74 |
| 6 | 6 | 0.35 | 2.51 | 3.49 |
| Mean | 5.667 | 0.427 | 3.129 | 7.068 |
| SD | 1.966 | 0.22 | 1.307 | 5.485 |
| CV % | 34.7 | 51.4 | 41.8 | 77.6 |

TABLE 18

Individual and average pharmacokinetic parameters of anagrelide for baboons receiving 0.5 mg controlled release (slow) anagrelide (CR-Slow).

| Animal | Tmax (hr) | Cmax (ng/mL) | AUCall (hr * ng/mL) | HL_Lambda_z (hr) |
|---|---|---|---|---|
| 1 | 6 | 1.44 | 13.85 | 5.74 |
| 2 | 8 | 1.57 | 9.11 | Missing |
| 3 | 4 | 2.7 | 14.29 | 3.79 |
| 4 | 6 | 4.4 | 24.68 | 3.59 |
| 5 | 3 | 1.35 | 12.02 | 6.98 |
| 6 | 8 | 1.94 | 24.2 | 3.7 |
| Mean | 5.833 | 2.23 | 16.355 | 4.758 |
| SD | 2.041 | 1.17 | 6.522 | 1.527 |
| CV % | 35 | 52.4 | 39.9 | 32.1 |

TABLE 19

Individual and average pharmacokinetic parameters of 3-OH anagrelide for baboons receiving 0.5 mg controlled release (slow) anagrelide (CR-Slow).

| Animal | Tmax (hr) | Cmax (ng/mL) | AUCall (hr * ng/mL) | HL_Lambda_z (hr) |
|---|---|---|---|---|
| 1 | 6 | 0.62 | 6.1 | 11.03 |
| 2 | Missing | Missing | Missing | Missing |
| 3 | 6 | 0.8 | 3.54 | 2.65 |
| 4 | 6 | 2.08 | 12.04 | 2.12 |
| 5 | 6 | 0.4 | 2.98 | 3.44 |
| 6 | 6 | 0.59 | 3.69 | 4.38 |
| Mean | 6 | 0.898 | 5.67 | 4.723 |
| SD | 0 | 0.675 | 3.754 | 3.629 |
| CV % | 0 | 75.2 | 66.2 | 76.8 |

TABLE 17

Mean plasma concentration of anagrelide and 3-OH anagrelide in baboons receiving 0.5 mg controlled release (fast) anagrelide (CR-Fast).

| | CR-Fast | | | | | |
|---|---|---|---|---|---|---|
| | Anagrelide | | | 3-OH Anagrelide | | |
| Time (hr) | Mean (ng/mL) | SD (ng/mL) | CV % | Mean (ng/mL) | SD (ng/mL) | CV % |
| 0 | NA | NC | NC | NA | NC | NC |
| 0.5 | 0.21 | 0.11 | 51.66 | 0.06 | 0 | 3.57 |
| 1 | 0.88 | 0.53 | 59.73 | 0.16 | 0.11 | 71.51 |
| 1.5 | 1.19 | 0.73 | 61.42 | 0.19 | 0.15 | 81.51 |
| 2 | 1.4 | 0.81 | 58.37 | 0.23 | 0.17 | 71.83 |
| 3 | 1.38 | 0.56 | 40.4 | 0.23 | 0.13 | 56.95 |
| 4 | 1.48 | 0.63 | 42.71 | 0.24 | 0.14 | 58.32 |
| 6 | 2.33 | 1.24 | 53.11 | 0.37 | 0.23 | 62.78 |
| 8 | 1.35 | 0.44 | 32.77 | 0.24 | 0.11 | 45.04 |
| 12 | 0.48 | 0.1 | 21.62 | 0.13 | 0.03 | 24.89 |
| 24 | 0.17 | 0.13 | 75.92 | 0.08 | 0.01 | 14.37 |

TABLE 20

Mean plasma concentration of anagrelide and 3-OH anagrelide in baboons receiving 0.5 mg controlled release (slow) anagrelide (CR-Slow).

CR-Slow

| | Anagrelide | | | 3-OH Anagrelide | | |
|---|---|---|---|---|---|---|
| Time (hr) | Mean (ng/mL) | SD (ng/mL) | CV % | Mean (nglmL) | SD (ng/mL) | CV % |
| 0 | NA | NC | NC | NA | NC | NC |
| 0.5 | 0.15 | 0.09 | 62.1 | NA | NC | NC |
| 1 | 0.32 | 0.26 | 81.82 | 0.07 | 0.01 | 17.09 |
| 1.5 | 0.58 | 0.53 | 91.63 | 0.1 | 0.05 | 44.72 |
| 2 | 0.73 | 0.51 | 69.6 | 0.14 | 0.04 | 32.73 |
| 3 | 0.89 | 0.44 | 49.17 | 0.17 | 0.06 | 33.78 |
| 4 | 1.11 | 0.82 | 73.72 | 0.17 | 0.11 | 63.13 |
| 6 | 1.83 | 1.26 | 69.21 | 0.29 | 0.27 | 93.33 |
| 8 | 1.31 | 0.65 | 49.25 | 0.24 | 0.15 | 63.22 |
| 12 | 0.61 | 0.45 | 75.06 | 0.17 | 0.11 | 66.14 |
| 24 | 0.11 | 0.04 | 37.2 | 0.06 | 0.01 | 12.66 |

3.5 Immediate Release Formulation (IR Beads)

Formulations for immediate release of anagrelide were prepared. Individual pharmacokinetic parameters and mean concentration data are presented in Tables 21-23.

TABLE 21

Individual and average pharmacokinetic parameters of anagrelide for baboons receiving 0.5 mg immediate release anagrelide beads (IR beads).

| Animal | Tmax (hr) | Cmax (ng/mL) | AUCall (hr * ng/mL) | HL_Lambda_z (hr) |
|---|---|---|---|---|
| 1 | 0.5 | 5.98 | 27.89 | 5.42 |
| 2 | 1 | 3.84 | 18.98 | 3.61 |
| 3 | 1 | 6.71 | 24.4 | 2.02 |
| 4 | 3 | 5.95 | 24.29 | 1.94 |
| 5 | 6 | 4.49 | 25.52 | 4.57 |
| 6 | 0.5 | 10.09 | 29.28 | 5.62 |
| Mean | 2 | 6.176 | 25.06 | 3.865 |
| SD | 2.168 | 2.19 | 3.581 | 1.622 |
| CV % | 108.4 | 35.5 | 14.3 | 42 |

TABLE 22

Individual and average pharmacokinetic parameters of 3-OH anagrelide for baboons receiving 0.5 mg immediate release anagrelide beads (IR beads).

| Animal | Tmax (hr) | Cmax (ng/mL) | AUCall (hr * ng/mL) | HL_Lambda_z (hr) |
|---|---|---|---|---|
| 1 | 0.5 | 1.14 | 9.07 | 7.04 |
| 2 | 1 | 0.51 | 2.74 | 2.94 |
| 3 | 1 | 0.71 | 3.71 | 5.94 |
| 4 | 3 | 1.1 | 6.39 | 3.81 |
| 5 | 6 | 0.79 | 5.77 | 5.85 |
| 6 | 0.5 | 1.27 | 4.55 | 7.2 |
| Mean | 2 | 0.92 | 5.369 | 5.462 |
| SD | 2.168 | 0.295 | 2.247 | 1.731 |
| CV % | 108.4 | 32.1 | 41.8 | 31.7 |

TABLE 23

Mean plasma concentration of anagrelide and 3-OH anagrelide in baboons receiving 0.5 mg immediate release anagrelide beads (IR beads).

IR Beads

| | Anagrelide | | | 3-OH Anagrelide | | |
|---|---|---|---|---|---|---|
| Time (hr) | Mean (ng/mL) | SD (ng/mL) | CV % | Mean (ng/mL) | SD (ng/mL) | CV % |
| 0 | NA | NC | NC | NA | NC | NC |
| 0.5 | 3.86 | 3.64 | 94.32 | 0.64 | 0.46 | 72.87 |
| 1 | 3.98 | 2.24 | 56.29 | 0.6 | 0.21 | 35.48 |
| 1.5 | 3.26 | 1.11 | 34.17 | 0.56 | 0.21 | 37.41 |
| 2 | 3.13 | 0.88 | 28.13 | 0.55 | 0.25 | 44.47 |
| 3 | 3.39 | 1.64 | 48.24 | 0.62 | 0.31 | 49.69 |
| 4 | 2.47 | 0.78 | 31.49 | 0.48 | 0.19 | 39.45 |
| 6 | 2.1 | 1.22 | 58.29 | 0.45 | 0.23 | 51.94 |
| 8 | 1.01 | 0.41 | 40.89 | 0.3 | 0.15 | 49.67 |
| 12 | 0.34 | 0.21 | 61.18 | 0.16 | 0.11 | 65.46 |
| 24 | 0.13 | 0.07 | 52.99 | 0.08 | 0 | 3.94 |

A summary of the pharmacokinetic parameters for all formulations is provided in Table 24.

TABLE 24

Summary of mean pharmacokinetic parameters for all formulations.

| | Anagrelide | | | 3-OH Anagrelide | | |
|---|---|---|---|---|---|---|
| | Mean | SD | CV % | Mean | SD | CV % |
| CR-Fast | | | | | | |
| Tmax (hr) | 5.333 | 1.633 | 30.6 | 5.667 | 1.966 | 34.7 |
| Cmax (ng/mL) | 2.659 | 0.996 | 37.5 | 0.427 | 0.22 | 51.4 |
| AUCall (hr*ng/mL) | 18.782 | 4.424 | 23.6 | 3.129 | 1.307 | 41.8 |
| HL_Lambda_z (hr) | 6.054 | 5.242 | 86.6 | 7.068 | 5.485 | 77.6 |
| AUCINF_obs (hr*ng/mL) | 20.992 | 4.917 | 23.4 | 4.22 | 1.711 | 40.5 |
| CR-Slow | | | | | | |
| Tmax (hr) | 5.833 | 2.041 | 35 | 6.5 | 3.209 | 49.4 |
| Cmax (ng/mL) | 2.23 | 1.17 | 52.4 | 0.368 | 0.234 | 63.5 |
| AUCall (hr*ng/mL) | 16.349 | 6.527 | 39.9 | 3.257 | 1.823 | 56 |
| HL_Lambda_z (hr) | 4.758 | 1.527 | 32.1 | 6.691 | 3.874 | 57.9 |
| AUCINF_obs (hr*ng/mL) | 18.643 | 5.783 | 31 | 4.015 | 1.802 | 44.9 |
| Enteric Coated | | | | | | |
| Tmax (hr) | 5.333 | 1.033 | 19.4 | 6 | 0 | 0 |
| Cmax (ng/mL) | 4.876 | 3.469 | 71.1 | 0.898 | 0.675 | 75.2 |
| AUCall (hr*ng/mL) | 27.045 | 18.658 | 69 | 5.67 | 3.754 | 66.2 |
| HL_Lambda_z (hr) | 4.15 | 1.783 | 43 | 4.723 | 3.629 | 76.8 |
| AUCINF_obs (hr*ng/mL) | 28.329 | 18.558 | 65.5 | 6.975 | 3.956 | 56.7 |
| IR Beads | | | | | | |
| Tmax (hr) | 2 | 2.168 | 108.4 | 2.083 | 2.108 | 101.2 |
| Cmax (ng/mL) | 6.176 | 2.19 | 35.5 | 0.867 | 0.275 | 31.7 |
| AUCall (hr*ng/mL) | 25.06 | 3.581 | 14.3 | 5.297 | 2.107 | 39.8 |
| HL_Lambda_z (hr) | 3.865 | 1.622 | 42 | 5.462 | 1.731 | 31.7 |
| AUCINF_obs (hr*ng/mL) | 25.877 | 3.871 | 15 | 6.176 | 2.222 | 36 |
| IR Shire | | | | | | |
| Tmax (hr) | 2 | 1.095 | 54.8 | 2.083 | 1.114 | 53.5 |
| Cmax (ng/mL) | 5.444 | 1.945 | 35.7 | 1.052 | 0.619 | 58.9 |
| AUCall (hr*ng/mL) | 27.841 | 4.36 | 15.7 | 5.459 | 2.056 | 37.7 |
| HL_Lambda_z (hr) | 2.342 | 0.981 | 41.9 | 3.612 | 1.165 | 32.3 |
| AUCINF_obs (hr*ng/mL) | 29.082 | 4.302 | 14.8 | 6.313 | 2.411 | 38.2 |

4. Discussion

Baboon Pharmacokinetics:

All samples at time=zero, with the exception of one (animal 3 receiving IR-Shire formulation), reported concentrations that were below the lower limit of quantitation for parent and metabolite, confirming the lack of a carryover effect and that the washout period between treatments was adequate.

Following administration of the Shire material, $T_{max}$ (mean±SD) for anagrelide was 2.0±1.0 hours, indicating rapid absorption. The $T_{max}$ (mean±SD) for 3-OH anagrelide was 1.9±1.1 hours. The CR-Fast, CR-Slow and EC bead formulations each delayed $T_{max}$ for the parent anagrelide and its metabolite 3-OH anagrelide, by at least 2.5-fold. The longest $T_{max}$ observed was for the CR-Slow composition, with an average of 5.833±2.23. The trend for $T_{max}$ was IR (Shire)=IR Bead<CR-Fast=Enteric Coated<CR-Slow.

Following administration of the instant release Shire material, $C_{max}$ (mean±SD) for anagrelide was 5.4±1.9 ng/mL hours. The $C_{max}$ (mean±SD) for 3-OH anagrelide was 1.1±0.62 ng/mL. The CR-Fast, CR-Slow and EC bead formulations each decreased $C_{max}$ for the parent and metabolite. The CR compositions produced the most dramatic decreases in $C_{max}$ for anagrelide, both of which decreased $C_{max}$ by at least half. The $C_{max}$ for the EC formulation was almost equivalent to the IR-Shire and IR bead formulations. The trend for $C_{max}$ Following administration of the instant release Shire material, exposure to anagrelide ($AUC_{all}$; mean±SD) was 27.8±4.4 hr*ng/mL. The $AUC_{all}$ (mean±SD) for 3-OH anagrelide was 5.5±2.1 ng/mL. The CR-Slow and CR-Fast bead compositions each decreased exposure for the parent and metabolite, while the EC formulation showed equivalent exposure to the IR-Shire and IR bead formulations. Exposure to the parent was about 60% and 70% of the IR, for the CRFast and CR-Slow, respectively. The trend for $AUC_{all}$ was IR (Shire)=IR Bead=EC>CRSlow>CR-Fast.

The terminal elimination half-life values appear to be increased in the controlled or modified release compositions, relative to the Shire instant release formulation. In extended release compositions, drug absorption can be slowed by the delayed release of the drug, resulting in a "flip-flop" situation, where the K>Ka.

A summary of mean pharmacokinetic parameters of anagrelide, 3-OH anagrelide and RL603 from 38 volunteers given a single 1 mg dose of immediate release anagrelide (Agrylin® (Shire)) is shown in Table 25, which provides a summary of Shire data on file with the FDA (Evidence for the primary role of anagrelide's major metabolite, 3-hydroxy anagrelide in the drug's clinical activity; available, for example, at the website fda.gov/ohrms/dockets/dailys/04/aug04/081604/04p-0365-cp00001-08-Tab-G-vol1.pdf)).

TABLE 25

Summary of mean pharmacokinetic parameters of anagrelide and 3-OH anagrelide

| Compound | $AUC_{0-inf} \pm RSD$ (%) (ng·h/mL) | $C_{max} \pm RSD$ (%) (ng/mL) | $T_{max} \pm RSD$ (%) (h) | $t_{1/2} \pm RSD$ (%) (h)$^3$ |
|---|---|---|---|---|
| Anagrelide | 11.1 ± 37.6 | 4.99 ± 74.4 | 1.3 ± 53.8 | 1.5 ± 49.8 |
| BCH24426 (3-HA) | 18.0 ± 35.6 | 5.47 ± 56.9 | 1.28 ± 58.1 | 2.5 ± 28.7 |
| RL603 | 16.0 ± 32.3 | 1.36 ± 34.0 | 2.5 ± 58.5 | 7.8 ± 31.1 |

Comparison of Baboon Pharmacokinetics to Human Pharmacokinetics

The metabolic capacity of the baboon for anagrelide is not known. It is hypothesized that humans primarily form the 3-OH anagrelide via first pass hepatic metabolism, although there are no absolute oral bioavailability data to confirm this hypothesis. Gut metabolism of anagrelide in humans is considered negligible based on in vitro studies. Examination of the ratios of metabolite to parent suggests that there are species differences in metabolism of anagrelide, although the source and impact of these differences is not known. There do not appear to be differences in the formation of the 3-OH anagrelide metabolite as a function of the different formulations.

The marketed immediate release form of anagrelide (Xagrid®, Agrylin®; IR-Shire), appears to have similar exposure as the IR beads prepared as described herein. Formal bioequivalence calculations demonstrated equivalent peak and total exposures between the two immediate release compositions. The enteric coated (EC) formulation behaved as expected, demonstrating an apparent lag time, with peak exposure occurring as the drug is released in the GI tract when the relevant pH is achieved. The EC formulation exhibited AUC values similar to the IR formulation. The time to maximum concentration, $C_{max}$, of the anagrelide was IR-Shire=IR bead<CR-Fast=Enteric Coated<CR-Slow. The controlled release compositions also dampened the maximum observed concentration of anagrelide. The $C_{max}$ for anagrelide was decreased after administration of the CR-slow and CR-fast compositions, both of which decreased $C_{max}$ by at least half. The $C_{max}$ for the EC formulation was similar to the IR-Shire and IR bead formulations. The trend for $C_{max}$ anagrelide, as depicted by $AUC_\infty$ ($AUC_{inf}$) was decreased for the CR-slow and CR-fast compositions, whereas, the EC formulation showed exposure similar to the IR-Shire and IR bead formulations. Exposure to the parent drug (anagrelide) was about 60% and 70% of the IR, for the CR-fast and CR-slow compositions, respectively. The trend for $AUC_{inf}$ was IR-Shire=IR bead=EC>CR-Slow>CR-Fast. The apparent terminal elimination half-lives for anagrelide from the controlled release compositions are longer compared to the immediate release formulations. Due to the slower systemic drug absorption from the CR compositions, the apparent longer elimination half lives are probably a result of classic flip-flop kinetics. The data show that the CR compositions decrease the peak plasma concentration while maintaining total exposure equivalent to the immediate release formulation (IR-Shire).

Bioequivalence Study

A formal bioequivalence approach was undertaken to compare the pharmacokinetics of the IR-Shire immediate release anagrelide product to the IR bead anagrelide product prepared as described herein.

All subjects' data were included in calculations. As per the FDA Guidance document on bioequivalence (U.S. Department of Health and Human Services, Food and Drug Administration Center for Drug Evaluation and Research (CDER); Guidance for Industry Bioavailability and Bioequivalence; Studies for Orally Administered Drug Products—General Considerations; July 2002), a subject for whom a predose value is less than or equal to 5 percent of $C_{max}$ in that subject, that subject's data can be included in the calculations. Animal 2 presented a predose concentration for the IR-Shire material of 74 ng/mL; this sample was repeated and returned the original value. Ratios for the test product versus the reference product are presented in Table 26.

TABLE 26

Test mean/Reference mean rations of anagrelide and 3-OH anagrelide pharmacokinetic parameters.

| | Anagrelide | | | | | | |
|---|---|---|---|---|---|---|---|
| | IR Shire (Reference) | | | IR Beads (Test) | | | Ratio |
| | Mean | SD | % CV | Mean | SD | % CV | (T/R) |
| Tmax | 2.00 | 2.17 | 108 | 2.17 | 1.33 | 61 | 1.08 |
| Cmax | 6.18 | 2.19 | 35 | 5.40 | 1.91 | 35 | 0.87 |
| AUCall | 25.06 | 3.58 | 14 | 27.17 | 3.28 | 12 | 1.08 |
| HL_Lambda_z | 3.87 | 1.62 | 42 | 2.42 | 1.11 | 46 | 0.63 |
| AUCINF_obs | 25.88 | 3.87 | 15 | 28.89 | 4.11 | 14 | 1.12 |
| | 3-OH Anagrelide | | | | | | |
| | IR Shire(Reference) | | | IR Beads (Test) | | | Ratio |
| | Mean | SD | % CV | Mean | SD | % CV | (T/R) |
| Tmax | 2.00 | 2.17 | 108 | 2.08 | 1.1143 | 53 | 1.04 |
| Cmax | 0.92 | 0.30 | 32 | 1.05 | 0.6193 | 59 | 1.14 |
| AUCall | 5.37 | 2.25 | 42 | 5.44 | 2.0587 | 38 | 1.01 |

TABLE 26-continued

Test mean/Reference mean rations of anagrelide and 3-OH anagrelide pharmacokinetic parameters.

| HL_Lambda_z | 5.46 | 1.73 | 32 | 3.62 | 1.1616 | 32 | 0.66 |
|---|---|---|---|---|---|---|---|
| AUCINF_obs | 6.25 | 2.35 | 38 | 6.29 | 2.4178 | 38 | 1.01 |

Values of $C_{max}$, $AUC_{all}$, $AUC_{inf}$ and $T_{max}$ mean ratios for anagrelide and 3-OH anagrelide for the IR beads (test) versus IR-Shire (reference) product administered are within the acceptable range of 0.8-1.2. The apparent half-life mean ratios for parent and metabolite are 0.63 and 0.66, respectively. With respect to peak and total exposure, the two formulations appear to be bioequivalent.

4. In Vivo Human Clinical Trials—Comparison to Immediate Release Formulations

Model predictions were used to understand the impact of blending the controlled release (CR) compositions provided herein with immediate release (IR) formulations provided herein, to achieve an optimal pharmacokinetic profile. A substantial difference in peak plasma concentrations for a blend of CR and IR was predicted with a 50/50 blend based on mathematical model predictions. Model predictions estimated an approximately 50% decrease in $C_{max}$ while maintaining approximately 80% of the AUC. Based on the animal data and the single dose blend predictions, a 50/50 IR-CR (composition A) and a 100% CR composition (formulation B) were selected for testing.

A randomized open-label three way cross-over study to compare the pharmacokinetics of two exemplary formulations (formulation A and formulation B) of anagrelide with the marketed formulation of anagrelide (Xagrid®, Shire Pharmaceuticals, formulation C) in healthy human subjects was performed.

For the exemplary formulations, the unit dose was 0.1 mg, while the unit dose of the reference anagrelide (formulation C) was 0.5 mg. For the comparison, subjects were divided into three groups (A, B and C). The dosing regime for the subjects administered the exemplary formulations A and B was administration of a single dose of 5×0.1 mg capsules per subject of either formulation A or B. The dosing regime for subjects administered the control immediate release formulation (formulation C) was a single dosage of 1×0.5 mg capsule per subject. Blood samples were collected prior to study drug administration and at 0.25, 0.5, 0.75, 1, 1.5, 2, 3, 4, 6, 8, 12, 18, 24 and 30 hours post-dose in each period The criteria for evaluation included $AUC_{0-t}$, $AUC_{0-inf}$, $C_{max}$, $AUC_{t/inf}$, $T_{max}$, $T_{1/2\ el}$ and $K_{el}$. The results for anagrelide are shown below in Table 27, and the results for 3-OH anagrelide are shown in Table 28.

TABLE 27

Summary of results of anagrelide formulations and treatment comparisons

SUMMARY OF RESULTS
ANAGRELIDE
N = 12

| Parameters | | Test A (Anagrelide IR/CR) | | | Test B (Anagrelide CR) | | | Reference (Xagid (C)) | | |
|---|---|---|---|---|---|---|---|---|---|---|
| | | Mean | SD | CV (%) | Mean | SD | CV (%) | Mean | SD | CV (%) |
| $AUC_{0-t}$ | (pg·h/mL) | 3484.54 | 1898.80 | 54.49 | 2684.02 | 1529.38 | 56.98 | 4588.93 | 2852.30 | 62.16 |
| $AUC_{0-inf}$* | (pg·h/mL) | 3911.71 | 1852.89 | 47.37 | 3355.11 | 1445.27 | 43.08 | 4937.21 | 2869.41 | 58.12 |
| $AUC_{t/inf}$* | (%) | 92.48 | 5.29 | 5.72 | 82.89 | 8.31 | 10.03 | 98.18 | 0.27 | 0.28 |
| $C_{max}$ | (pg/mL) | 914.85 | 543.43 | 59.40 | 428.37 | 305.49 | 71.32 | 1715.86 | 832.87 | 48.54 |
| $T_{max}$ | (h) | 0.864 | 0.368 | 42.64 | 2.63 | 0.71 | 27.11 | 1.07 | 0.41 | 38.20 |
| $T_{max}$** | (h) | 0.750 | 0.525 | — | 3.00 | 1.00 | — | 1.00 | 0.39 | — |
| $K_{el}$ | (h⁻¹) | 0.1503 | 0.1033 | 68.71 | 0.0800 | 0.0551 | 68.89 | 0.5277 | 0.0520 | 9.86 |
| $T_{1/2\ el}$ | (h) | 6.32 | 3.77 | 59.61 | 11.58 | 5.47 | 47.27 | 1.33 | 0.17 | 12.62 |

*For these parameters, N = 11
**Medians and interquartile ranges are presented.

Treatment Comparisons

| | | | 90% Geometric C.I.[2] | | |
|---|---|---|---|---|---|
| Statistical Analysis (ANOVA) | Treatment Comparisons | Ratio of LS Means | Lower | Upper | Intra-Subject CV |
| $AUC_{0-t}$ | Anagrelide IR/CR (A) vs Xagrid (C) | 77.72% | 71.13% | 84.92% | 12.64% |
| | Anagrelide CR (B) vs Xagrid (C) | 59.24% | 54.22% | 64.73% | |
| $AUC_{0-inf}$* | Anagrelide IR/CR (A) vs Xagrid (C) | 81.54% | 73.52% | 90.44% | 14.01% |
| | Anagrelide CR (B) vs Xagrid (C) | 71.58% | 64.54% | 79.39% | |
| $C_{max}$ | Anagrelide IR/CR (A) vs Xagrid (C) | 50.45% | 42.52% | 59.86% | 24.65% |
| | Anagrelide CR (B) vs Xagrid (C) | 22.84% | 19.25% | 27.10% | |

[1]Calculated using least-squares means (ln-transformed data)
[2]90% Geometric Confidence Interval using ln-transformed data
*For this parameter, N = 11

TABLE 28

Summary of results of 3-OH anagrelide formulations and treatment comparisons

3-HYDROXY ANAGRELIDE
N = 12

| Parameters | | Test-1 (Anagrelide IR/CR (A)) | | | Test-2 (Anagrelide CR (B)) | | | Reference (Xagrid C)) | | |
|---|---|---|---|---|---|---|---|---|---|---|
| | | Mean | SD | CV (%) | Mean | SD | CV (%) | Mean | SD | CV (%) |
| $AUC_{0-t}$ | (pg·h/mL) | 7807.63 | 3499.88 | 44.83 | 5990.49 | 2223.51 | 37.12 | 8960.93 | 3119.42 | 34.81 |
| $AUC_{0-inf}$ | (pg h/mL) | 8369.65 | 3542.34 | 42.32 | 7188.87 | 2219.60 | 30.88 | 9295.74 | 3163.37 | 34.03 |
| $AUC_{t/inf}$ | (%) | 92.57 | 3.97 | 4.29 | 82.89 | 9.62 | 11.60 | 96.24 | 1.16 | 1.21 |
| $C_{max}$ | (pg/mL) | 1941.66 | 647.94 | 33.37 | 733.18 | 334.64 | 45.64 | 3125.02 | 556.89 | 17.82 |
| $T_{max}$ | (h) | 0.743 | 0.328 | 44.17 | 2.33 | 0.75 | 32.09 | 0.817 | 0.367 | 45.00 |
| $T_{max}$* | (h) | 0.625 | 0.313 | — | 2.00 | 1.00 | — | 0.750 | 0.487 | — |
| $K_d$ | ($h^{-1}$) | 0.1304 | 0.0547 | 41.96 | 0.0735 | 0.0337 | 45.87 | 0.3011 | 0.0640 | 21.27 |
| $T_{1/2\ el}$ | (h) | 6.26 | 2.97 | 47.47 | 11.57 | 5.37 | 46.37 | 2.39 | 0.48 | 20.12 |

Treatment Comparisons

| Statistical Analysis (ANOVA) | Treatment Comparisons | Ratio of LS Means[1] | 90% Geometric C.I.[2] | | Intra-Subject CV |
|---|---|---|---|---|---|
| | | | Lower | Upper | |
| $AUC_{0-t}$ | Anagrelide IR/CR (A) vs Xagrid (C) | 84.12% | 75.71% | 93.71% | 15.43% |
| | Anagrelide CR (B) vs Xagrid (C) | 66.55% | 59.74% | 74.14% | |
| $AUC_{0-inf}$ | Anagrelide IR/CR (A) vs Xagrid (C) | 87.53% | 78.95% | 97.03% | 14.72% |
| | Anagrelide CR (B) vs Xagrid (C) | 77.77% | 70.16% | 86.22% | |
| $C_{max}$ | Anagrelide IR/CR (A) vs Xagrid (C) | 59.66% | 49.85% | 71.40% | 25.94% |
| | Anagrelide CR (B) vs Xagrid (C) | 22.01% | 18.39% | 26.34% | |

[1]Calculated using least-squares means (ln-transformed data)
[2]90% Geometric Confidence Interval using ln-transformed data
*Medians and interquartile ranges are presented.

Results:

The extent of absorption for formulation A (CR/IR blend) as demonstrated by anagrelide $AUC_{0-t}$ and $AUC_{0-inf}$ was 77.72% and 81.54%, respectively, relative to the control immediate release formulation (treatment C (Xagrid®)). The extent of anagrelide absorption for formulation B (CR formulation) also was decreased (59.24% and 71.58%) relative to the immediate release control (treatment C (Xagrid®)). Total exposure for formulation B was probably underestimated with the selected sampling scheme because of its extended apparent terminal half-life of 11.58 h (in comparison, the mean $T_{1/2\ el}$ for the control (Xagrid®) is 1.33 h). The rate of absorption, approximated by $C_{max}$ and $T_{max}$, is also significantly slower in the controlled release formulations A and B as compared to the control immediate release formulation (treatment C (Xagrid®)), particularly for formulation B where the $C_{max}$ is 22.84% of the control's $C_{max}$ and $T_{max}$ is delayed by two hours.

Overall, the results indicate that the exemplary formulations (and in particular formulation B) performed as intended, by increasing the duration of exposure and reducing the peak plasma concentration compared to the control (Xagrid®, formulation C).

Statistical Analysis

For anagrelide and 3-hydroxy anagrelide, analysis of variance was performed on the ln-transformed data of $AUC_{0-t}$, $AUC_{0-\infty}$, and $C_{max}$. ANOVA was also carried out on the untransformed data of $T_{max}$, $T_{1/2\ el}$ and $K_{el}$. All ANOVAs were performed with the SAS (release 8.02 for Windows) General Linear Models Procedure (GLM). The model included sequence, subject within sequence, period and treatment as factors. The sequence effect was tested using subjects within sequence effect as the error term. The treatment and period effects were tested against the residual mean square error. All sums of squares (Types I, II, III and IV) were reported. Probability (p) values were derived from Type III sums of squares. For all analyses, effects were considered statistically significant if the probability associated with 'F' was less than 0.05. When the difference between treatments was statistically significant, Duncan's Multiple Range test was used to determine which treatments were significantly different. Based on pairwise comparisons of the ln-transformed $AUC_{0-t}$, $AUC_{0-\infty}$ and $C_{max}$ data, the ratios of the least-squares means, calculated according to the formula "e (X−Y)×100", as well as the 90% geometric confidence intervals for ln-transformed $AUC_{0-t}$, $AUC_{0-\infty}$ and $C_{max}$ were determined. Finally, the intra-subject CVs were also determined.

Pharmacokinetic Analysis

The pharmacokinetic parameters for this study were $AUC_{0-t}$, $AUC_{0-\infty}$, $C_{max}$, $AUC_{t/\infty}$, $T_{max}$, $K_{el}$ and $T_{1/2\ el}$. Blood samples for pharmacokinetic analysis were collected at pre-dose and at 0.25, 0.5, 0.75, 1, 1.5, 2, 3, 4, 6, 8, 12, 18, 24, and 30 hours post-dose in each period. For anagrelide, subject No. 06, the elimination rate constant for Treatment B could not be properly estimated and this subject was excluded from all analyses involving $AUC_{0-inf}$, $AUC_{t/inf}$, $K_{el}$ and $T_{1/2\ el}$ (total number of subjects was 11 for these parameters).

For anagrelide and 3-hydroxy anagrelide a statistically significant difference between treatments was detected using ANOVA for ln-transformed $AUC_{0-t}$, $AUC_{0-\infty}$ and $C_{max}$. For anagrelide, the $AUC_{0-t}$, $AUC_{0-\infty}$ and $C_{max}$ were greater for Treatment C (control IR anagrelide formulation, XAGRID®, Shire) compared to Treatment A (IR/CR bead blend) and B (CR bead formulation) and greater for Treatment A compared to Treatment B according to Duncan's Multiple Range Test. For 3-hydroxy anagrelide, the $AUC_{0-t}$ and $C_{max}$ were greater for Treatment C compared to Treatment A and B and greater for Treatment A compared to Treatment B whereas the $AUC_{0-\infty}$ was greater for Treatment C compared to Treatments A and B.

The intra-subject CVs for $AUC_{0-t}$, $AUC_{0-inf}$ and $C_{max}$ were respectively 12.64%, 14.01% and 24.65% for anagrelide and respectively 15.43%, 14.72% and 25.94% for 3-hydroxy anagrelide. The extent of absorption for Treatment A (IR/CR blend) as demonstrated by $AUC_{0-t}$ and $AUC_{0-\infty}$ was 77.72% and 81.54%, respectively, relative to Treatment C(XAGRID®). The extent of absorption for Treatment B (CR formulation) also was decreased (59.24% and 71.58%) relative to Treatment C(XAGRID®). Total exposure for the CR formulation (Treatment B) was probably underestimated with the selected sampling scheme because of its extended apparent terminal half-life of 11.58 h (in comparison, the mean $T_{1/2\ el}$ for XAGRID® is 1.33 h). The rate of absorption, approximated by $C_{max}$ and $T_{max}$, is also significantly slower in the CR formulations (Treatments A and B) compared to Treatment C(XAGRID®), particularly for Treatment B where the $C_{max}$ is 22.84% of XAGRID's $C_{max}$ and $T_{max}$ is delayed by two hours. The design of the study was adequate to determine the pharmacokinetic parameters of the test and the reference formulations. The washout period was sufficient to allow the complete elimination of the drug before period 2 administration and to avoid any carry-over effects.

Discussion

The extent of absorption for Treatment A as demonstrated by $AUC_{0-t}$ and AUC was 77.72% and 81.54%, respectively, relative to control immediate release formulation (Treatment C, XAGRID®). The extent of absorption for Treatment B also was decreased (59.24% and 71.58%) relative to the control (Treatment C, XAGRID®). Total exposure for the CR formulation (Treatment B) was probably underestimated with the selected sampling scheme because of its extended apparent terminal half-life of 11.58 h (in comparison, the mean $T_{1/2\ el}$ for XAGRID® is 1.33 h). The rate of absorption, approximated by $C_{max}$ and $T_{max}$, is also significantly slower in the CR formulations (Treatments A and B) compared to Treatment C (XAGRID®), particularly for Treatment B where the $C_{max}$ is 22.84% of XAGRID's $C_{max}$ and $T_{max}$ is delayed by two hours.

The results indicate that the CR formulation (Treatment B) reduced the peak plasma concentration while increasing the duration of exposure or maintaining sufficient total exposure compared to the immediate release formulation (XAGRID®, Shire, (Treatment C).

5. In Vivo Dose Escalation Study

A placebo-controlled, double-blind repeat-dose, dose-escalation, sequential cohort study was conducted to evaluate the pharmacokinetics and pharmacodynamics of a controlled release composition of anagrelide as described herein in healthy subjects. An objective of the study was to explore the dose-response relationship for effects on platelet counts of a low dose range of a composition of anagrelide as described herein in healthy subjects. Other objectives of the study included determining the time course of effect and recovery of a range of doses of the composition including anagrelide on platelet count, determining the effects of a range of doses of the anagrelide compositions on platelet aggregation (collagen and ADP as agonists), determining the single and repeat dose pharmacokinetics of the anagrelide composition, and exploring the safety and tolerability of the compositions given as single doses and repeatedly for up to 21 days.

Eligible subjects were treated as follows:

Subjects were admitted to the unit on day 1 in the morning after an overnight fast and remain in the unit until 4 hours after morning dosing on day 5.

Subjects received a single dose of controlled release composition including anagrelide (or matching placebo) on day 1 in the morning.

Subjects commenced repeat dosing twice a day with the controlled release anagrelide composition on the morning of day 3 and remained in the unit until 4 hours after morning dose on day 5.

Subjects continued repeat dosing twice a day dosing with the controlled release anagrelide composition as outpatients. Dosing continued until the morning of day 23.

All morning doses were taken after an overnight fast of at least 8 hour.

All evening doses were taken at least 2 hour after food consumption. No food was to be consumed for at least 1 hour after any dose (4 hours for the morning doses on day 1 and day 23).

On day 6-day 21, blood was taken pre-dosing of the controlled release anagrelide composition for full blood count (FBC) and platelet count (every day), trough PK (day 7, day 10, day 13, day 16 and day 19) and clinical chemistry (day 13).

Subjects were readmitted to the unit on the morning of day 22 and remained there until day 25 so that the PK of the final dose of the controlled release composition containing anagrelide on day 23 could be followed for 48 hours.

Subjects returned to the clinic daily from day 26 to day 31 for FBC and platelet counts.

Subjects returned for a follow up visit 14-16 days after the last dose of the controlled release composition containing anagrelide.

Study Population:

Healthy male and female subjects aged 18-50 years

Investigational Product:

A controlled release composition of anagrelide as described above in Table 4 of Example 1 (composition 2—fast release with seal coat) was used in unit doses of 100 µg and 300 µg, administered orally. The CR formulation was selected on the basis of a substantially lower peak plasma levels in relation to the overall exposure, demonstrating a $C_{max}$ that was about 25% of the $C_{max}$ of an immediate release anagrelide formulation but an $AUC_{0-last}$ that was about 60% of an immediate release anagrelide formulation (XAGRID®).

Dose:

In this protocol, 4 cohorts of 200 µg, 300 µg, 400 µg and 600 µg doses of the controlled release composition including anagrelide administered twice daily were studied.

Pharmacodynamics and PK:

Platelet count, collagen-induced platelet aggregation, ADP induced platelet aggregation, template bleeding time, $AUC_{0-t}$, $AUC_{0-\infty}$, $C_{max}$, $C_{min}$, $t_{1/2}$ z and $t_{max}$ were determined.

The starting dose of 200 µg (as a single dose on day 1 and then twice a day for 21 days) was chosen as a dose unlikely to cause any clinically significant reduction in platelet counts in healthy subjects. This starting dose was chosen because identification of the lowest dose of the controlled release composition containing anagrelide producing any effect on platelet counts was of interest. In each subsequent cohort the dose was increased by 200 µg twice a day with the objective of identifying the dose range that lowers platelet counts by 30-50%. With daily monitoring of platelet counts, this escalation was determined to allow identification of the effective dose range of the controlled release composition of anagrelide without placing the subjects at significant clinical risk.

Efficacy Analyses

The primary efficacy endpoint was selected to be the percentage change in the platelet count from day −1 to day 23 (at least 30% reduction in platelet number from baseline). The efficacy analysis also tested for a linear dose trend across the dose range (placebo, 200 µg to top dose). This analysis was carried out using a linear power model with dose as covariate.

Results

The study started with 200 μg, 400 μg and 600 μg twice per day (b.i.d.) orally as per protocol. At doses of 600 μg b.i.d. the platelets fell to an unacceptable level and dosing was stopped on days 12-14 for each subject. Doses in the subsequent dose group were reduced to 300 μg b.i.d. Over a 21 day course of therapy, there was no evidence for anagrelide accumulation in the plasma. Additionally, the results showed no evidence of auto-induction of the anagrelide clearance. The results also suggest a linear dose trend across the dose range over a 21 day course of therapy.

| | | Cohort | | | |
|---|---|---|---|---|---|
| | | 1 (0.2 mg) | 4 (0.3 mg) | 2 (0.4 mg) | 3 (0.6 mg) |
| Parameter | Day | Mean (SD) | Mean (SD) | Mean (SD) | Mean (SD) |
| Summary of Results Anagrelide Dose-normalized (to 0.2 mg) PK Parameters[1] | | | | | |
| $C_{max}$ (pg/mL) | 1 | 333.83 (155.21) | 284.33 (189.75) | 234.25 (164.93) | 303.94 (149.09) |
| | 23 | 353.85 (130.20) | 223.86 (128.96) | 330.54 (156.71) | — |
| $AUC_{0-inf}$ (pg * h/mL) | 1 | 2451.21 (2069.69) | 2238.96 (1491.20) | 3476.93 (2704.81) | 2739.47 (2106.38) |
| | 23 | 3248.54 (2138.60) | 2101.11 (—) | 3284.60 (1006.83) | — |
| $AUC_{0-t}$ (pg * h/mL) | 1 | 1723.57 (879.68) | 1824.45 (1372.03) | 1658.95 (782.85) | 2255.07 (1505.74) |
| | 23 | — | — | — | — |
| $AUC_{0-\tau}$ (pg * h/mL) | 1 | 1754.73 (711.41) | 1630.94 (1062.74) | 1479.75 (554.09) | 1963.94 (1036.97) |
| | 23 | 2002.51 (668.49) | 1873.15 (1110.82) | 2260.52 (951.57) | — |
| $T_{max}$ (h)[2] | 1 | 4.00 (1.52) | 3.61 (1.75) | 3.51 (0.98) | 4.00 (0.75) |
| | 23 | 3.00 (1.50) | 2.00 (1.02) | 3.02 (1.00) | — |
| $K_{el}$ (h$^{-1}$) | 1 | 0.1908 (0.1609) | 0.1685 (0.2243) | 0.0426 (0.0315) | 0.0490 (0.0325) |
| | 23 | 0.0871 (0.0917) | 0.0321 (—) | 0.0567 (0.0274) | — |
| $t_{1/2}$ (h) | 1 | 22.93 (45.61) | 14.33 (10.60) | 56.15 (85.16) | 19.53 (10.70) |
| | 23 | 34.32 (45.94) | 21.58 (—) | 15.13 (8.46) | — |
| Summary of Results 3-Hydroxy-Anagrelide Dose-normalized (to 0.2 mg) PK Parameters[1] | | | | | |
| $C_{max}$ (pg/mL) | 1 | 615.42 (181.58) | 401.42 (111.46) | 358.28 (231.04) | 444.22 (109.00) |
| | 23 | 755.69 (203.45) | 458.37 (158.60) | 515.80 (182.84) | — |
| $AUC_{0-inf}$ (pg * h/mL) | 1 | 4695.70 (1545.65) | 4461.86 (1118.15) | 3986.74 (1177.80) | 4605.80 (1769.24) |
| | 23 | 7278.41 (2302.06) | 5458.94 (1617.89) | 6183.31 (2066.46) | — |
| $AUC_{0-t}$ (pg * h/mL) | 1 | 4046.22 (1388.12) | 3403.06 (1102.42) | 3366.45 (1098.70) | 3939.12 (1160.95) |
| | 23 | — | — | — | — |
| $AUC_{0-\tau}$ (pg * h/mL) | 1 | 4179.16 (1278.48) | 2990.87 (755.10) | 3049.25 (815.26) | 3508.58 (592.68) |
| | 23 | 5662.47 (1442.58) | 4280.75 (1110.23) | 4810.60 (1556.96) | — |
| $T_{max}$ (h)[2] | 1 | 4.01 (0.02) | 3.61 (1.00) | 3.51 (0.98) | 4.00 (0.00) |
| | 23 | 3.00 (0.75) | 3.00 (1.00) | 3.02 (1.51) | — |
| $K_{el}$ (h$^{-1}$) | 1 | 0.0985 (0.0363) | 0.0596 (0.0357) | 0.0641 (0.0218) | 0.0673 (0.0295) |
| | 23 | 0.0608 (0.0246) | 0.0492 (0.0141) | 0.0527 (0.0127) | — |
| $t_{1/2}$ (h) | 1 | 7.78 (2.45) | 15.30 (8.40) | 11.64 (3.15) | 12.87 (7.78) |
| | 23 | 12.69 (4.14) | 15.13 (4.96) | 13.77 (3.30) | — |
| Summary of Results Anagrelide + 3-Hydroxy-Anagrelide Compound Analysis Dose-normalized (to 0.2 mg) PK Parameters[1] | | | | | |
| $C_{max}$ (pmol/mL) | 1 | 3.49 (1.16) | 2.55 (1.04) | 2.23 (1.48) | 2.78 (0.91) |
| | 23 | 4.13 (1.25) | 2.52 (1.01) | 3.19 (1.24) | — |
| $AUC_{0-inf}$ (pmol * h/mL) | 1 | 24.08 (9.34) | 24.44 (9.61) | 19.23 (1.03) | 27.45 (16.27) |
| | 23 | 37.51 (13.20) | 32.61 (15.14) | 33.65 (12.42) | — |
| $AUC_{0-t}$ (pmol * h/mL) | 1 | 22.41 (9.14) | 19.82 (9.17) | 18.82 (6.55) | 23.36 (9.98) |
| | 23 | — | — | — | — |
| $AUC_{0-\tau}$ (pmol * h/mL) | 1 | 21.98 (7.49) | 17.29 (6.85) | 16.98 (4.96) | 20.56 (6.07) |
| | 23 | 29.36 (8.37) | 23.05 (8.12) | 26.51 (9.16) | — |
| $T_{max}$ (h)[2] | 1 | 4.00 (1.50) | 3.61 (1.75) | 3.51 (0.98) | 3.50 (1.00) |
| | 23 | 3.00 (0.75) | 3.00 (1.00) | 3.02 (1.00) | — |
| $K_{el}$ (h$^{-1}$) | 1 | 0.1255 (0.0584) | 0.0772 (0.0430) | 0.0721 (0.0274) | 0.0769 (0.0342) |
| | 23 | 0.0656 (0.0371) | 0.0509 (0.0201) | 0.0550 (0.0150) | — |
| $t_{1/2}$ (h) | 1 | 6.68 (3.29) | 11.62 (6.34) | 10.68 (3.81) | 12.45 (10.50) |
| | 23 | 13.11 (5.82) | 15.52 (6.17) | 13.51 (4.15) | — |

[1] Only $C_{max}$, $AUC_{0-inf}$, $AUC_{0-t}$ and $AUC_{0-\tau}$ are dose-normalized
[2] Median and interquartile range are reported instead of mean and standard deviation Since modifications will be apparent to those of skill in this art, it is intended that this invention be limited only by the scope of the appended claims.

What is claimed:

1. A pharmaceutical composition in unit dosage form, comprising:
a solid support core of a substantially water soluble, swellable or insoluble material, wherein the solid support is from 85-95% by weight of the composition;
a substrate layer comprising a binder and microparticles of anagrelide hydrochloride monohydrate in hydrated crystal form, in an amount that is equivalent to from 50 µg to 10 mg of anagrelide free base, wherein at least 90% of the microparticles are 25 microns or less and the binder is present at a weight of 0.1-5% by weight of the composition;
a release control component comprising a water insoluble polymer and a plasticizer, wherein the release control component is present at about 1-10% by weight of the composition; and
a seal coat layer comprising a substantially water-soluble polymer, wherein the seal coat is present at about 1-5% by weight of the composition and is disposed between the substrate layer and the release control component and reduces chemical interaction between the anagrelide hydrochloride monohydrate in the substrate layer and the plasticizer in the release control component,
wherein the hydrated crystal form of the anagrelide hydrochloride monohydrate in the composition has a shelf stability of at least three months under normal storage conditions.

2. The composition of claim 1, wherein the solid support comprises one or a plurality of spheroid granules, pellets or beads.

3. The composition of claim 1 that is formulated as a tablet or capsule for single dosage administration.

4. The composition of claim 1, wherein:
the anagrelide hydrochloride monohydrate in the substrate layer is at a weight of at or about 0.12% by weight of the composition, and the binder in the substrate layer is hydoxypropylmethylcellulose at a weight of at or about 2.3% of the composition;
the solid support is in the form of a plurality of non-pareil sugar spheres at a weight of at or about 89.42% by weight of the composition;
the seal coat comprises hydroxypropyl methylcellulose at a weight of at or about 4.6% by weight of the composition; and
the controlled release component comprises ethylcellulose at or about 1.55% by weight of the composition, hydroxypropyl methylcellulose at or about 0.52% by weight of the composition and triethyl citrate at or about 0.89% by weight of the composition.

5. The composition of claim 1, wherein the amount of anagrelide hydrochloride monohydrate is in an amount equivalent to about 100 µg, about 200 µg, about 300 µg, about 400 µg, about 500 µg, about 600 µg, about 700 µg, about 800 µg, about 900 µg or in an amount equivalent to about 1000 µg of anagrelide free base.

6. A composition in unit dosage form, comprising:
a solid support core of a nonpareil sugar spheres;
a substrate layer comprising microparticles of anagrelide hydrochloride monohydrate in hydrated crystal form in an amount equivalent to about 0.1 to 1.0 mg of anagrelide free base, and hydroxypropyl methyl cellulose as a binder;
a seal coat layer comprising hydroxypropyl methylcellulose; and
a release control component for controlled release of the anagrelide hydrochloride comprising ethyl cellulose, hydroxypropyl methylcellulose and triethylacetate;
wherein the seal coat is disposed between the substrate layer and the release control component, and reduces chemical interaction between the anagrelide hydrochloride monohydrate in the substrate layer and the triethylacetate in the release control component, and
wherein the hydrated crystal form of the anagrelide hydrochloride monohydrate in the composition has a shelf stability of at least three months under normal storage conditions.

7. The composition of claim 6, wherein the amount of anagrelide hydrochloride monohydrate is in an amount equivalent to about 100 µg, about 200 µg, about 300 µg, about 400 µg, about 500 µg, about 600 µg, about 700 µg, about 800 µg, about 900 µg or in an amount equivalent to about 1000 µg of anagrelide free base.

8. The composition of claim 1, further comprising granules, pellets or beads that include an immediate release form of anagrelide hydrochloride monohydrate in an amount between about 10 ng to about 1000 µg.

9. The composition of claim 6, wherein the seal coat is present at a weight of from about 1-5% by weight of the composition.

10. The composition of claim 1, wherein the hydrated crystal form of the anagrelide hydrochloride monohydrate is substantially maintained for a shelf period of at least six months.

11. The composition of claim 1, that has a moisture content of between at or about 0.05% and at or about 2% by weight.

12. The composition of claim 1, wherein the anagrelide hydrochloride monohydrate has an effective moisture of between about 3% and about 10% by weight.

13. The composition of claim 1, wherein the substrate layer comprises microparticles of the anagrelide hydrochloride monohydrate in an amount equivalent to about 100 µg, about 200 µg, about 300 µg, about 400 µg, about 500 µg, about 600 µg, about 700 µg, about 800 µg, about 900 µg or in an amount equivalent to about 1000 µg of anagrelide free base.

14. The composition of claim 1, wherein the binder in the substrate layer is a low molecular weight hydroxypropyl methyl cellulose.

15. The composition of claim 1, wherein at least 50% of the microparticles are 12 microns or less.

16. The composition of claim 1, wherein the solid support core is a non-pareil sugar sphere.

17. The composition of claim 6, wherein the seal coat layer is present at a weight of 1-5% by weight of the composition.

18. The composition of claim 6, wherein the release control component is present at a weight of 1-5% by weight of the composition.

19. The composition of claim 1, wherein the release control component comprises a film-forming polymer selected from among ethyl cellulose, hydroxypropyl cellulose, hydroxypropyl methyl cellulose or a mixture of two or more thereof.

20. The composition of claim 1, wherein the release control component includes at or about 60% to at or about 95% by weight of ethyl cellulose and at or about 40% to at or about 5% by weight of hydroxypropyl methylcellulose.

21. The composition of claim 1, wherein the substrate layer comprises microparticles of the anagrelide hydrochloride monohydrate in hydrated crystal form in an amount equivalent to about 100 µg, about 200 µg, about 300 µg, about 400 µg, about 500 µg, about 600 µg, about 700 µg, about 800 µg, about 900 µg or in an amount equivalent to about 1000 µg of anagrelide free base, and the binder comprises hydroxypropyl methylcellulose;

the seal coat comprises hydroxypropyl methylcellulose at a weight of at or about 1% to at or about 5% by weight of the composition; and the release control component comprises ethylcellulose, hydroxypropyl methylcellulose and triethylcitrate.

22. The composition of 21, wherein the ethylcellulose is present in an amount to yield a ratio of ethylcellulose to the hydroxypropyl methylcellulose of 3:1 in the release control component.

23. The composition of 21, wherein the release control component is about 1% to at or about 5% by weight of the composition.

24. The composition of claim 8, wherein the immediate release form of anagrelide hydrochloride monohydrate comprises 50% or less by weight of the dosage form.

25. A method for reducing platelet count in a subject, comprising:

administering to a subject a composition of claim 1, wherein:

the composition delivers an amount of anagrelide hydrochloride effective to reduce platelet count in the subject by at least 10% of pre-treatment levels.

26. The method of claim 25, wherein the subject has a normal platelet count prior to treatment.

27. The method of claim 26, wherein the platelet count is reduced to at least a low normal level.

28. The method of claim 25, wherein the subject has an above normal platelet count prior to treatment.

29. The method of claim 28, wherein the platelet count is reduced to at or about $600 \times 10^3$ platelets/µl or less.

30. The method of claim 25, wherein the subject is a mammal.

31. The method of claim 25, wherein the subject is a human.

32. The method of claim 25, wherein the subject has a disease selected from among vascular disease, hypercholesterolemia, hypertension, atherosclerosis, a thrombosis, a myeloproliferative disease, a condition or disorder resulting from a thrombotic event, diabetes mellitus, familial hypercholesterolemia, familial combined hyperlipidemia, familial dysbetalipoproteinemia, familial hypoalphalipo-proteinemia, hypothyroidism, cholesterol ester storage disease, systemic lupus erythematosus, homocysteinemia, chronic renal insufficiency, chronic vitamin D intoxication, pseudo-xanthoma elasticum, idiopathic arterial calcification, aortic valvular calcification, Werner's syndrome and elevated risk of experiencing a vaso-occlusive event.

33. The method of claim 32, wherein:

the subject has a vascular disease selected from among arteriosclerosis, atherosclerosis, accelerated atherosclerosis, atherosclerosis lesions, focal calcific arteriosclerosis (Mönckeberg's sclerosis), arteriolosclerosis, cardiovascular disease, cerebrovascular disease, renovascular disease, mesenteric vascular disease, pulmonary vascular disease, ocular vascular disease and peripheral vascular disease; or the subject has a myeloproliferative disease or disorder selected from among polycythemia vera, essential thrombocythemia and idiopathic myelofibrosis; or the subject has a thrombosis selected from among an arterial thrombosis, a stent thrombosis, a graft thrombosis, a cardiac thrombosis, a coronary thrombosis, a heart valve thrombosis and a venous thrombosis; or the subject has a thrombotic event selected from among a myocardial infarction, a stroke, a transient ischemic attack, amaurosis fugax, aortic stenosis, cardiac stenosis, coronary stenosis and pulmonary stenosis.

34. The method of claim 25, wherein the controlled release composition is administered prior to or following a surgical procedure.

35. The method of claim 34, wherein the surgical procedure is selected from among coronary angiography, coronary stent placement, coronary by-pass surgery, carotid artery procedure, peripheral stent placement, vascular grafting, thrombectomy, peripheral vascular surgery, vascular surgery, organ transplant, artificial heart transplant, vascular angioplasty, vascular laser therapy, vascular replacement and vascular stenting.

36. The method of claim 25, wherein the controlled release composition is co-administered with another therapeutic agent selected from among an anti-inflammatory agent, an anti-thrombotic agent, an ADP receptor antagonist, a glycoprotein IIb/IIIa receptor inhibitor, an anti-coagulant agent, a thrombolytic agent, a cyclooxygenase-2 inhibitor, a PAR antagonist, a fibrinolytic agent, a lipid reducing agent, an angiotensin system inhibitor, an antihypertensive agent, a chemotherapeutic anti-cancer drug, an alkylating agent, a thromboxane synthetase inhibitor, a cell signaling molecule and a JAK-2 inhibitor.

37. The method of claim 36, wherein the therapeutic agent is selected from among:

an anti-inflammatory agent selected from among alclofenac, alclometasone dipropionate, algestone acetonide, alpha amylase, amcinafal, amcinafide, amfenac sodium, amiprilose hydrochloride, anakinra, anirolac, anitrazafen, apazone, aspirin, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate-sodium, meclofenamic acid, meclorisone dibutyrate, mefenamic acid, mesalamine, meseclazone, methyl-prednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, salicylates, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, glucocorticoids and zomepirac sodium;

an ADP receptor antagonist selected from among clopidogrel, ticlopidine, prasugrel, sulfinpyrazone, AZD6140, AZD6933 and AR-C69931;

a glycoprotein IIb/IIIa receptor inhibitor selected from among abciximab, fradafiban, lamifiban, lotrafiban, orbofiban, roxifiban, sibrafiban, tirofiban and xemilofiban;

an anti-coagulant agent selected from among a vitamin K antagonist, coumarin and coumarin derivatives, warfarin sodium; a heparin; ardeparin sodium; bivalirudin; bromindione; coumarin dalteparin sodium; desirudin; dicumarol; lyapolate sodium; nafamostat mesylate; phenprocoumon sulfatide; and tinzaparin sodium; or a thrombolytic agent selected from among ancrod, anistreplase, bisobrin lactate, brinolase, Hageman factor (i.e., factor XII) fragments, molsidomine, plasminogen activators such as streptokinase, tissue plasminogen activators (TPA), urokinase, TFPI, plasmin and plasminogen and inhibitors of coagulation factors IIa, Va, VIIa, VIIIa, IXa, Xa, XIa, XIIa and XIIIa;

a lipid reducing agent selected from among bezafibrate, ciprofibrate, clofibrate, etofibrate, fenofibrate, gemfibrozil, ronifibrate and simfibrate; a statin, atorvastatin, cerivastatin, fluvastatin, lovastatin, mevastatin, pitavastatin, pravastatin, rosuvastatin and simvastatin, niacin or a niacin derivative, including acipimox, aluminium nicotinate, niceritrol (penta-erythritol tetranicotinate), nicofuranose and nicotinyl alcohol; a bile acid sequestrant, including colesevelam, colestyramine, colestipol and colextran; a CETP inhibitor, such as anacetrapib; benfluorex; cholestyramine; dextrothyroxine; ezetimibe; laropiprant; meglutol; omega-3-triglycerides; policosanol; probucol; and tiadenol;

a cyclooxygenase-2 (COX-2) inhibitor selected from among aspirin, celecoxib, lumiracoxib and etoricoxib;

an angiotensin system inhibitor selected from among an angiotensin converting enzyme (ACE) inhibitor, an angiotensin II receptor antagonist, an agent that activates the catabolism of angiotensin II, and an agent that prevents the synthesis of angiotensin I from which angiotensin II is ultimately derived;

an ACE inhibitor selected from among benazepril, captopril, cilazapril, delapril, enalapril, fosinopril, imidapril, lisinopril, moexipril, perindopril, quinapril, ramipril, spirapril, temocapril, trandolapril and zofenopril;

an angiotensin II receptor antagonist selected from among azilsartan, candesartan, eprosartan, irbesartan, losartan, olmesartan, tasosartan, telmisartan and valsartan;

a chemotherapeutic anti-cancer drug selected from among busulfan, carmustine, chlorambucil, cyclophosphamide, doxorubicin, estramustine, hepsulfan, hydroxy-carbamide, ifosfamide, lomustine, melphalan, methotrexate, pipobroman and thioTEPA;

a thromboxane synthetase inhibitor selected from among aspirin, β-[4-(2-carboxy-1-propenyl)benzyl]pyridine hydrochloride (OKY-1555) and 1-carboxyhexyl-, 1-carboxyheptyl, and 1-carboxy-octyl-imidazoles, 4(Z)-6-[(4RS,5SR)-4-(2-hydroxyphenyl)-1,3-dioxan-5-yl] hex-4-enoic acid, BM-573, camonagrel, CGS-12970, daltroban, dazmegrel, DTTX30, E-6700, FCE-27262, imitrodast (CS-518), isbogrel (CV-4151), ketoconazole, KK-505, KY-063, nafagrel (DP-1904), ozagrel (OKY-046), picotamide, pirmagrel (CGS-13080), ridogrel, SQ29548, rolafagrel (FCE-22178), satigrel (E-5510), sulotroban, terbogrel and UK 38485;

a cell signaling molecule selected from among a cytokine, a growth factor, an interleukin, α-interferon, γ-interferon, transforming growth factor-β, neutrophil activating peptide-2 and its analogs, macrophage inflammatory protein and its analogs, and platelet-factor 4 and transforming growth factor-beta, and combinations thereof; and a JAK-2 inhibitor selected from among AT9283, VX-680, MK0457, TG101209, INCB018424, LS104, XLO19, TG101348, vorinostat, a 4-aryl-2-amino-pyridine and a 4-aryl-2-aminoalkyl-pyridine.

38. The method of claim 25, wherein the controlled release composition is administered orally.

39. The method of claim 32, wherein the disease is a myeloproliferative disease or disorder and platelet count is reduced by at least 20%.

40. The method of claim 39, wherein platelet count is reduced to an amount at or about $450 \times 10^3$ platelets per µl or less.

41. The method of claim 25, wherein the anagrelide hydrochloride monohydrate is administered in an amount of from about 200 µg to about 600 µg one or twice daily.

42. The method of claim 25, wherein the maximum observed plasma concentration (Cmax) of the anagrelide hydrochloride that is 50% or less of an immediate release formulation of anagrelide hydrochloride, and produces an area under the plasma concentration versus time curve (AUC) equal to or more than 55% of an immediate release formulation of anagrelide hydrochloride.

43. An article of manufacture, comprising:
a packaging material;
a composition of claim 1 within the packaging material; and
a label that indicates that the composition is used for treatment, prevention or amelioration of one or more symptoms of a platelet mediated disease or disorder, or a disease or disorder in which platelet number is implicated.

* * * * *